US007163681B2

(12) United States Patent
Giles-Komar et al.

(10) Patent No.: US 7,163,681 B2
(45) Date of Patent: Jan. 16, 2007

(54) ANTI-INTEGRIN ANTIBODIES, COMPOSITIONS, METHODS AND USES

(75) Inventors: Jill Giles-Komar, Downingtown, PA (US); Linda Snyder, Pottstown, PA (US); Mohit Trikha, Paoli, PA (US); Marian T. Nakada, Malvern, PA (US)

(73) Assignee: Centocor, Inc., Malvern, PA (US)

( * ) Notice: Subject to any disclaimer, the term of this patent is extended or adjusted under 35 U.S.C. 154(b) by 244 days.

(21) Appl. No.: 10/720,323

(22) Filed: Nov. 24, 2003

(65) Prior Publication Data

US 2004/0185507 A1 Sep. 23, 2004

Related U.S. Application Data

(63) Continuation-in-part of application No. 09/920,267, filed on Aug. 1, 2001.

(60) Provisional application No. 60/223,363, filed on Aug. 7, 2000.

(51) Int. Cl.
*A61K 39/395* (2006.01)
*C07K 16/28* (2006.01)

(52) U.S. Cl. ............... 424/144.1; 530/388.15; 530/388.22

(58) Field of Classification Search ........... 530/388.15, 530/388.22; 424/144.1
See application file for complete search history.

(56) References Cited

U.S. PATENT DOCUMENTS

| | | | |
|---|---|---|---|
| 5,674,483 A | 10/1997 | Tu et al. | |
| 5,753,230 A | 5/1998 | Brooks et al. | |
| 5,877,397 A * | 3/1999 | Lonberg et al. | ........... 800/18 |
| 5,985,278 A | 11/1999 | Mitjans et al. | |
| 6,171,588 B1 | 1/2001 | Carron et al. | |
| 6,342,221 B1 * | 1/2002 | Thorpe et al. | ........... 424/178.1 |
| 6,359,126 B1 | 3/2002 | Kim et al. | |
| 6,369,204 B1 | 4/2002 | Kim et al. | |
| 6,632,927 B1 * | 10/2003 | Adair et al. | ........... 530/387.3 |
| 2001/0011125 A1 | 8/2001 | Huse | |
| 2003/0143603 A1 * | 7/2003 | Giles-Komar et al. | ........ 435/6 |

FOREIGN PATENT DOCUMENTS

| | | |
|---|---|---|
| EP | 0 260 829 | 3/1988 |
| EP | 719859 A1 | 7/1996 |
| EP | 0 834 557 | 4/1998 |
| WO | WO 93/20229 A1 | 10/1993 |
| WO | WO 94/12181 A1 | 6/1994 |
| WO | WO 95/25543 A1 | 9/1995 |
| WO | WO 97/06791 A1 | 2/1997 |
| WO | WO 97/36859 A1 | 10/1997 |
| WO | WO 0031248 A | 6/2000 |
| WO | WO 0044404 A | 8/2000 |

OTHER PUBLICATIONS

Rudikoff et al Single amino acid substitution altering antigen-binding specificity. Proc Natl Acad Sci U S A. Mar. 1982;79(6):1979-83.*
Panka et al. Variable region framework differences result in decreased or increased affinity of variant anti-digoxin antibodies. Proc Natl Acad Sci U S A. 85(9):3080-3084, 1988.*
Amit et al., Three-dimensional structure of an antigen-antibody complex at 2.8 A resolution. Science. 233(4765):747-753, 1986.*
Wayner et al Integrins alpha v beta 3 and alpha v beta 5 contribute to cell attachment to vitronectin but differentially distribute on the cell surface. J Cell Biol. May 1991;113(4):919-29.*
Chemicon International catalog No. MAB1953Z, p. 1, Jan. 27, 2006.*
Tam et al, "Abciximab (ReoPro, Chimeric 7E3 Fab) Demonstrates equivalent affinity and functional blockade of glycoprotein IIb/IIIa and $\alpha_v\beta_3$ Integrins," vol. 98, No. 11, Sep. 15, 1998, pp. 1098-1091, USA.
Trikha et al, "A potential new application for a cardiovascular drug: Role for ReoPro (Abciximab), an inhibitor of GBIIB/IIIA and alphaVbeta3 integrins, as an anti-cancer agent," Proceedings of the American Association for Cancer Research, vol. 41, Mar. 2000, p. 577, USA.
Suzuki et al, "cDNA and amino acid sequences of the cell adhesion protein receptor recognizing vitronectin reveal a transmembrane domain and homologies with other adhesion protein receptors," Cell Biology, Nov. 1986, pp. 8614-8618, vol. 83, Proc. National Academy Science, USA.
Lehmann et al, "A monoclonal antibody inhibits adhesion to fibronectin and bitronectin of a colon carcinoma cell line and recognizes the integrins $\alpha_v\beta_3, \alpha_v\beta_5, \alpha_v\beta_6$," Cancer Research, 1994, pp. 2102-2107, vol. 52 USA.
Gunther Castl, Thomas Hermann, Mciahel, Steurer, Jorg Zmija, Eberhard Gunsilius, Clemens Unger, and Andrea Kraft, "Angiogenesis as a target for tumor treatment," Oncology, 1997, 177-84, vol. 54.
Brian P. Eliceiri and David A. Cheresh, "The role of alpha-v integrins during angiogenesis: insights into potential mechanisms of action and clinical development," The Journal of Clinical Investigation, May 1999, 1227-30, vol. 103, No. 9.
Martin Friedlander, Peter C. Brooks, Robert W. Shaffer, Christine M. Kincaid, Judith A. Varner, and David A. Cheresh, "Definition of Two Angiogenic Pathways by Distinct Alpha-V Integrins," Science, Dec. 1, 1995, 1500-2, vol. 270.
Lisa D. Taylor, Condie E. Carmack, Dennis Huszar, Kay M.Higgins, Roshanak Mashayekh, Getachew Sequar, Stephen R. Schramm, Chiung-Chi Kuo, Susan L. O'Donnell, Robert M. Kay, Olive S. Woodhouse, and Nils Lonberg, "Human immunoglobulin transgenes undergo rearrangement, somatic mutation and class switching in mice that lack endogenous IgM," International Immunology, 1994; 579-91, vol. 6 No. 4, Oxford University Press.

(Continued)

*Primary Examiner*—Maher M. Haddad
(74) *Attorney, Agent, or Firm*—Kenneth J. Dow

(57) ABSTRACT

The present invention relates to at least one novel anti-alpha-V subunit antibodies, including isolated nucleic acids that encode at least one anti-alpha-V subunit antibody, alpha-V subunit, vectors, host cells, transgenic animals or plants, and methods of making and using thereof, including therapeutic compositions, methods and devices.

20 Claims, 40 Drawing Sheets

OTHER PUBLICATIONS

Nils Lonberg, Lisa D. Taylor, Fiona A. Harding, Mary Trounstine, Kay M. Higgins, Stephen R. Schramm, Chiung-Chi Kuo, Roshanak Mashayekh, Kathryn Wymore, James G. McCabe, Donna Munoz-O'Regan, Susan L. O'Donnell, Elizabeth S. G. Lapachet, Tash Bengoechea, Diane M. Fishwild, Condie E. Carmack, Robert M. Kay and Dennis Huszar, "Antigen-specific human antibodies from mich comprising four distinct genetic modifications," Nature, Apr. 28, 1994, 856-9, vol. 368.

Michael Neuberger, "Generating high-avidity human Mabs in mice," Nature Biotechnology, Jul. 1996, 826, vol. 14.

Dianne M. Fishwild, Susan L. O'Donnell, Tash Bengoechea, Debra V. Hudson, Fiona Harding, Susan L. Bernhard, Debbie Jones, Robert M. Kay, Kay M. Higgins, Stephen R. Schramm, and Nils Lonberg, "High-avidity human IgG-kappa monoclonal antibodies from a novel strain of minilocus transgenic mice," Nature Biotechnology, Jul. 1996, 845-51, vol. 14.

Elizabeth A. Wayner, Robert A. Orlando and David A. Cheresh, "Integrins alpha v beta 3 and alpha v beta 5. Contribute to Cell Attachement to Vitronectin but Differentially Distribute on the Cell Surface," J. Cell Biology, May 1991, 919-29, vol. 113, No. 4.

John F. Marshall, Deborah C. Rutherford, Alison C.E. McCartney, Francesc Mitjans, Simon L. Goodman and Ian R. Hart, "Alpha v beta 1 is a receptor for vitronectin and fibriogen, and acts with alpha 5 beta 1 to mediate spreading on fibronectin," J. of Cell Science, 1995, 1227-38, vol. 108.

David A. Cheresh and Robert C. Spiro, "Biosynthetic and Functional Properties of an Arg-Gly-Asp-directed Receptor involved in Human Melanoma Cell Attachment to Vitronectin, Fibrinogen, and von Willebrand Factor," J. of Biological Chemistry, Dec. 25, 1987, 17703-11, vol. 262, No. 36.

Hans Kemperman, Yvonne M. Wijnands, and Ed Roos, "Alpha v Integrins on HT-29 Colon Carcinoma Cells: Adhesion to Fibronectin in Mediated Solely by Small Amounts of alpha v beta 6, and alpha v beta 5 is Codistributed with Actin Fibers," Experimental Cell Research, 1997, 156-64, vol. 234.

J. Orihara, "Sensitizing Capacity, Cross-Reactivity and Antigenic Determinants of Bisphenol A", The Journal of Stomatological Society, vol. 59, No. 2, Jun. 1992, pp. 439-455, English Abstract only.

M. Castillo et al., "Analysis of Industrial Effluents to Determine Endocrine-Disrupting Chemicals", Trends in Analytical Chemistry, vol. 16, No. 10, Nov. 12, 1997, pp. 574-583.

J. Gascon et al., "Detection of Endocrine-Disrupting Pesticides by Enzyme-Linked Immunosorbent Assay (ELISA): Application to Atrazine", Trends in Analytical Chemistry, vol. 16, No. 10, 1997, pp. 554-562.

Mitjans et al, "In Vivo Therapy of Malignant Melanoma by Means of Antagonists of αv Integrins," Int. J. Cancer, 2000, pp. 716-723, vol. 87, Wiley-Liss, Inc., Spain.

Mitjans et al, "An anti-αv-integrin antibody that blocks Integrin function Inhibits the development of a human melanoma in nude mice," Journal of Cell Science, 1995, pp. 2825-2838, vol. 108, The Company of Biologists Limited, Great Britain.

Casel et al, "RGD Peptides and Monoclonal Antibodies, Antagonists of $\alpha_v$-Integrin, Enter the Cells by Independent Endocytic Pathways," Laboratory Investigation, 2001, pp. 1615-1626, vol. 81, No. 12, The United States and Canadian Academy of Pathology, Inc, USA.

Mitijans et al, J. Cell Sci, 1995, [pp. 2825-2838, vol. 108.

Lehmann et al, Cancer Res, 1994, pp. 2102-2107, vol. 54.

Friedlander et al, Science, 1995, pp. 1500-1502, vol. 270.

Friedlander et al, Proc Natl Acad Sci, 1996, pp. 9764-9769, vol. 93 USA.

* cited by examiner

Binding of αVβ3 to GenO95 Plate in presence of 50 mM EDTA (no $Ca^{++}$) or with $Ca^{++}$ alone Binding of αVβ3 to C372A Plate in presence of 50 mM EDTA (no $Ca^{++}$) or with $Ca^{++}$ alone Binding of αVβ3 to c7E3 IgG Plate in presence of 50 mM EDTA (no $Ca^{++}$) or with $Ca^{++}$ alone Binding of αVβ3 to LM609 IgG Plate in presence of 50 mM EDTA (no $Ca^{++}$) or with $Ca^{++}$ alone ReoPro binding to A375S2 cells (n=4)

$K_d = 22 \pm 0.37 \times 10^{-9}$ M
$(1.1 \pm 0.19 \ \mu g/ml)$

Receptors/cell = 370,000 ± 190,000

ReoPro binding to HT-29 cells (n=5)

ReoPro binding to M21 cells (n=4)

$K_d = 10 \pm 2.00 \times 10^{-9}$ M
$(0.5 \pm 0.10 \ \mu g/ml)$

Receptors/cell = 660,000 ± 120,000

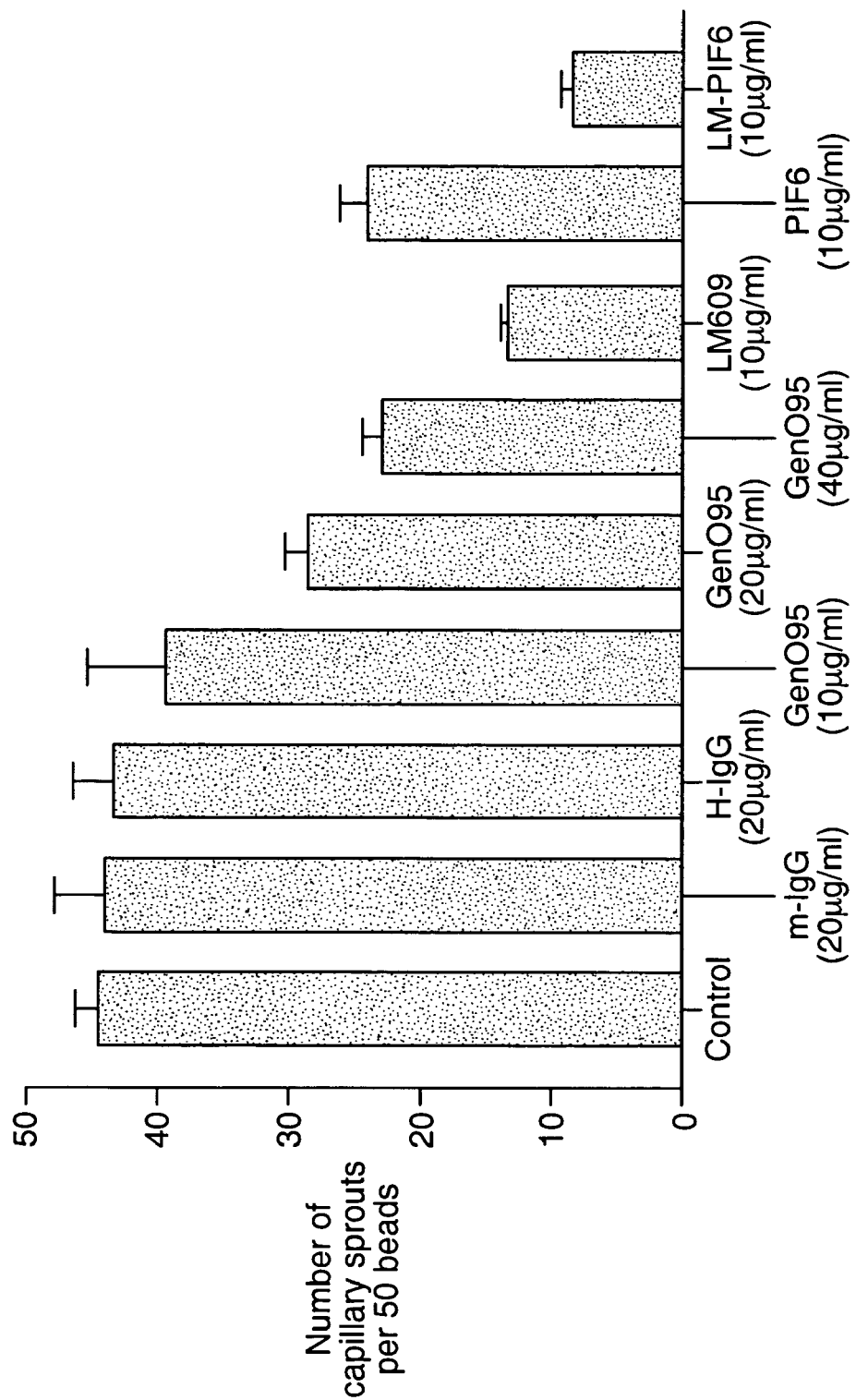

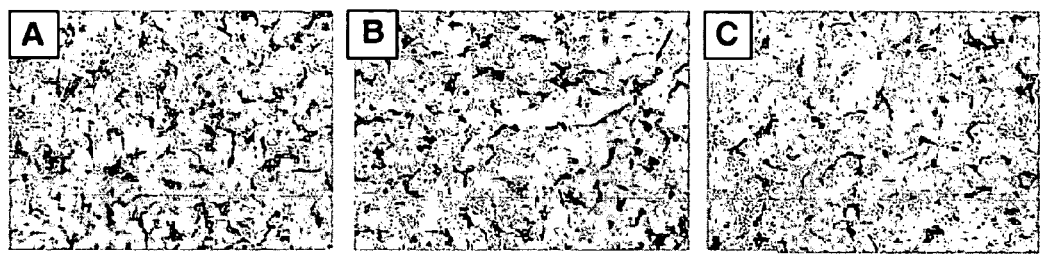
FIG. 16A  FIG. 16B  FIG. 16C
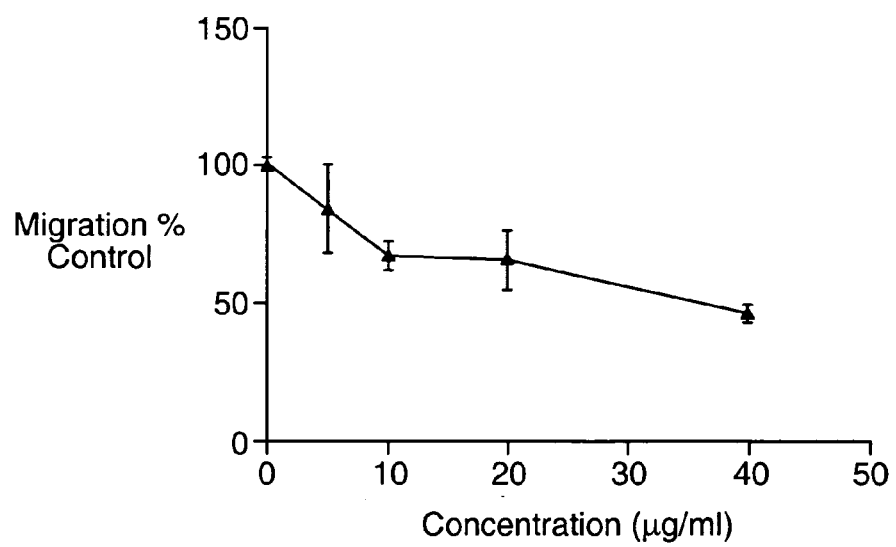
FIG. 16D

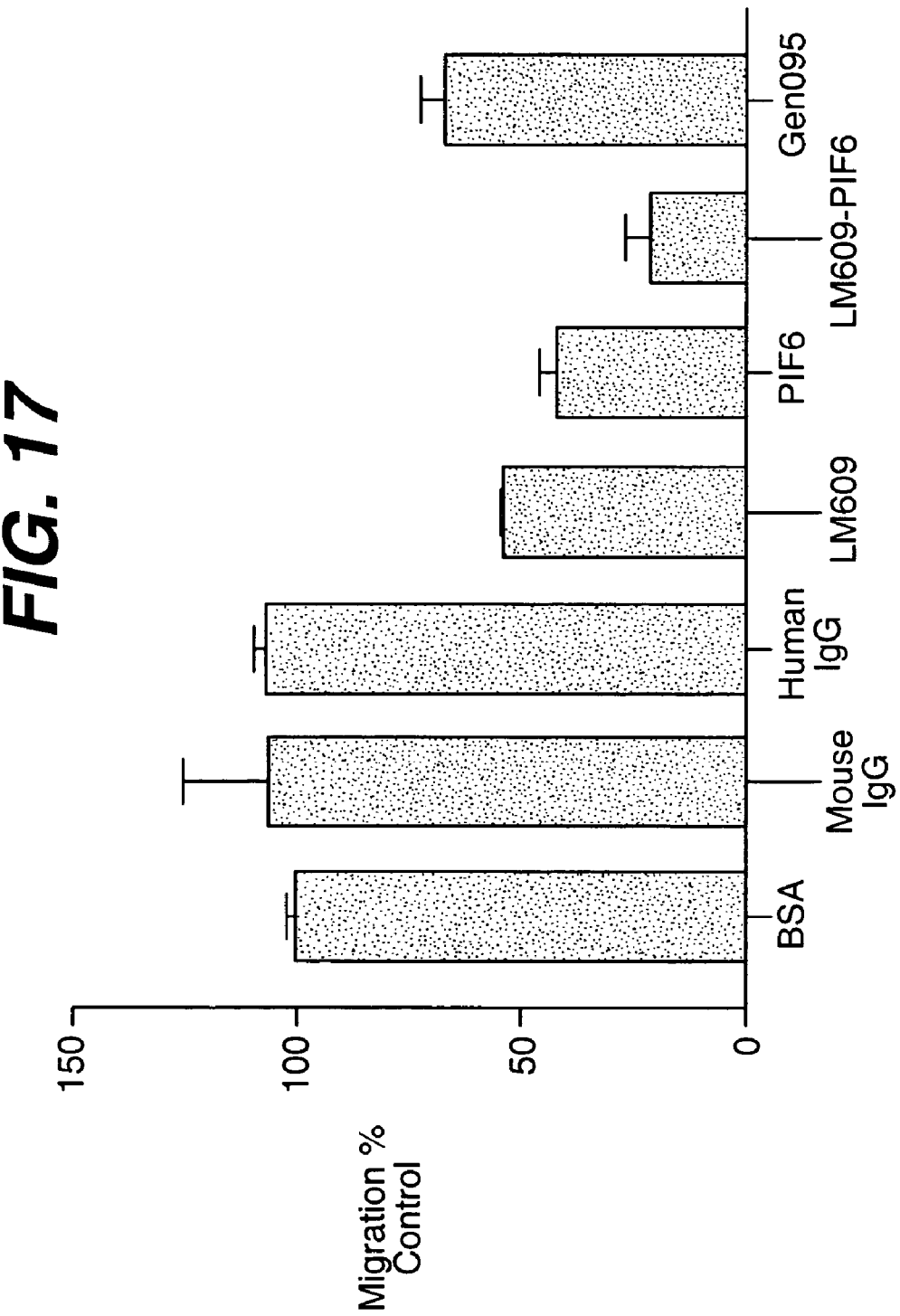

FIG. 19C  FIG. 19D  FIG. 19E
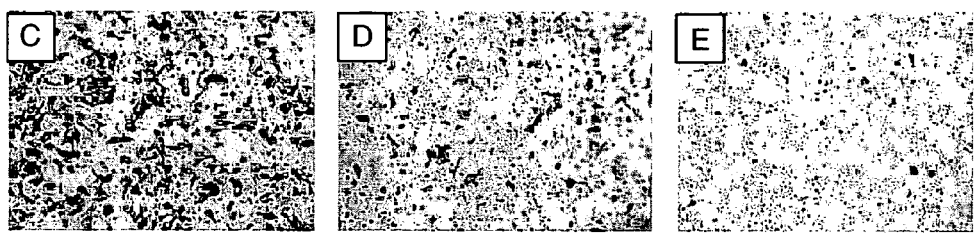

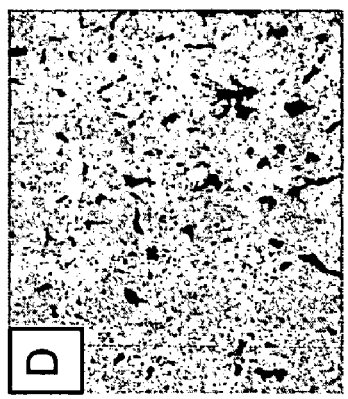
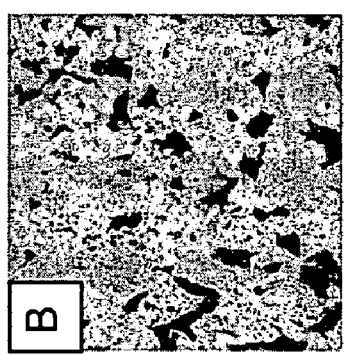
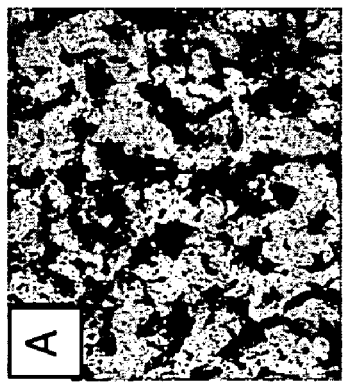
FIG. 20A  FIG. 20B  FIG. 20C  FIG. 20D

FIG. 22B
Mock transfected HEK cells
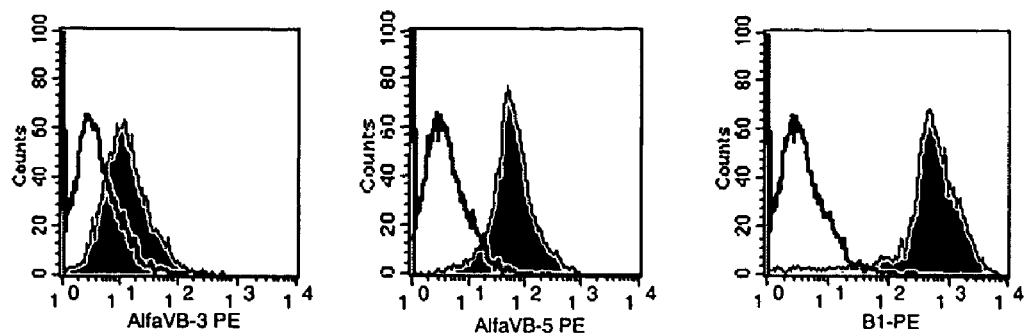
αvβ6 transfected HEK cells
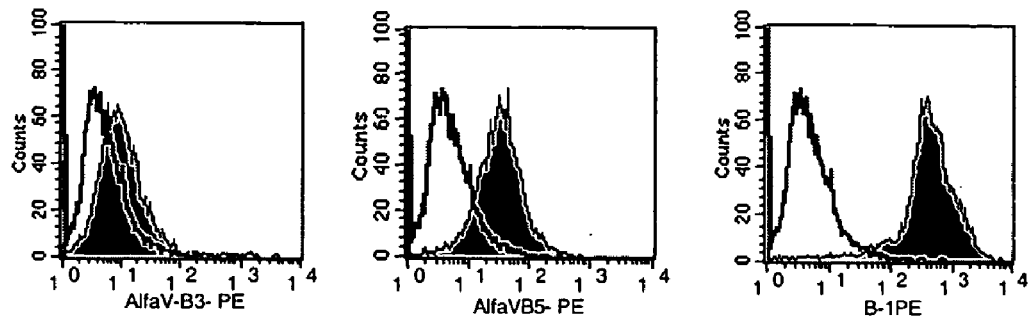

FIG. 22C
Mock 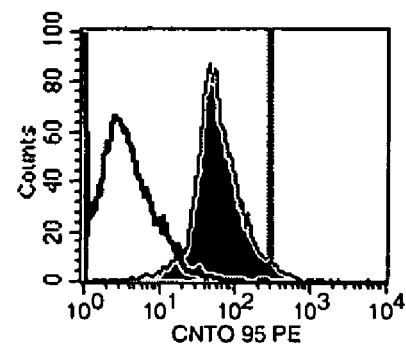
αv 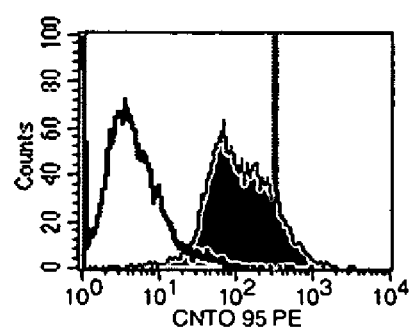
β6 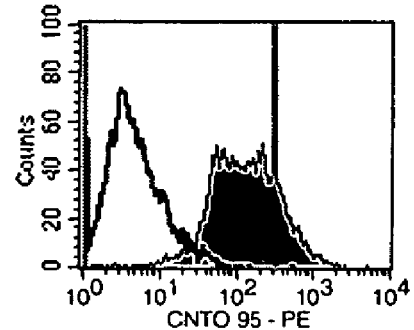
αvβ6 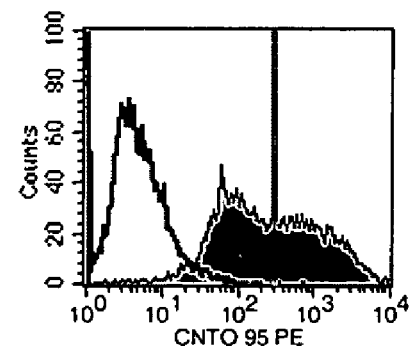

FIG. 22D
Mock transfected HEK cells
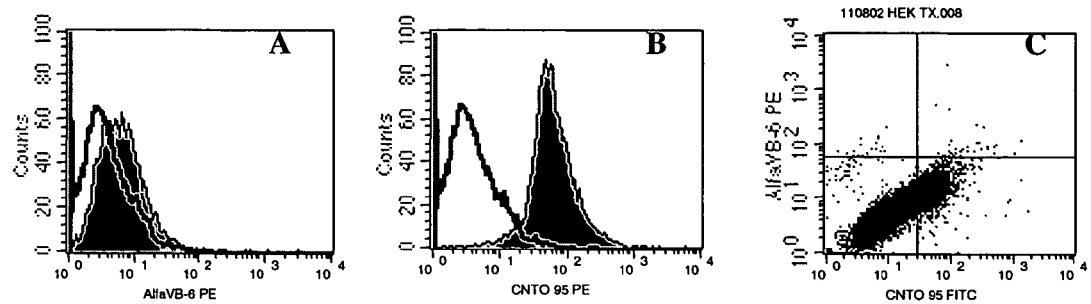
αvβ6 transfected HEK cells
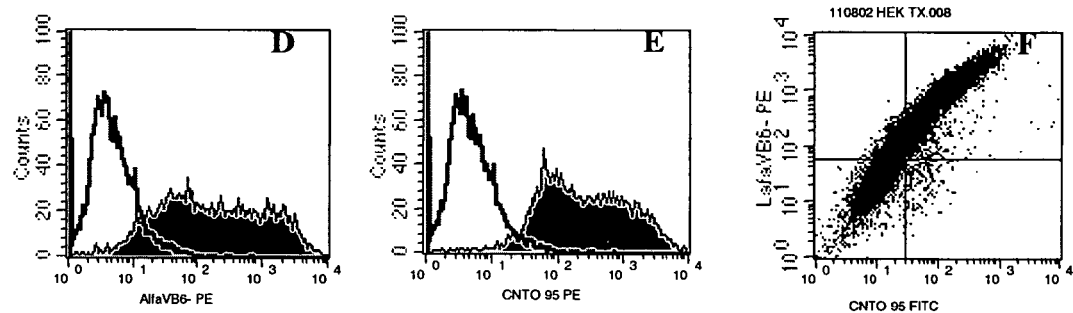

ANTI-INTEGRIN ANTIBODIES, COMPOSITIONS, METHODS AND USES

CROSS REFERENCE TO RELATED APPLICATIONS

This application is a continuation-in-part of U.S. application Ser. No. 09/920,267, filed Aug. 1, 2001, which claims priority to U.S. provisional application 60/223,363 filed Aug. 7, 2000, both of which are entirely incorporated herein by reference.

BACKGROUND OF THE INVENTION

1. Field of the Invention

The present invention relates to antibodies which bind to the alpha-V subunit of the integrin family of cell adhesion receptors, including specified portions or variants thereof. The antibodies of the invention are specific for at least one alpha-V subunit of a heterodimeric integrin receptor, such as an alpha-V-beta-1, alpha-V-beta-3, alpha-V-beta-5, alpha-V-beta-6, or alpha V-beta-8 heterodimeric integrin protein or fragment thereof. The invention also relates to nucleic acids encoding such anti-alpha-V subunit antibodies, complementary nucleic acids, vectors, host cells, and methods of making and using thereof, including therapeutic formulations, administration and devices.

2. Related Art

Integrins are a superfamily of cell adhesion receptors, which exist as heterodimeric transmembrane glycoproteins. They are part of a large family of cell adhesion receptors which are involved in cell-extracellular matrix and cell-cell interactions. Integrins play critical roles in cell adhesion to the extracellular matrix (ECM) which, in turn, mediates cell survival, proliferation and migration through intracellular signaling. The receptors consist of two subunits that are non-covalently bound. Those subunits are called alpha and beta. The alpha subunits all have some homology to each other, as do the beta subunits. The receptors always contain one alpha chain and one beta chain and are thus called heterodimeric. Both of the subunits contribute to the binding of ligand. Eighteen alpha subunits and eight beta subunits have been identified, which heterodimerize to form at least 24 distinct integrin receptors.

Among the variety of alpha chain subunits is a protein chain referred to as alpha V. The ITAGV gene encodes integrin alpha chain V (alphaV). The I-domain containing integrin alpha V undergoes post-translational cleavage to yield disulfide-linked heavy and light chains, that combine with multiple integrin beta chains to form different integrins. Alternative splicing of the gene yields 7 different transcripts; a, b, c, e, f, h, j altogether encoding 6 different protein isoforms of alphaV. Among the known associating beta chains (beta chains 1,3,5,6, and 8; 'ITGB1', 'ITGB3', 'ITGB5', 'ITGB6', and 'ITGB8'), each can interact with extracellular matrix ligands. The alpha V beta 3 integrin, perhaps the most studied of these, is referred to as the vitronectin receptor (VNR). In addition to providing for cell attachment to other cells or to extracellular proteins such as vitronectin (alphaVbeta3) and fibronectin (alphaVbeta6), the integrins are capable of intracellular signaling which provides clues for cell migration and secretion of or elaboration of other proteins involved in cell motility and invasion and angiogenesis. The alpha V integrin subfamily of integrins recognize the ligand motif arg-gly-asp (RGD) present in fibronection, vitronection, VonWillebrand factor, and fibrinogen.

It has been established that integrins which are alpha-V containing heterodimers, particularly alpha-V/beta-6, the receptor for fibronectin, are involved in adhesion of carcinoma cells to fibronectin and vitronectin. This is especially true for carcinoma cells arising from the malignant progression of colon cancer (Lehmann, M. et al. Cancer Res 1994, 54(8), 2102–7. Furthermore, integrin expression in colon cancer cells is regulated by the cytoplasmic domain of the beta-6 integrin subunit which signals through the ERK2 pathway (Niu, J. et al. Int. J. Cancer 2002, 99(4), 529–537) and beta6 expression is associated with secretion of gelatinase B, an enzyme involved in tumor cell invasion and metastatic mechanisms (Agrez, et al. Int. J. Cancer 1999, 81(1), 90–97).

There is now considerable evidence that progressive tumor growth is dependent upon angiogenesis, the formation of new blood vessels, to provide tumors with nutrients and oxygen, to carry away waste products and to act as conduits for the metastasis of tumor cells to distant sites (Gastl et al., Oncol. 54:177–184). Recent studies have further defined the roles of integrins in the angiogenic process. During angiogenesis, a number of integrins that are expressed on the surface of activated endothelial cells regulate critical adhesive interactions with a variety of ECM proteins to regulate distinct biological events such as cell migration, proliferation and differentiation. Specifically, the closely related but distinct integrins $\alpha V \beta 3$ and $\alpha V \beta 5$ have been shown to mediate independent pathways in the angiogenic process. An antibody generated against $\alpha V \beta 3$ blocked basic fibroblast growth factor (bFGF) induced angiogenesis, whereas an antibody specific to $\alpha V \beta 5$ inhibited vascular endothelial growth factor (VEGF) induced angiogenesis (Eliceiri, et al., J. Clin. Invest. 103: 1227–1230 (1999); Friedlander et al., Science 270: 1500–1502 (1995)). Therefore, integrins and especially the alpha V subunit containing integrins, are reasonable therapeutic targets for diseases that involve angiogenesis such as disease of the eye and neoplastic disease, tissue remodeling such as restenosis, and proliferation of certain cells types particularly epithelial and squamous cell carcinomas.

Non-human mammalian, chimeric, polyclonal (e.g., antisera) and/or monoclonal antibodies (Mabs) and fragments (e.g., proteolytic digestion or fusion protein products thereof) are potential therapeutic agents that are being investigated in some cases to attempt to treat certain diseases. However, such antibodies or fragments can elicit an immune response when administered to humans. Such an immune response can result in an immune complex-mediated clearance of the antibodies or fragments from the circulation, and make repeated administration unsuitable for therapy, thereby reducing the therapeutic benefit to the patient and limiting the readministration of the antibody or fragment. For example, repeated administration of antibodies or fragments comprising non-human portions can lead to serum sickness and/or anaphalaxis. In order to avoid these and other problems, a number of approaches have been taken to reduce the immunogenicity of such antibodies and portions thereof, including chimerization and humanization, as well known in the art. These and other approaches, however, still can result in antibodies or fragments having some immunogenicity, low affinity, low avidity, or with problems in cell culture, scale up, production, and/or low yields. Thus, such antibodies or fragments can be less than ideally suited for manufacture or use as therapeutic proteins.

Accordingly, there is a need to provide human antibodies to anti-integrin alpha-V subunit antibodies or fragments thereof that overcome one or more of these problems, as well as improvements over known antibodies or fragments thereof.

SUMMARY OF THE INVENTION

The present invention provides isolated human anti-integrin alpha-V subunit antibodies, immunoglobulins, cleavage products and other specified portions and variants thereof, as well as anti-alpha-V subunit antibody compositions, encoding or complementary nucleic acids, vectors, host cells, compositions, formulations, devices, transgenic animals, transgenic plants, and methods of making and using thereof, as described and enabled herein, in combination with what is known in the art. The antibodies of the invention bind the various forms of the alpha V subunit of the integrin receptor with particular affinity and specificity regardless of the various beta subunits of the integrin heterodimer to which the alpha V subunit is paired. Accordingly, the antibodies can be used in a variety of methods for diagnosing, treating, and/or preventing diseases involving cell adhesion mediated by the integrin receptor, particularly diseases involving alpha V integrin mediated angiogenesis, such as prostate cancer, colon cancer, and renal carcinoma.

Thus, in one embodiment, the present invention provides at least one isolated anti-integrin alpha-V subunit antibody as described herein. In one embodiment, the antibody according to the present invention includes any protein or peptide containing molecule that comprises at least a portion of a complementarity determining region (CDR) of a heavy or light chain or a ligand binding portion thereof derived from the antibody designated CNTO 95, in combination with a heavy chain or light chain variable region, a heavy chain or light chain constant region, a framework region, or any portion thereof, that can be incorporated into an antibody of the present invention. The antibody CNTO 95 described herein is a human anti-alpha V antibody derived from immunization of a transgenic mouse containing genes for the expression of human immunoglobulins. Thus, in one embodiment, the invention is directed to antibodies containing at least one CDR region or variable region derived from the CNTO 95 antibody. An antibody of the invention can include or be derived from any mammal, such as but not limited to a human, a mouse, a rabbit, a rat, a rodent, a primate, or any combination thereof, and the like, or the antibody can be derived from a synthetic source, such as a synthetic phage display library.

Particular therapeutic antibodies of the invention include human monoclonal antibody CNTO 95, and functionally equivalent antibodies which have the human heavy chain and human light chain amino acid sequences in their variable regions as set forth in SEQ ID NO: 7 and SEQ ID NO: 8 respectively, and conservative modifications thereof.

Still other particular human antibodies of the invention include those which comprise a CDR domain having a human heavy and light chain CDR1 region, a human heavy and light chain CDR2 region, and a human heavy and light chain CDR3 region, wherein (a) the CDR1, CDR2, and CDR3 of the human heavy chain regions comprise an amino acid sequence selected from the group consisting of the amino acid sequences of the CDR1, CDR2, and CDR3 regions shown in SEQ ID NOs: 1, 2 and 3, and conservative sequence modifications thereof, and (b) the CDRI, CDR2, and CDR3 of the human light chain regions comprise an amino acid sequence selected from the group consisting of the amino acid sequences of the CDRI, CDR2, and CDR3 regions shown in SEQ ID Nos: 3, 4 and 5, and conservative sequence modifications thereof. The antibody amino acid sequence can further optionally comprise at least one specified substitution, insertion or deletion as described herein or as known in the art.

Other particular antibodies of the invention include human monoclonal antibodies which bind to an epitope defined by antibody CNTO 95, and/or which compete for binding to the alpha V integrin subunit with antibody CNTO 95, or which have other functional binding characteristics exhibited by antibody CNTO 95. Such antibodies include, for example, those which bind to alpha V with a dissociation constant (KD) of $10^{-7}$ M or less, such as of $10^{-8}$ M or less, $10^{-9}$ M or less, $10^{-10}$M or less, or even lower (e.g., $10^{-11}$M or less). Such antibodies include those which competitively inhibit binding of the CNTO 95 antibody to human alpha-V integrin. Such antibodies further include those which exhibit no cross reactivity with murine anti alpha V antibodies LM609, PIF6, or VNR139.

Isolated human antibodies of the invention include a variety of antibody isotypes, such as IgG1, (e.g., IgGlk), IgG2, IgG3, IgG4, IgM, IgA1, IgA2, IgAsec, IgD, and IgE. The antibodies can be full-length antibodies (e.g., IgG1 or IgG3) or can include only an antigen-binding portion (e.g., a Fab, F(ab')2, Fv, or a single chain Fv fragment).

At least one antibody of the invention binds at least one specified epitope specific to at least one integrin alpha-V subunit protein, fragment, portion or any combination thereof. The epitope can comprise at least one antibody binding region that comprises at least one portion of said protein, which epitope is preferably comprised of at least 1–5 amino acids of at least one portion of an alpha-V subunit, such as but not limited to, (a) 29–48, 58–63, 69–79, 82–85, 88–134, 140–157, 161–183, 186–190, 192–198, 202–212, 215–217, 223–237, 240–244, 248–255, 259–268, 287–301, 313–322, 326–328, 332–344, 348–351, 354–365, 376–387, 393–401, 407–414, 417–419, 422–433, 443–451, 458–461, 465–469, 472, (b) 32–41, 46–47, 53–55, 58–69, 72–74, 77–79, 85–88, 91–94, 96–105, 110–113, 117–125, 129–142, 145–153, 155–159, 161–163, 166–170, 172–174, 184–197, 200–209, 215–218, 221–225, 184–197, 200–209, 215–218, 221–225, 227–250, 259–261, 263–267, 269–270, 275–281; and (c) 29–35, 43–45, 48–63, 67–69, 72–74, 80–82, 84–87, 95–105, 108–113, 117–142, 145–163, 166–170, 172–176, 184–186, 191–201, 204–206, 216–219, 224–226, 229–251, 260–262, 264–268, 276–282, 286–288, 294–299, 301–318, 323–325, 328–330, 338–342, 345–349, 353–358, of SEQ ID NO: 9, 16, and 17, respectively thereof, or such as but not limited to, at least one functional, extracellular, soluble, hydrophilic, external or cytoplasmic domain of said alpha-V subunit protein, or any portion thereof. Particularly preferred are antibodies which bind to substantially the same epitope on the alpha V integrin subunit defined by the epitope of CNTO 95, and/or which compete for binding to alpha V integrin with antibody CNTO 95, or which have other functional binding characteristics exhibited by antibody CNTO 95.

The present invention also provides at least one isolated anti-alpha-V subunit antibody as described herein, wherein the antibody has at least one activity, such as, but not limited to inhibition of vitronectin binding, inhibition of binding of alpha-V beta-3 to at least one of an alpha-V beta3 ligand or receptor, inhibition of binding of alpha-V beta-5 to at least one of an alpha-V beta-5 ligand or receptor, inhibition of binding of alpha-V beta6 to at least one of an alpha-V beta-6 ligand or receptor, angiogenesis modulation, binding to alpha-V subunit or single integrin expressing cells. A(n) anti-alpha-V subunit antibody can thus be screened for a corresponding activity according to known methods, such as but not limited to, competition with the CNTO 95 antibody for at least one biological activity towards an integrin alpha-V subunit protein.

The present invention provides, in one aspect, isolated nucleic acid molecules comprising, complementary, or hybridizing to, a polynucleotide encoding the specific anti-integrin alpha-V subunit antibodies described herein. Such nucleic acid molecules include those encoding all or a portion of a human monoclonal anti-alpha V antibody as described herein (e.g., which encode at least one light or heavy chain CDR of the antibody), as well as recombinant expression vectors which include such nucleic acids, and host cells transfected with such vectors. Methods of producing the antibodies by culturing such host cells are also encompassed by the invention. Particular nucleic acids provided by the invention comprise the nucleotide sequences shown in SEQ ID NOs: 10, 11 and 12 and SEQ ID NOs: 13, 14 and 15, which encode the heavy and light chains CDRs, respectively, of human anti-alpha V antibody CNTO 95 and the nucleic acids which encode the complete variable region of the heavy or light chain, respectively, as shown in SEQ ID Nos: 18 and 19. The present invention further provides recombinant vectors comprising said anti-integrin alpha-V subunit antibody nucleic acid molecules, host cells containing such nucleic acids and/or recombinant vectors, as well as methods of making and/or using such antibody nucleic acids, vectors and/or host cells.

The present invention also provides at least one method for expressing at least one anti-alpha-V subunit antibody as described herein, or alpha-V subunit anti-idiotype antibody as described herein, in a host cell, comprising culturing a host cell as described herein under conditions wherein at least one anti-alpha-V subunit antibody is expressed in detectable and/or recoverable amounts.

The present invention also provides at least one composition comprising (a) an isolated anti-alpha-V subunit antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition.

The present invention further provides at least one anti-alpha-V subunit antibody method or composition, for administering a therapeutically effective amount to modulate or treat at least one alpha-V subunit related condition in a cell, tissue, organ, animal or patient and/or, prior to, subsequent to, or during a related condition, as known in the art and/or as described herein. The compositions include, for example, pharmaceutical and diagnostic compositions/kits, comprising a pharmaceutically acceptable carrier and at least one human anti-alpha V antibody, or an antigen-binding portion thereof. In one embodiment, the composition comprises a combination of human antibodies or antigen-binding portions thereof, preferably each of which binds to a distinct epitope. For example, a pharmaceutical composition comprising a human monoclonal antibody that mediates highly effective killing of target cells in the presence of effector cells can be combined with the human monoclonal antibody hereof that inhibits the growth of cells expressing alpha V integrin. Thus, the combination provides multiple therapies tailored to provide the maximum therapeutic benefit. Compositions, e.g., pharmaceutical compositions, comprising a combination of at least one human anti alpha V-antibody, or antigen-binding portion thereof, and at least one bispecific or multispecific molecule of the invention, are also within the scope of the invention.

In yet another aspect of the invention, the human anti-alpha V antibodies are derivatized, linked to or co-expressed with another functional molecule, e.g., another peptide or protein (e.g., an Fab' fragment). For example, an antibody or antigen-binding portion of the invention can be functionally linked (e.g., by chemical coupling, genetic fusion, noncovalent association or otherwise) to one or more other molecular entities, such as another antibody (e.g., to produce a bispecific or a multispecific antibody), a cytotoxin, a cellular ligand or an antigen. Accordingly, present invention encompasses a large variety of antibody conjugates, bi- and multispecific molecules, and fusion proteins, all of which bind to alpha V expressing cells and which target other molecules to the cells, or which bind to alpha V and to other molecules or cells.

Alternatively, human antibodies of the invention can be co-administered with such therapeutic and cytotoxic agents, but not linked to them. They can be coadministered simultaneously with such agents (e.g., in a single composition or separately) or can be administered before or after administration of such agents. Such agents can include chemotherapeutic agents, such as dacarbazine, doxorubicin (adriamycin), cisplatin, bleomycin sulfate, carmustine, chlorambucil, cyclophosphamide hydroxyurea and combinations thereof. Human antibodies of the invention also can be administered in conjunction with radiation therapy.

In yet another embodiment, the present invention provides a method for inhibiting the proliferation and/or growth of a cell expressing alpha V integrin, and/or inducing killing of a cell expressing alpha V integrin, by contacting the cells with (e.g., administering to a subject) one or more human antibodies of the invention and/or related therapeutic compositions, derivatives etc. containing the antibodies as described above. In a particular embodiment, the method comprises contacting cells expressing alpha V integrin either in vitro or in vivo with one or a combination of human anti-alpha V antibodies of the invention in the presence of a human effector cell. The method can be employed in culture, e.g. in vitro or ex vivo (e.g., cultures comprising cells expressing alpha V and effector cells). For example, a sample containing cells expressing alpha V and effector cells can be cultured in vitro, and combined with an antibody of the invention.

Alternatively, the method can be performed in a subject, e.g., as part of an in vivo (e.g., therapeutic or prophylactic) protocol. For use in in vivo treatment and prevention of alpha V mediated diseases, human antibodies of the present invention are administered to patients (e.g., human subjects) at therapeutically effective dosages (e.g., to inhibit, eliminate or prevent growth of cells expressing alpha V or to inhibit angiogenesis and thus inhibit the growth of cells where growth is mediated by angiogenesis) using any suitable route of administration for antibody-based clinical products as are well known in the art, such as by injection or infusion.

Accordingly, human antibodies of the present invention can be used to treat and/or prevent a variety of alpha V integrin mediated diseases by administering a suitable dosage (or series of dosages) of the antibodies to patients suffering from such diseases. Exemplary diseases that can be treated (e.g., ameliorated) or prevented using the methods and compositions of the invention include, but are not limited to, cancers, such as metastatic melanoma, prostate cancer, colon cancer, and renal carcinoma.

In a particular embodiment of the invention, the patient can be additionally treated with a chemotherapeutic agent, radiation, or an agent that modulates, e.g., enhances, the expression or activity of an Fc receptor, such as a cytokine. Typical cytokines for administration during treatment include granulocyte colony-stimulating fact or (G-CSF), granulocytemacrophage colony-stimulating factor (GM-CSF), interferon-y (IFN-y), and tumor necrosis factor (TNF). Typical therapeutic agents include, among others, anti-neoplastic agents such as dacarbazine, doxorubicin (adriamycin), cisplatin, bleomycin sulfate, carmustine, chlorambucil, cyclophosphamide, and hydroxyurea.

In yet another aspect, the present invention provides a transgenic nonhuman animal, such as a transgenic mouse (also referred to herein as a "HuMAb mouse"), which expresses a fully human monoclonal antibody that binds to alpha V. In a particular embodiment, the transgenic nonhuman animal is a transgenic mouse having a genome comprising a human heavy chain transgene and a human light chain transgene encoding all or a portion of an anti-alpha V antibody of the invention. To generate human anti-alpha V antibodies, the transgenic nonhuman animal can be immunized with a purified or enriched preparation of alpha V antigen and/or cells expressing alpha V. Preferably, the transgenic nonhuman animal, e.g., the transgenic mouse, is capable of producing multiple isotypes of human monoclonal antibodies to Alpha V (e.g., IgG, IgA and/or IgM) by undergoing V-D-J recombination and isotype switching. Isotype switching may occur by, e.g., classical or non-classical isotype switching.

Accordingly, in another embodiment, the invention provides isolated cells derived from a transgenic nonhuman animal as described above, e.g., a transgenic mouse, which express human anti-alpha V antibodies. The isolated B-cells can then be immortalized by fusion to an immortalized cell to provide a source (e.g., a hybridoma) of human anti-alpha V antibodies. Such hybridomas (i. e., which produce human anti-ALPHA V antibodies) are also included within the scope of the invention.

As exemplified herein, human anti-alpha V antibodies can be obtained directly from hybridomas which express the antibody, or can be cloned and recombinantly expressed in a host cell, such as a transfectoma (e.g., a transfectoma consisting of immortalized CHO cells or lymphocytic cells). Accordingly, the present invention provides methods for producing human monoclonal antibodies which bind to human alpha V. In a particular embodiment, the method includes immunizing a transgenic nonhuman animal, e.g., a transgenic mouse, as previously described (e.g., having a genome comprising a human heavy chain transgene and a human light chain transgene encoding all or a portion of an anti-alpha V antibody), with a purified or enriched preparation of human alpha V antigen and/or cells expressing human alpha V. B cells (e.g., splenic B cells) of the animal are then obtained and fused with myeloma cells to form immortal, hybridoma cells that secrete human monoclonal antibodies against alpha V.

The present invention further provides at least one anti-alpha-V subunit antibody method or composition, for diagnosing at least one alpha-V subunit related condition in a cell, tissue, organ, animal or patient and/or, prior to, subsequent to, or during a related condition, as known in the art and/or as described herein.

The present invention further provides at least one alpha-V subunit anti-idiotype antibody to at least one alpha-V subunit antibody of the present invention. The anti-idiotype antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that can be incorporated into an antibody of the present invention. An anti-idiotype antibody of the invention can include or be derived from any mammal, such as but not limited to a human, a mouse, a rabbit, a rat, a rodent, a primate, and the like.

The present invention provides, in one aspect, isolated nucleic acid molecules comprising, complementary, or hybridizing to, a polynucleotide encoding at least one alpha-V subunit anti-idiotype antibody, comprising at least one specified sequence, domain, portion or variant thereof. The present invention further provides recombinant vectors comprising said alpha-V subunit anti-idiotype antibody encoding nucleic acid molecules, host cells containing such nucleic acids and/or recombinant vectors, as well as methods of making and/or using such anti-idiotype antibody nucleic acids, vectors and/or host cells.

Figure 5A:
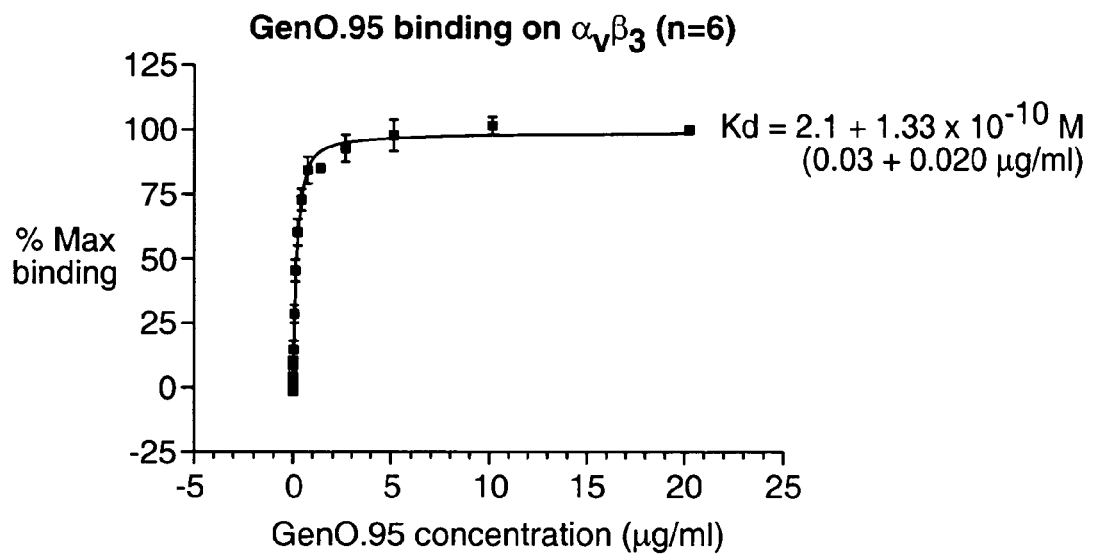
Figure 5B:
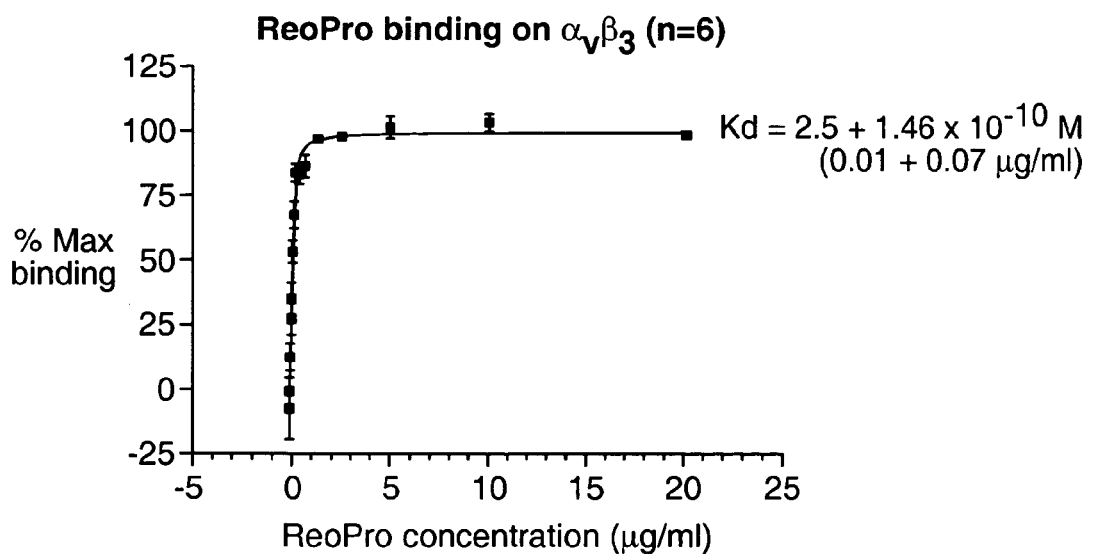

FIGS. 5A–B shows a graph of saturation binding curve of CNTO 95 (FIG. 5A) and abciximab (an anti-gpIIb/IIIa/αvB3 antibody) (FIG. 5B) on αvβ3 coated plates.

Figure 6A:
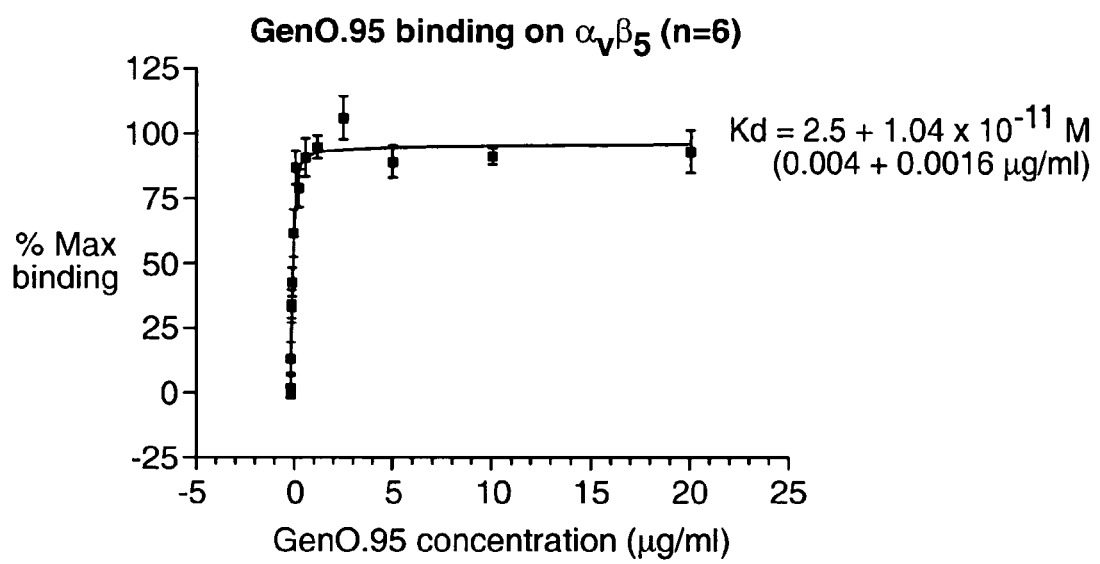
Figure 6B:
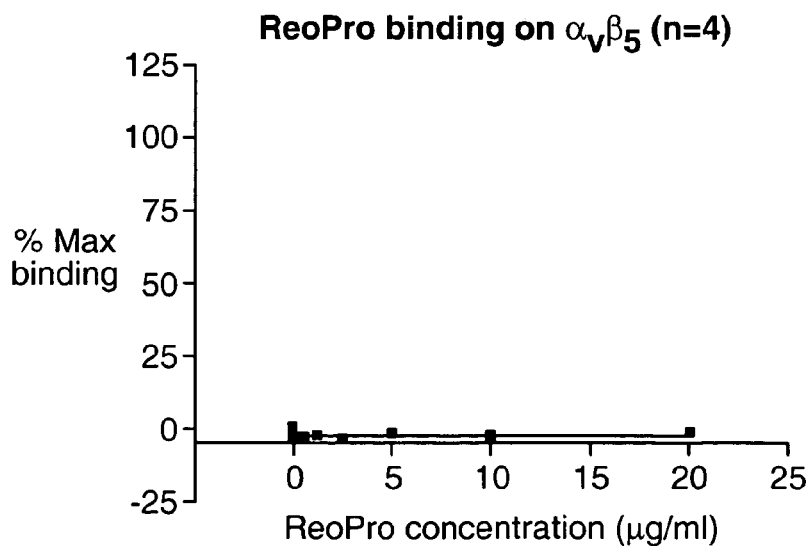

FIGS. 6A–B shows a graph of saturation binding curve of CNTO 95 (FIG. 5A) and abciximab (FIG. 5B) on αvβ5 coated plates.

Figure 7A:
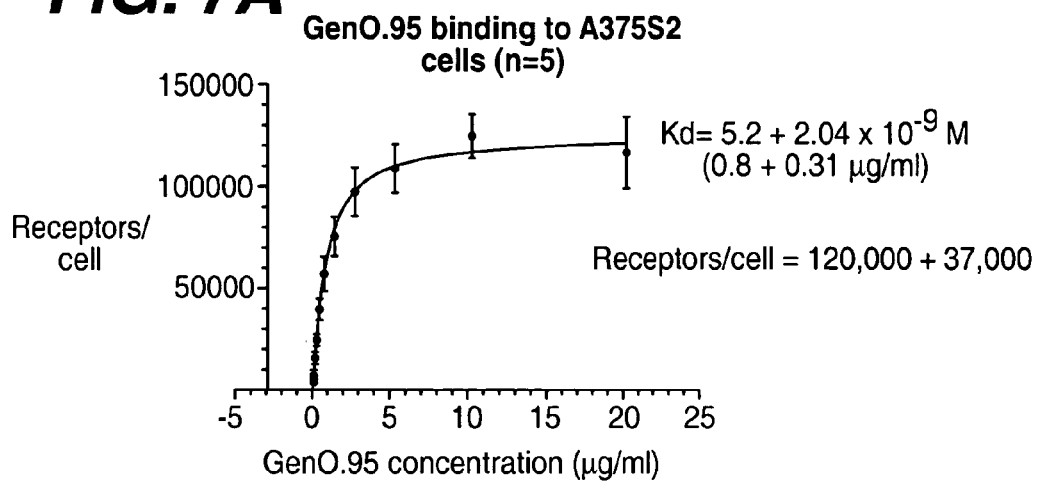
Figure 7B:
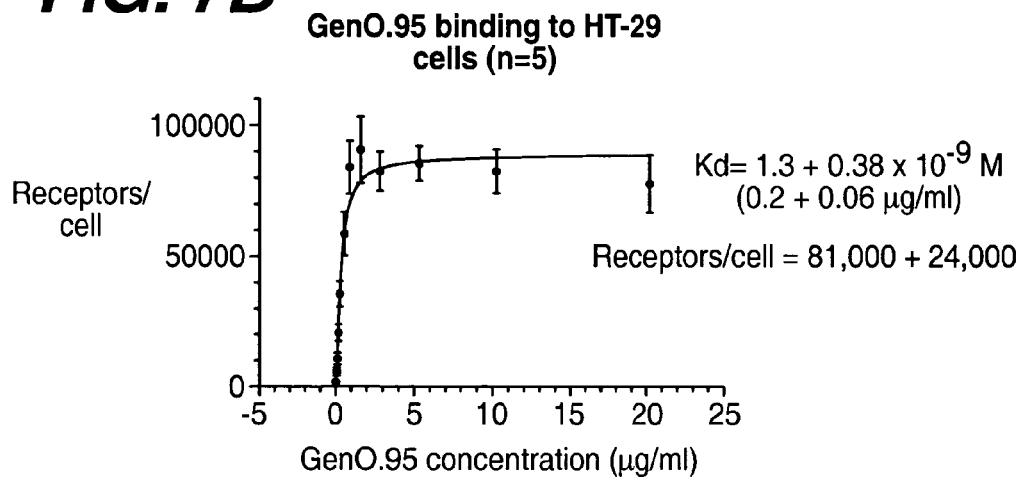
Figure 7C:
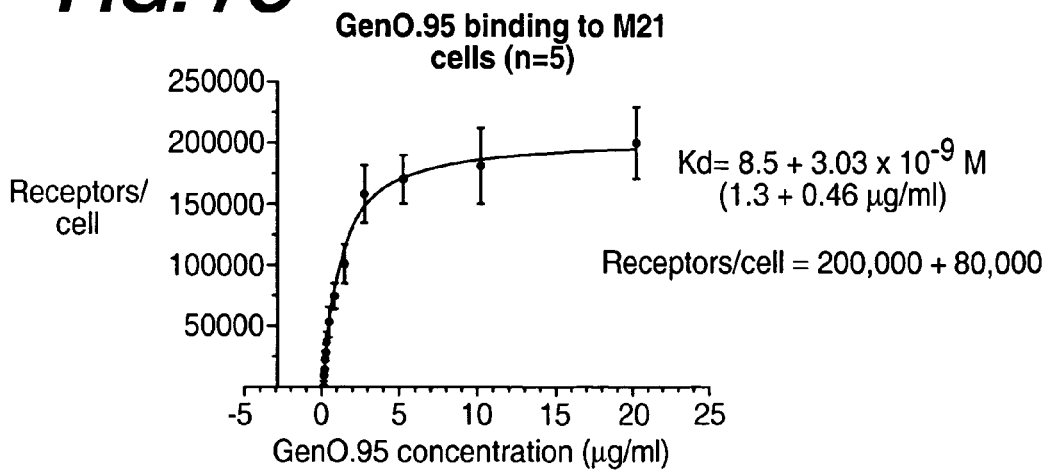

FIGS. 7A–C shows saturation binding curves with graphs binding to (FIG. 7A): A375S2; (FIG. 7B): HT-29; (FIG. 7C): M21. Cells were plated 2 days prior to experiment, and $1\times10^5$ cells/well at the time of study. 125-I CNTO 95 (1 μCi/μg) was added in 1% growth media and incubated on cells for 1.5 h, 37° C. Nonspecific binding was determined using 100× cold mAb in media. Cells were washed 3× and counted for bound radioactivity. Each curve represents 4–5 separate studies, and each data point in an experiment was the mean of triplicate samples.

Figure 8A:
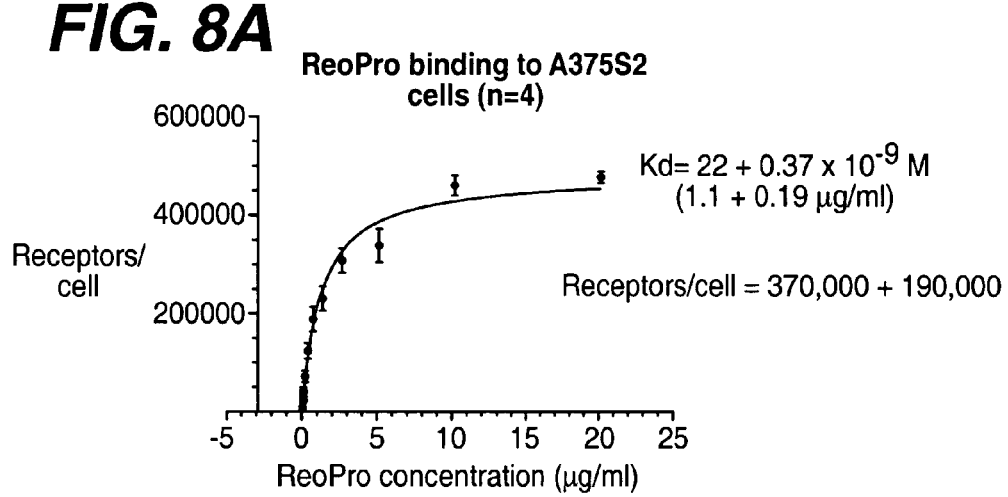
Figure 8B:
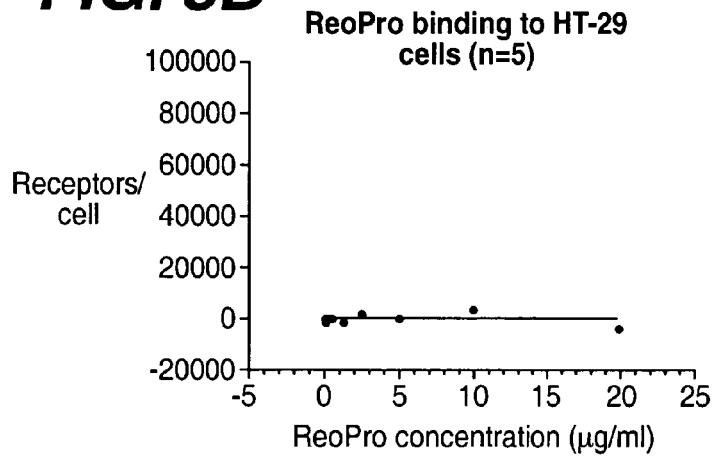
Figure 8C:
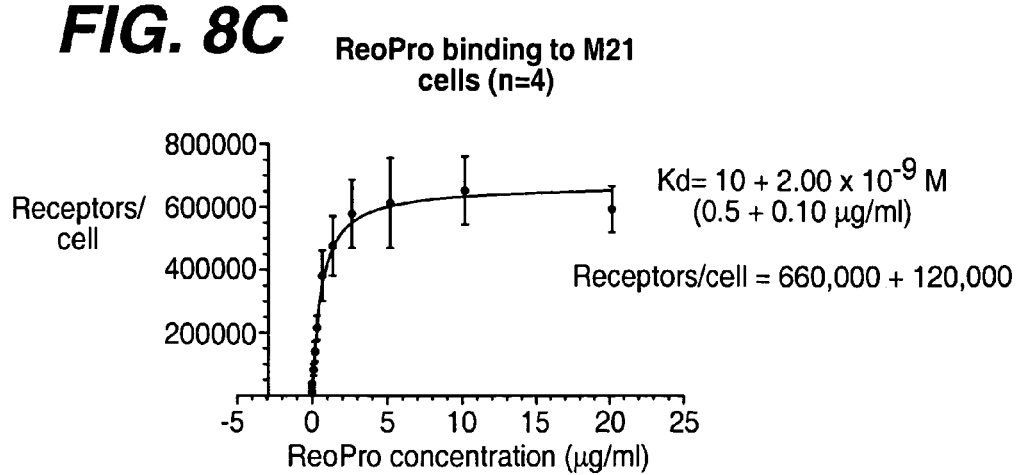

FIGS. 8A–C shows saturation binding curves with graphs binding to (FIG. 8A): A375S2; (FIG. 8B): HT-29; (FIG. 8C): M21. Cells were plated 2 days prior to the experiment, and $1\times10^5$ cells/well at the time of study. 125-I abciximab(1 μCi/μg) was added in 1% growth media and incubated on cells for 1.5 h, 37° C. Nonspecific binding was determined using 100× cold mAb in media. Cells were washed 3× and counted for bound radioactivity. Each curve represents 4–5 separate studies, and each data point in an experiment was the mean of triplicate samples.

Figure 9:
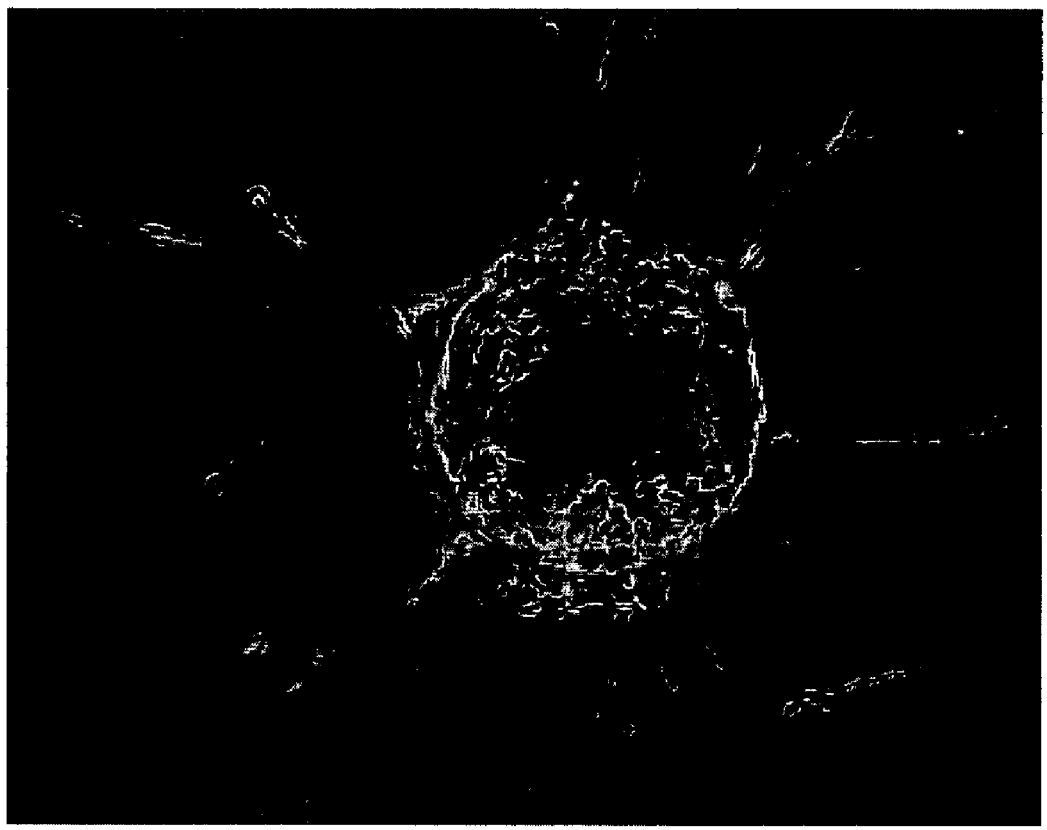

FIG. 9 shows a representation of microcapillary formation of endothelial cells from MC beads cultured in fibrin gels. Objective lens: 40×. The assay was performed as described in Methods of Example 4.

Figure 10:
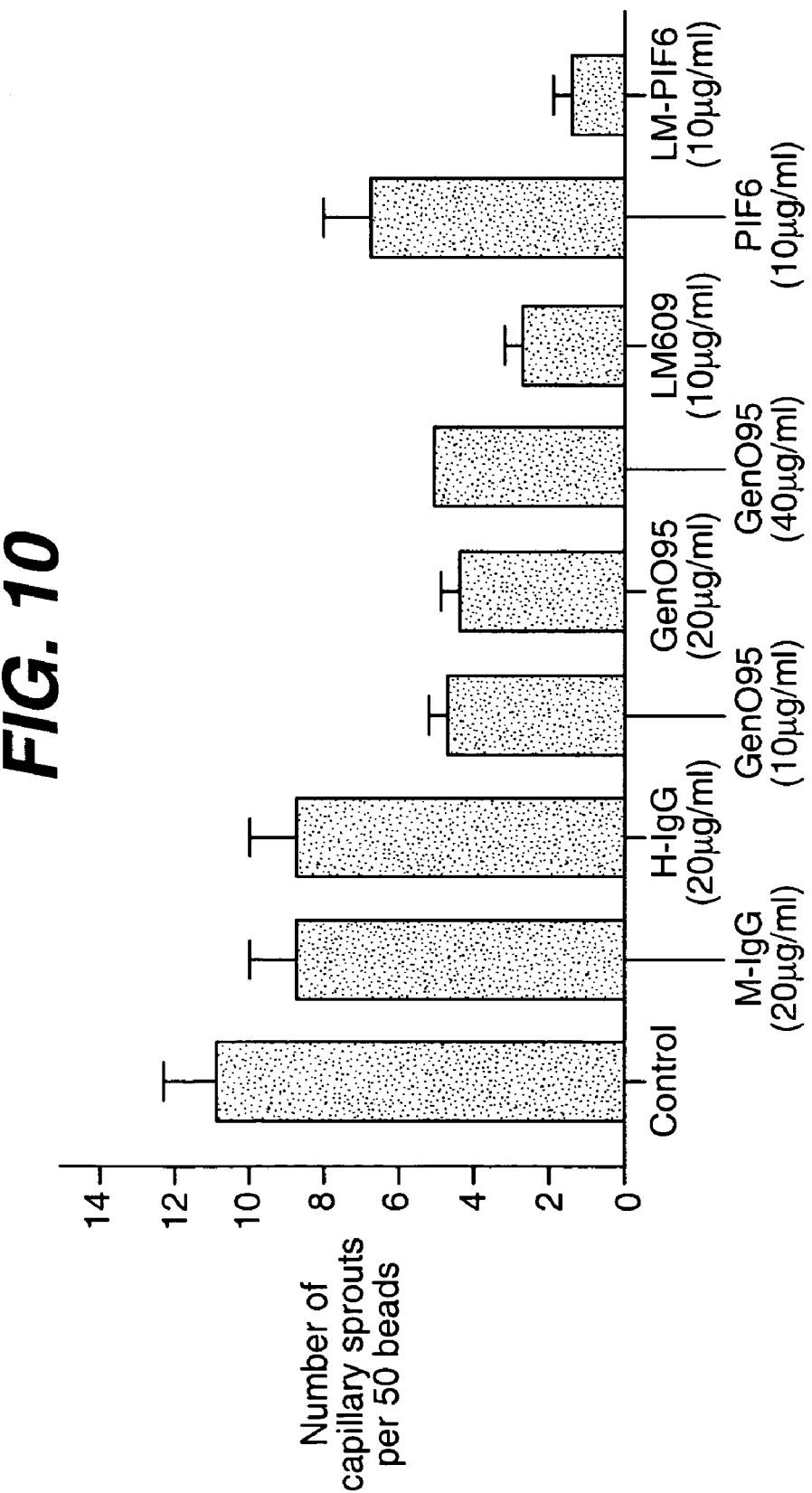

FIG. 10 shows a graph of quantification of capillary formation in a fibrin gel in media containing 30 ng/ml bFGF dissolved in 0.1% serum. The number of microcapillary sprouts were quantified as described in Methods of Example 4. Control indicates vehicle control, mouse (M) and human (H) IgG served as negative controls. LM-P1F6 is a combination of both LM609 and P1F6. Each bar represents the mean of 6 wells (+/−SD).

FIG. 11 shows a graph of quantification of capillary formation in a fibrin gel in complete media. The number of microcapillary sprouts were quantified as described in Methods of Example 4. Control indicates vehicle control. Mouse (m) and human (h)-IgG served as negative controls. LM-P1F6 is a combination of both LM609 and P1F6. Each bar represents the mean of 6 wells (+/−SD).

Figure 12A:
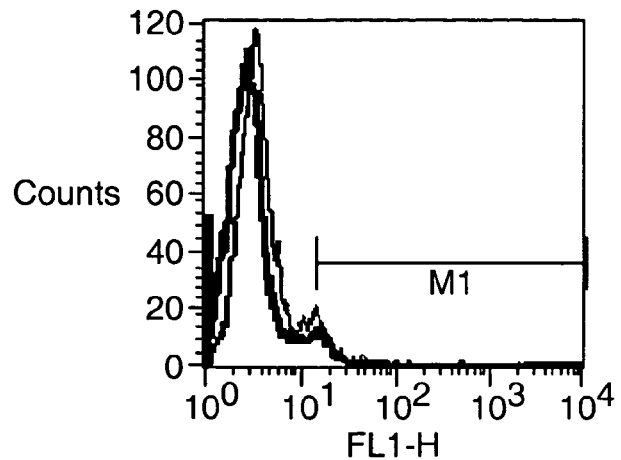
Figure 12B:
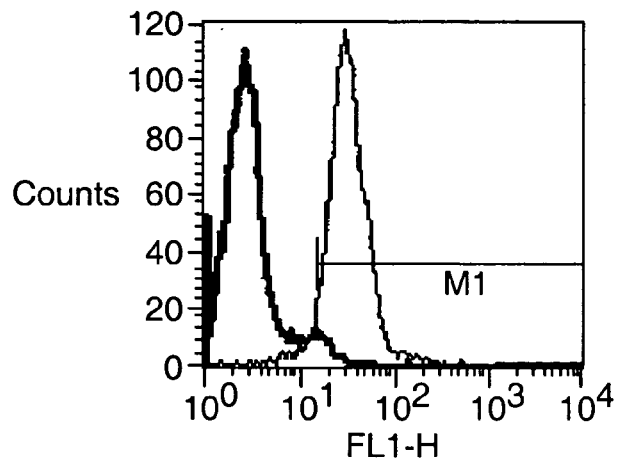
Figure 12C:
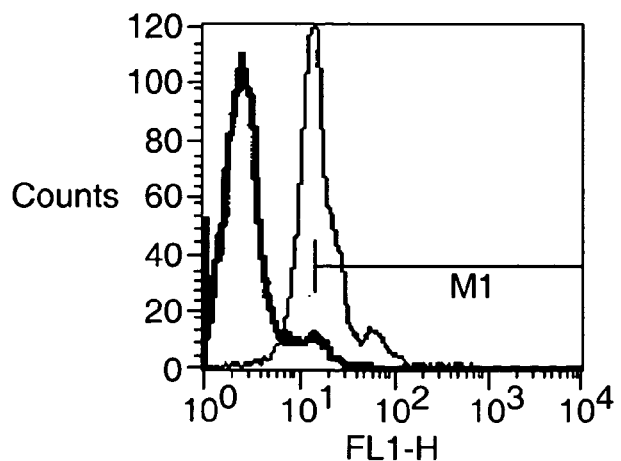
Figure 12D:
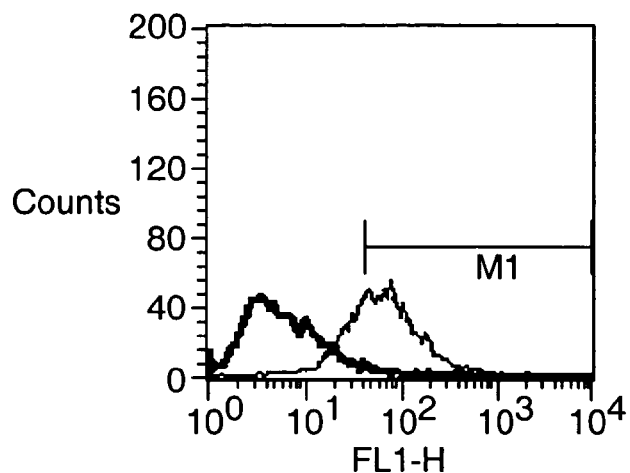
Figure 12E:
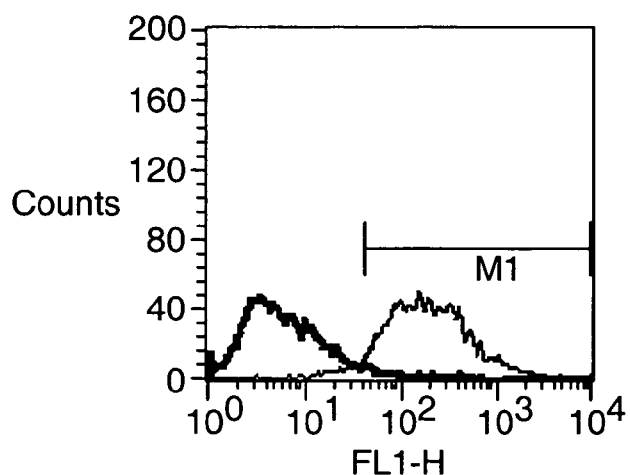
Figure 12F:
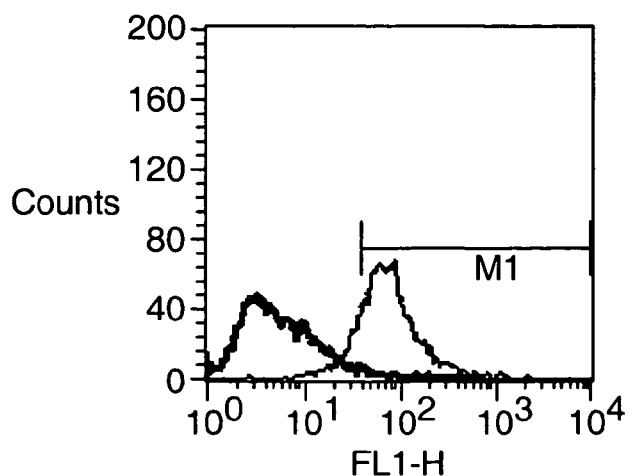
Figure 12G:
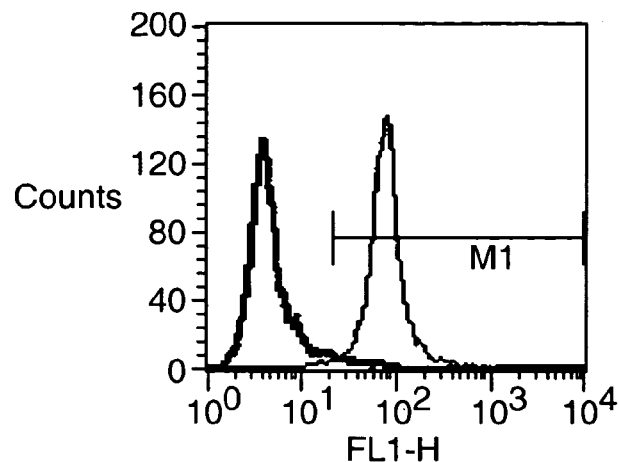
Figure 12H:
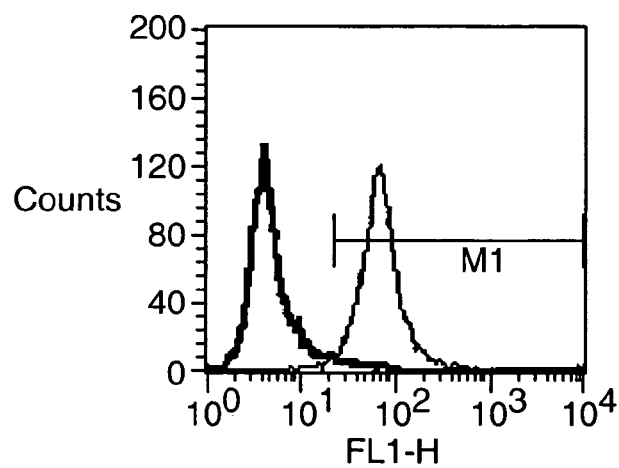
Figure 12:
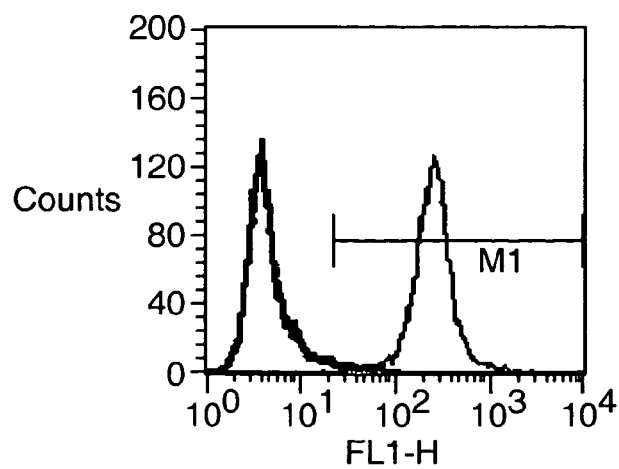

FIG. 12 HT29 cells (FIGS. 12A, B and C) express αvβ5, but not αvβ3 integrin on their surface. HUVEC (FIGS. 12D, E and F) and A375S.2 (FIGS. 12G, H and I) cells express αvβ5 and αvβ3 integrin on their surface. Tumor cells and endothelial cells were stained by immunofluorescence and analyzed by flow cytometry. The histogram on the left represents background fluorescence in the presence of isotype matched antibody. The histogram on the right indicates positive staining. A, D, G, LM609 (mAb directed to αvβ3, 10 μg/ml); B, E, H, PIF6 (mAb directed to αvβ5, 10 μg/ml); and C, F, I, GenO95 (10 μg/ml).

Figure 13:
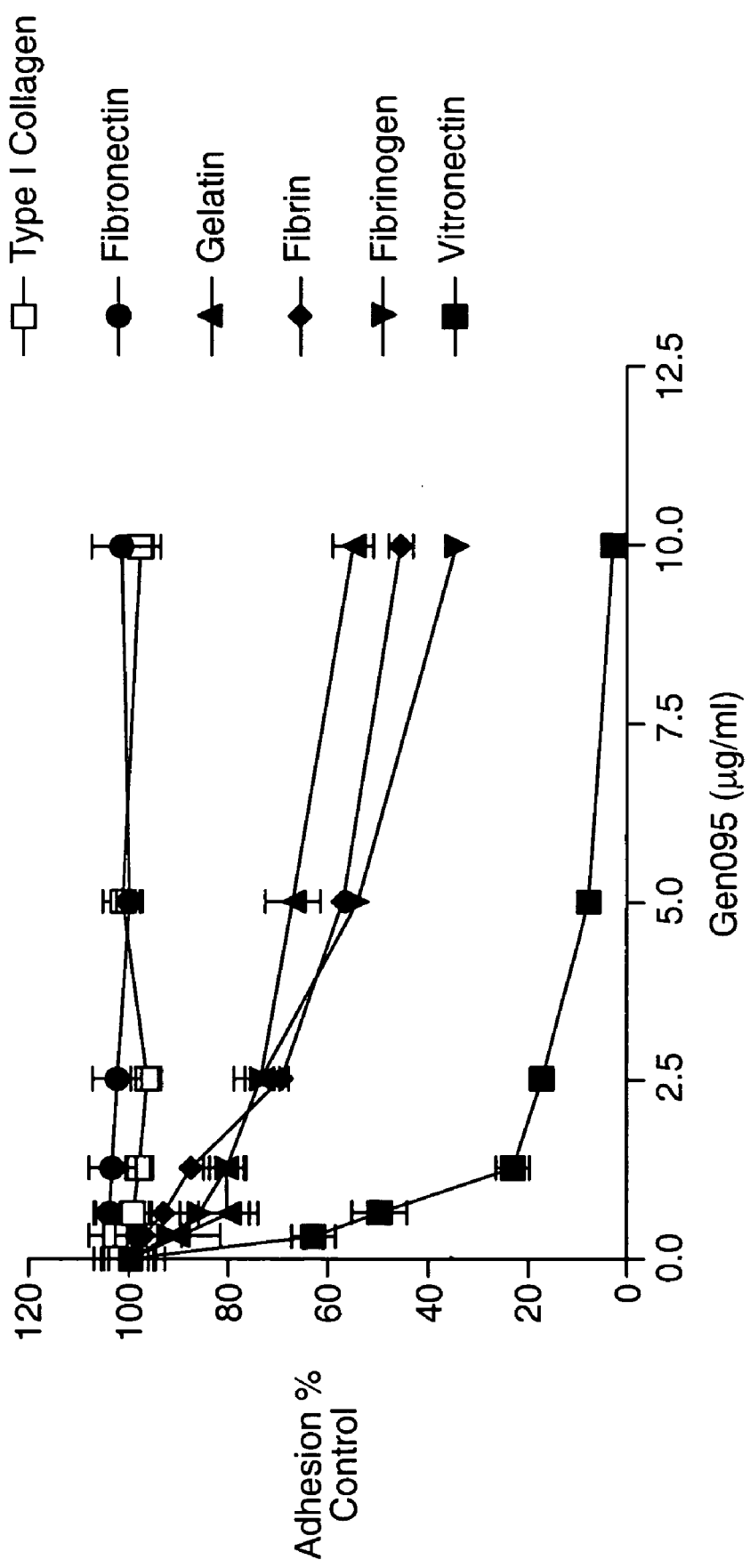

FIG. 13 Adhesion of HUVECS to matrix protein-coated plates. Adhesion assay was performed as described in Methods of Example 5. Plate was read on a fluorometer at 485–538 nm. Cell adhesion to BSA coated wells served as a negative control. In FIG. 13, the extent of cell adhesion in the presence of various concentrations of antibody was plotted as a percent of cell adhesion in the absence of antibody that was considered as 100%. Each data point is the mean of triplicate determinations (+/−SD).

Figure 14:
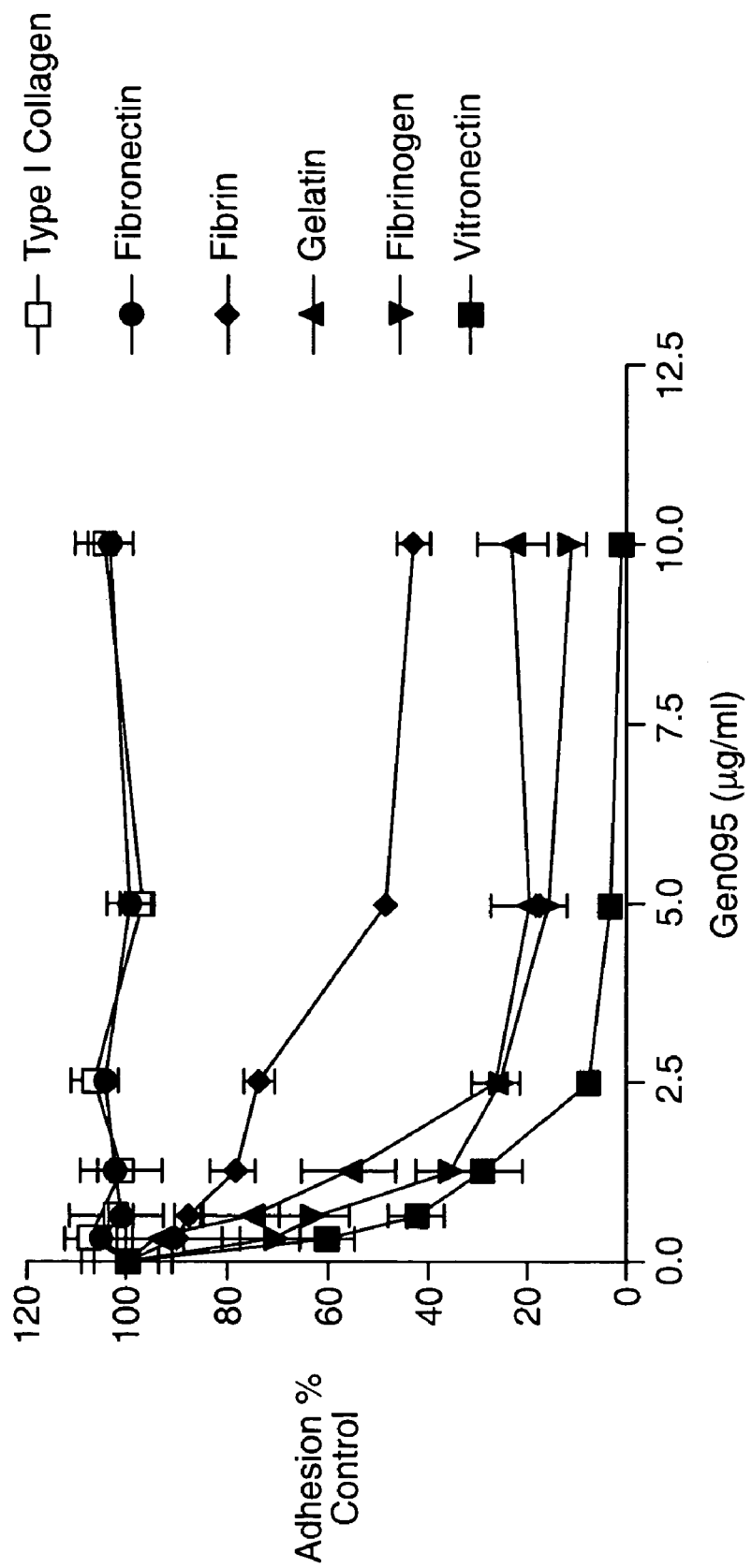

FIG. 14 Adhesion of human melanoma cells to matrix protein-coated plates. Adhesion assay was performed as described in Methods of Example 5. Cell adhesion to BSA coated wells served as a negative control. In FIG. 14 the extent of cell adhesion in the presence of various concentrations of antibody was plotted as a percent of cell adhesion in the absence of antibody that was considered as 100%. Each data point is the mean of triplicate determinations (+/−SD).

Figure 15:
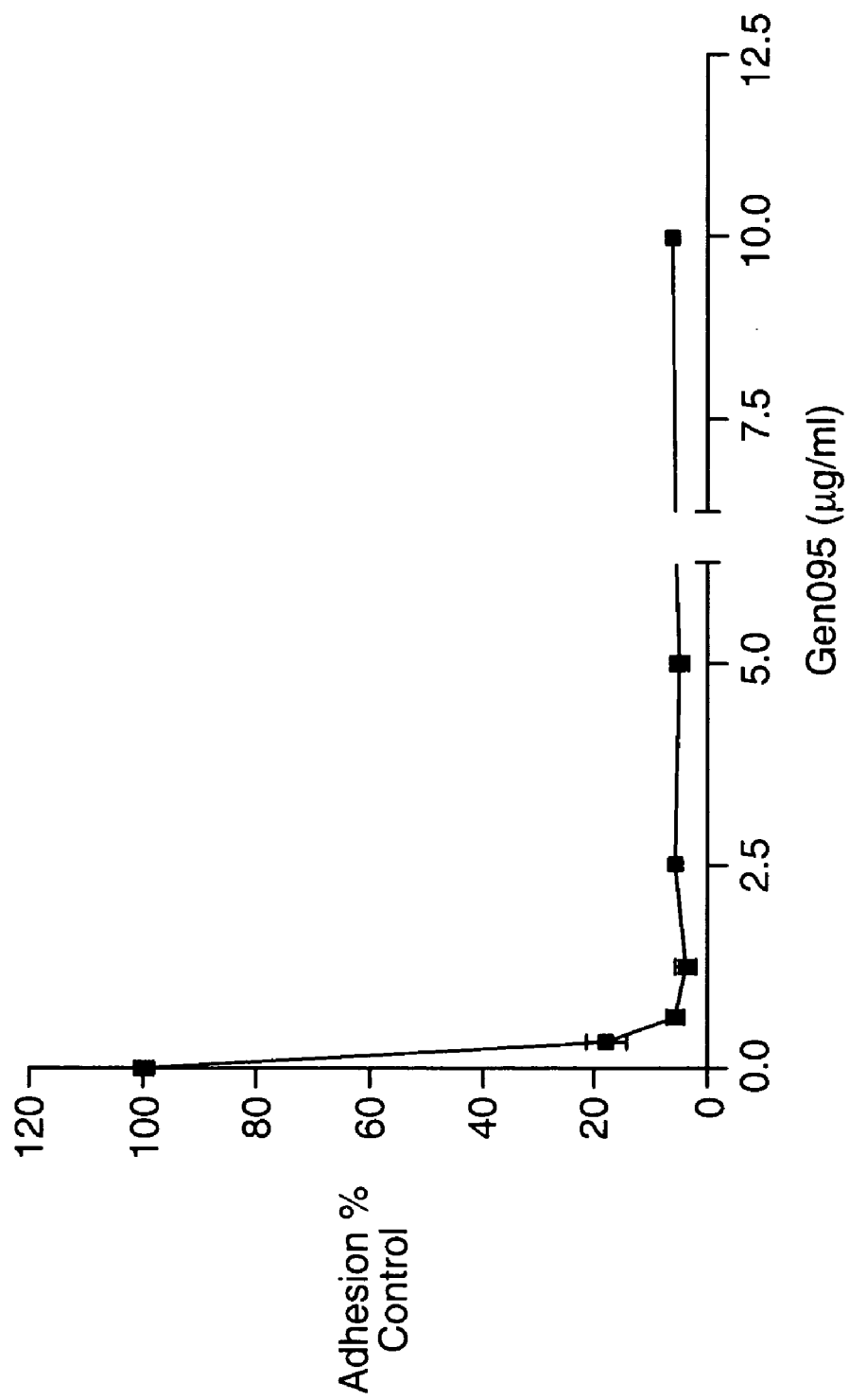

FIG. 15 Adhesion of human colon carcinoma HT29 cells to vitronectin. The adhesion assay was performed as described in the Examples. Cell adhesion to BSA coated wells served as a negative control. Data in FIG. 15 are plotted as percent of maximum binding (absence of antibody), and are the mean of triplicate determinations (+/−SD).

FIGS. 16A–D Migration of HUVECS toward 2 μg/ml vitronectin. The assay was performed as described in Methods and cells were allowed to migrate for 6 h. Photomicrographs are representative fields (10× objective lens) of cell migration in FIG. 16A, absence of antibody, (16B), CNTO 95 (5 μg/ml), (16C), CNTO 95 (40 μg/ml). FIG. 16D is graphical representation of cell migration in the presence of varying concentrations of GenO95. The data were normalized to percent of control (no antibody) which was considered as 100%, and each point is the mean of three transwell filters (+/−SD).

FIG. 17. Migration of HUVECS toward 2 μg/ml vitronectin in the presence of antibodies to αvβ3 and αvβ5. The migration assay was performed as described in Methods of Example 5, and cells were allowed to migrate for 6 hours. LM609 and P1F6 are mAbs directed to αvβ3 and αvβ5, respectively. The data shown in FIG. 17 were normalized to percent of control (no antibody) which was considered as 100%, and each bar is the mean of three transwell filters (+/−SD). BSA, mouse IgG and human IgG served as negative controls. LM609-PEF6 represents combinations of both antibodies. The antibodies and BSA were used at a concentration of 10 μg/ml.

Figure 18A:
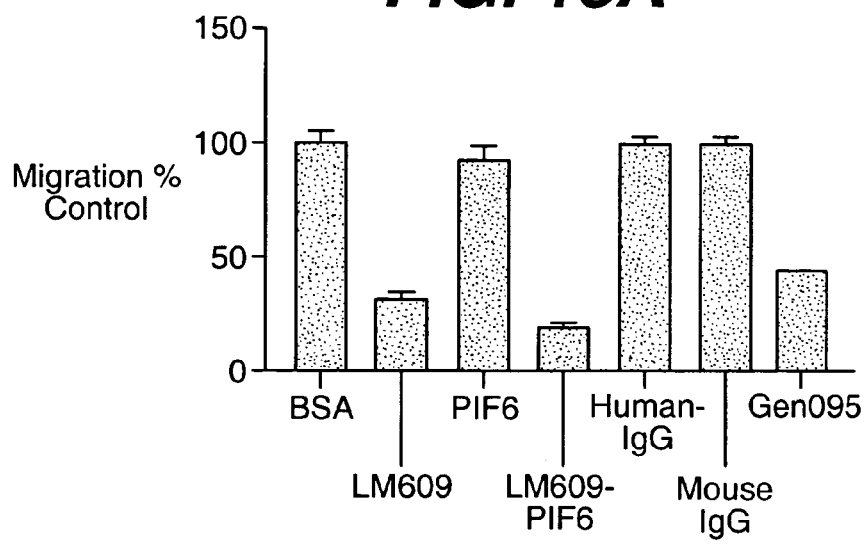
Figure 18B:
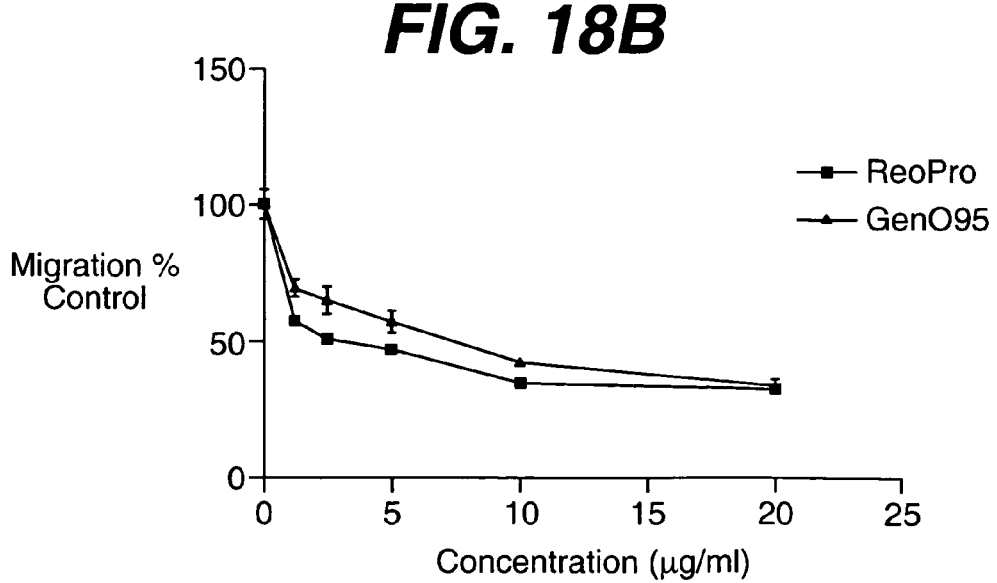
Figure 18C:
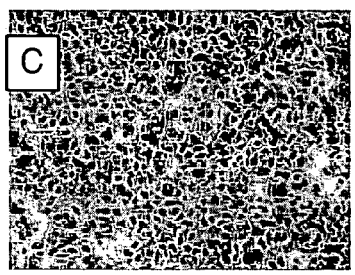
Figure 18D:
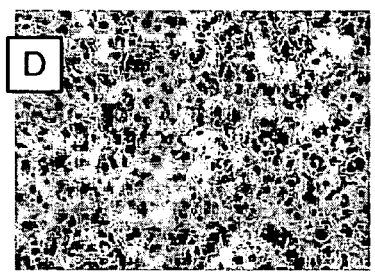
Figure 18E:
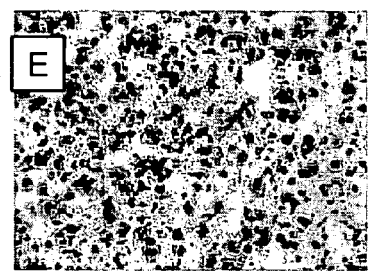

FIGS. 18A–E Migration of HUVECS towards 2% FBS. Migration assay was allowed to proceed for 4 h and the data was captured as described in the Methods of Example 5. FIG. 18(A) is a graphical representation of cell migration in the presence of LM609, P1F6, combination of LM609+P1F6, isotype matched control antibodies (human and mouse). The antibodies and proteins were used at a concentration of 10 μg/ml. FIG. 18(B) is a graphical representation of cell migration in the presence of ReoPro and GenO95. Photomicrographs are representative fields (10× objective lens) of cell migration in FIG. 18(C), the absence of antibody, FIG. 18(D), GenO95 (5 μg/ml), and FIG. 18(E), GenO95 (20 μg/ml). The data were normalized to percent of control (no antibody) which was considered as 100%, and each point is the mean of three transwell filters (+/−SD).

Figure 19A:
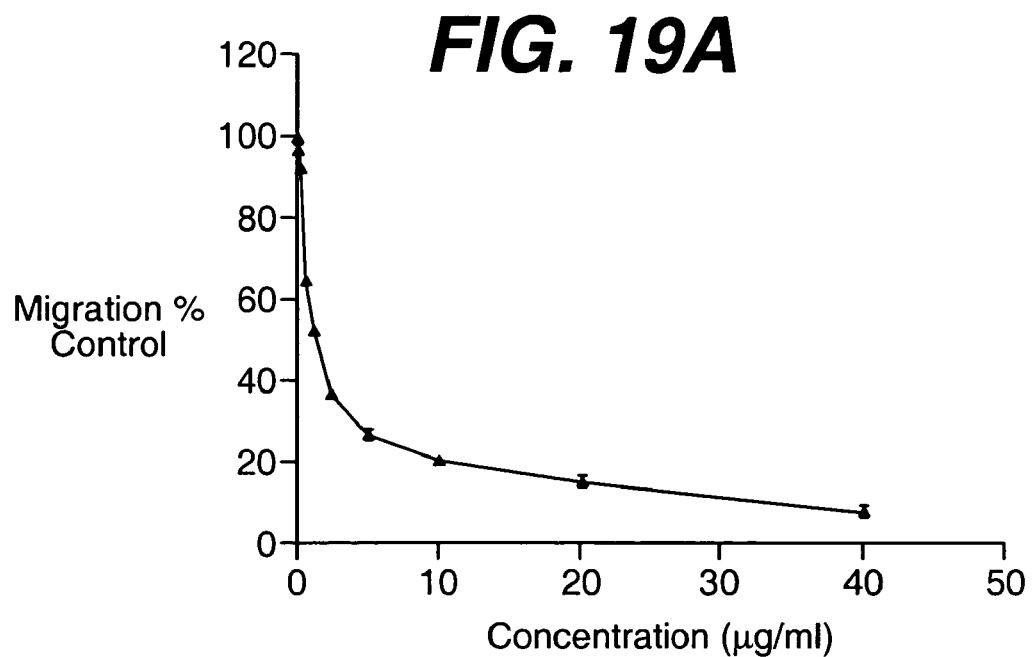
Figure 19B:
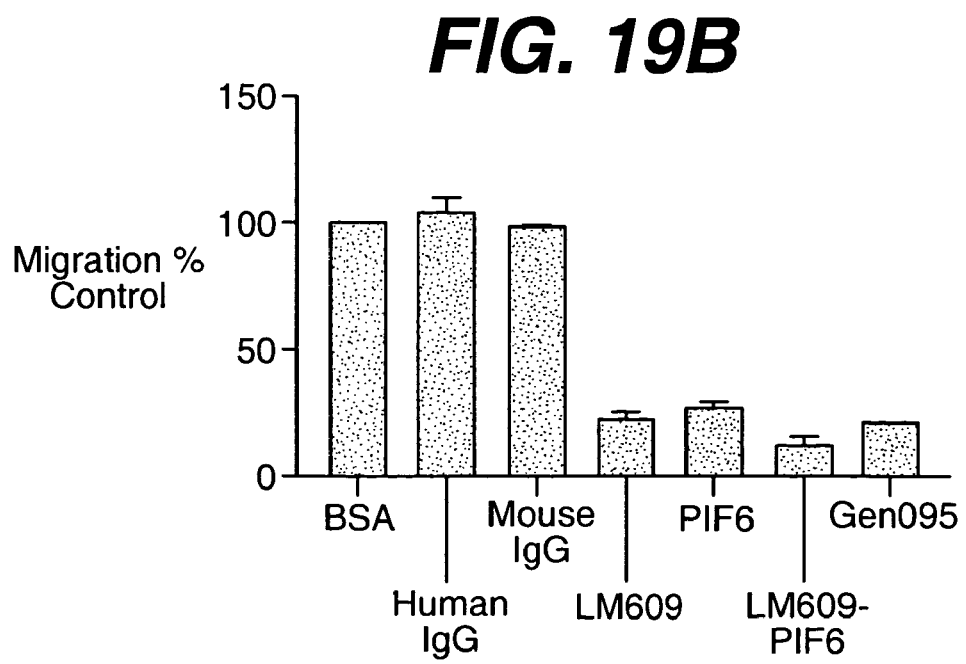

FIGS. 19A–E. Migration of A375S.2 cells toward 10% FBS. Migration assay was allowed to proceed for 4 h and the data was captured as described in the Methods of Example 5. Antibodies were used at a concentration of 10 μg/ml. FIG. 19(A) is a graphical representation of cell migration in the presence of varying concentrations of GenO95. FIG. 19(B) is a graphical representation of cell migration in the presence of LM609, P1F6, combination of LM609+P1F6, isotype matched control antibodies (human and mouse). The data were normalized to percent of control, which was considered as 100%, and each point is the mean of three transwell filters (+/−SD). Photomicro-graphs are representative fields (10× objective lens) of cell migration in FIG. 19(C), absence of antibody, FIG. 19(D), GenO95 (5 μg/ml), and FIG. 19(E), GenO95 (20 μg/ml).

Figure 20E:
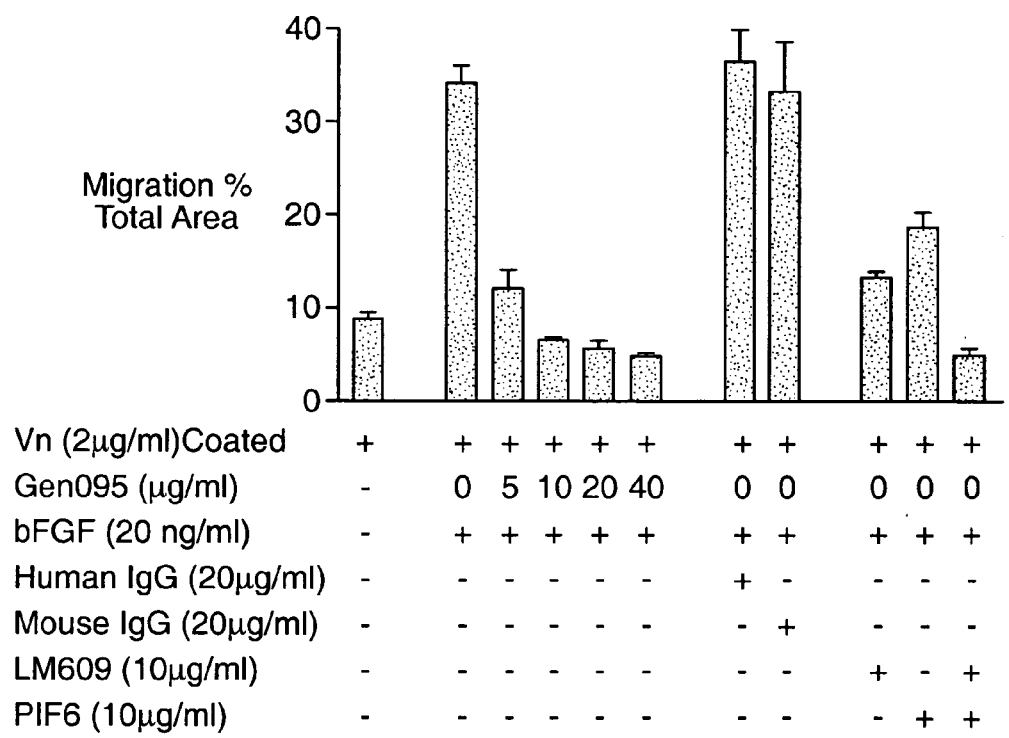
Figure 21A:
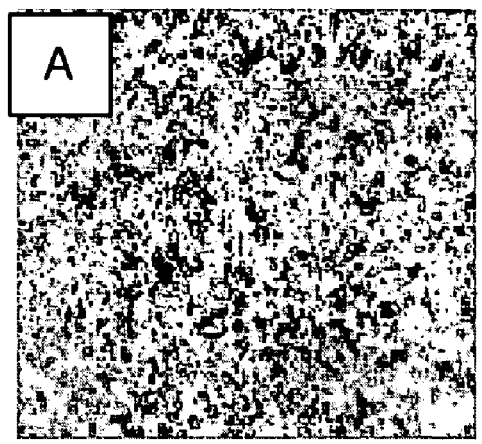
Figure 21B:
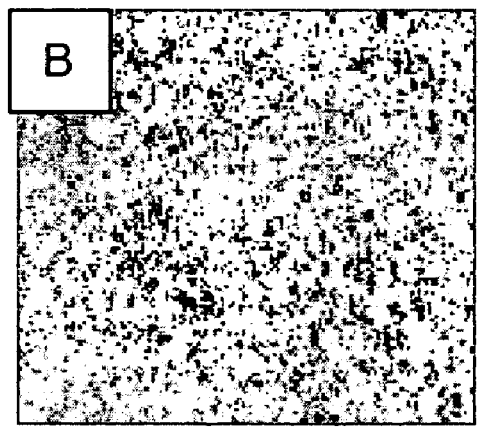
Figure 21C:
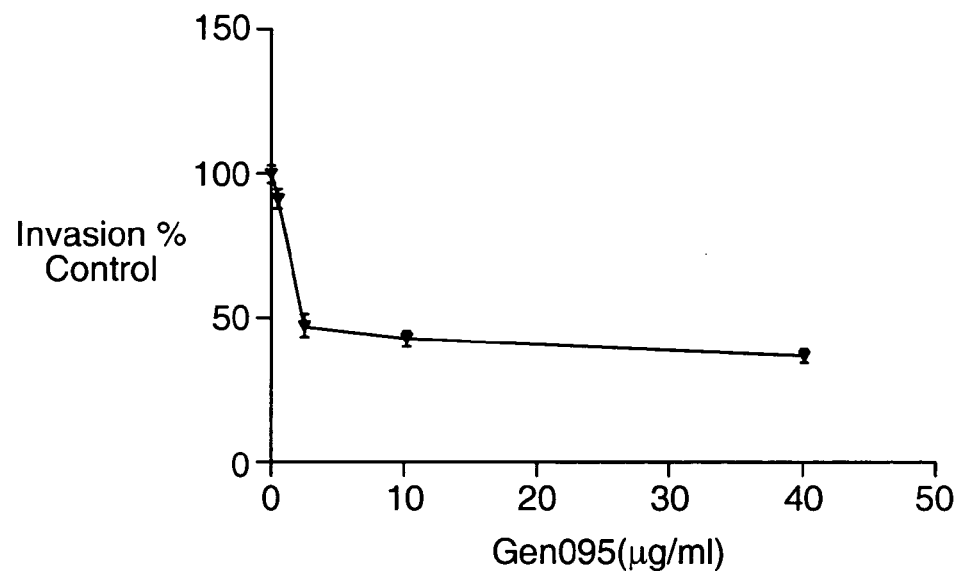
Figure 21D:
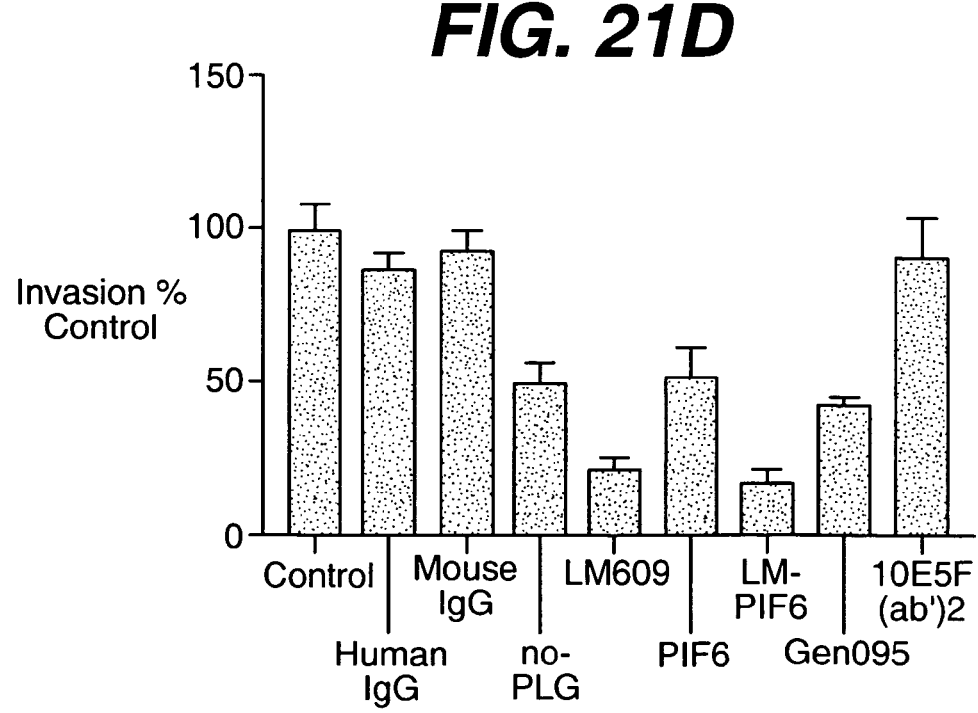

FIGS. 20A–E Migration of HUVECS towards vitronectin in the presence of bFGF. The undersides of migration chamber filters were coated with 2 μg/ml vitronectin, and the assay was performed as described in the Methods of Example 5. Cells were allowed to migrate for 6 h. In FIGS. 20A–E, each data point is the mean of 3 transwell filters (+/−SD). FIG. 20(A), bFGF; FIG. 20(B), CNTO 95 (5 μg/ml); FIG. 20(C), CNTO 95 (40 μg/ml); FIG. 20(D), no-bFGF. FIG. 20(E), Inhibition of cell migration in the presence of various antibodies is shown graphically.

FIGS. 21A–D. Invasion of A375S.2 cells through a fibrin gel (5 mg/ml). Invasion assay was allowed to proceed for 24 h and data was captured as decribed in the Methods of Example 5. Photomicrographs are representative fields (4× objective lens) of cell invasion in FIG. 21(A) the absence of antibodies, FIG. 21(B) CNTO 95 (10 μg/ml), FIGS. 21(C) and (D) are graphical representation of cell invasion in presence of CNTO 95, 10E5 F(ab')$_2$, LM609, P1F6, LM-PIF6 (LM609+P1F6), human and mouse IgGs (H-IgG and M-IgG). Graph FIG. 21(D): The concentration of all antibodies and proteins is 10 μg/ml. The data were normalized to percent of control (no antibody) which was considered as 100%, and each point is the mean of three transwell filters (+/−SD).

Figure 22A:
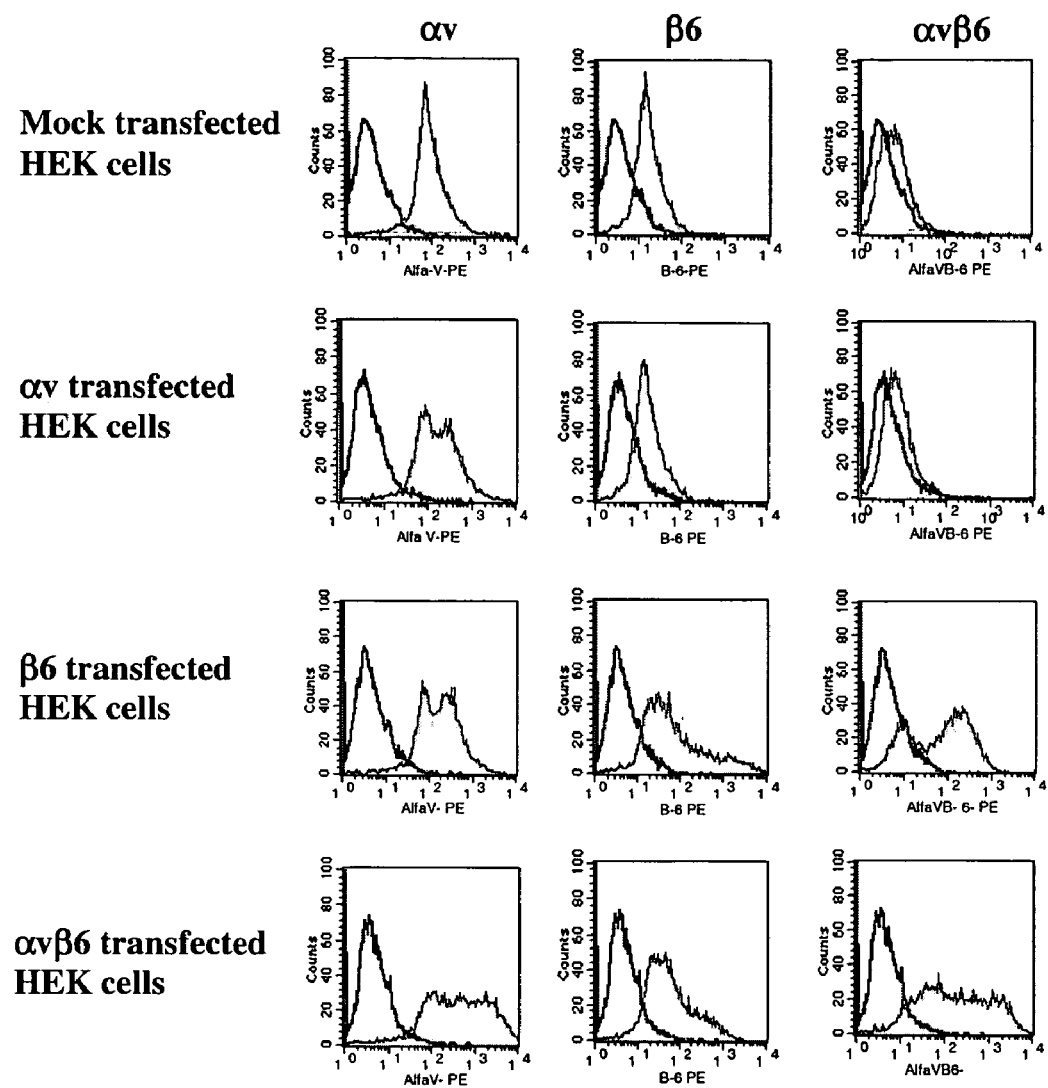

FIGS. 22A–D. are histograms from flow cytometric analysis of HEK cells transfected with various integrin DNA and immunoflurescently stained as noted. FIG. 22(A): cells stained with antibodies for specific subunits. FIG. 22(B): mock transfected and avb6 transfected cells were analyzed for expression of αvβ3, αvβ5, and β1 integrins. FIG. 22(C): HEK 293 cells were transfected with αV, β6, or αvβ6 cDNA and CNTO 95 binding measured. The vertical line serves as a reference marker and indicates the fluorescence intensity at which mock transfectants were <2% positive. FIG. 22(D): analysis of mock transfected (A, B, C) or αvβ6 transfected (C, D, E) HEK 293 cells for CNTO 95 immunoreactivity. Cells were stained with anti-avb6 (A, D) or CNTO 95 (B, E). Double staining was used to detect cells which were immunoreactive with both antibodies simultaneously (C, F). The upper-right quadrant in F indicates that cells which stained intensely for avb6 also stained intensely for CNTO 95.

Figure 23:
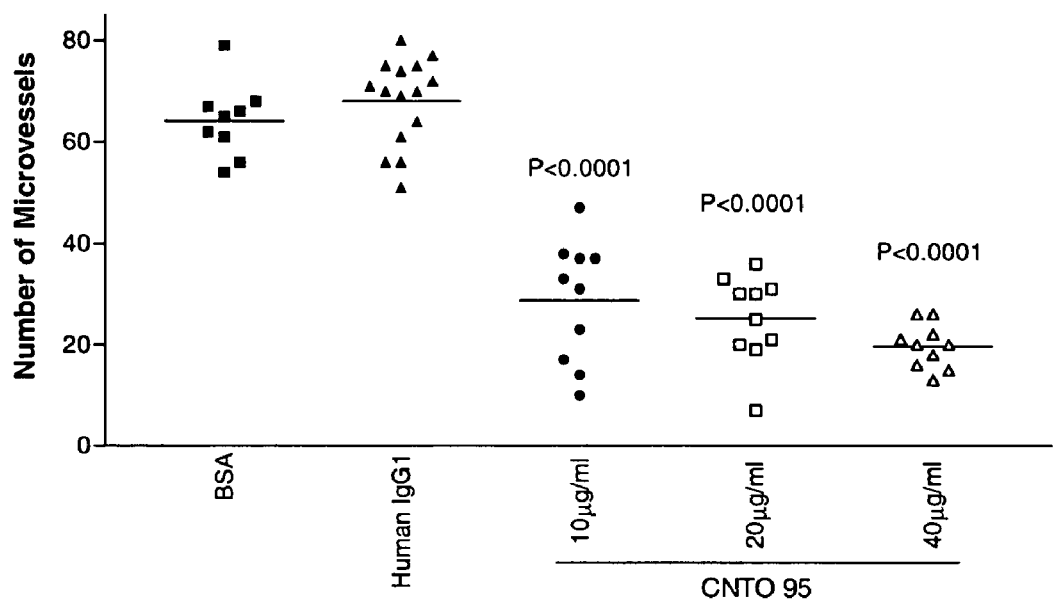

FIG. 23 is a graph showing the number of microvessels sprouting from rat aortic rings treated as described. BSA (20 ug/ml) and irrelevant human IgG (20 ug/ml) were used as negative controls. Data points represent one rat aorta, with mean values for each group indicated by lines. P values were determined by comparing the antibody-treated groups with the BSA-treated group using a two-tailed unpaired t-test.

Figure 24A:
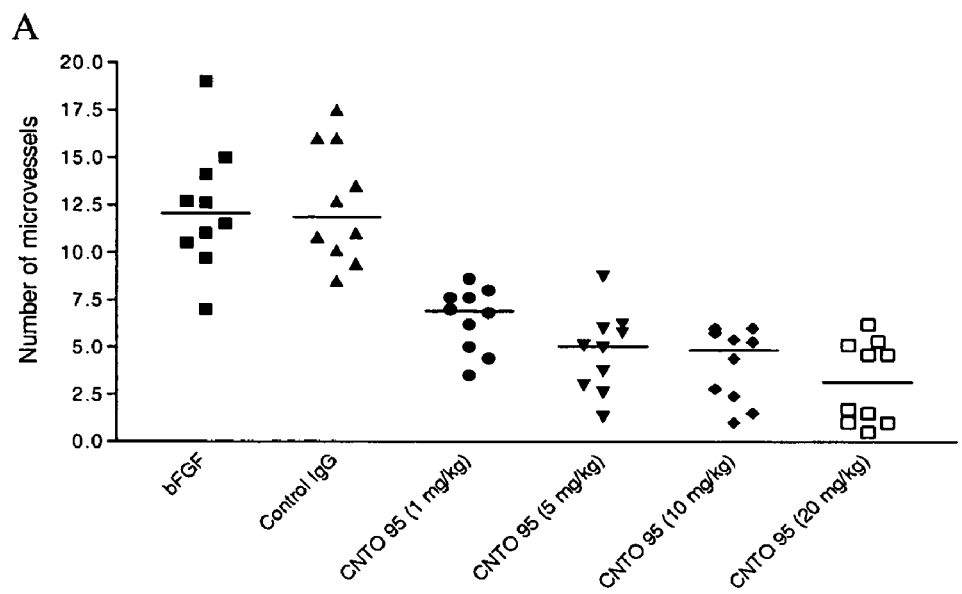
Figure 24B:
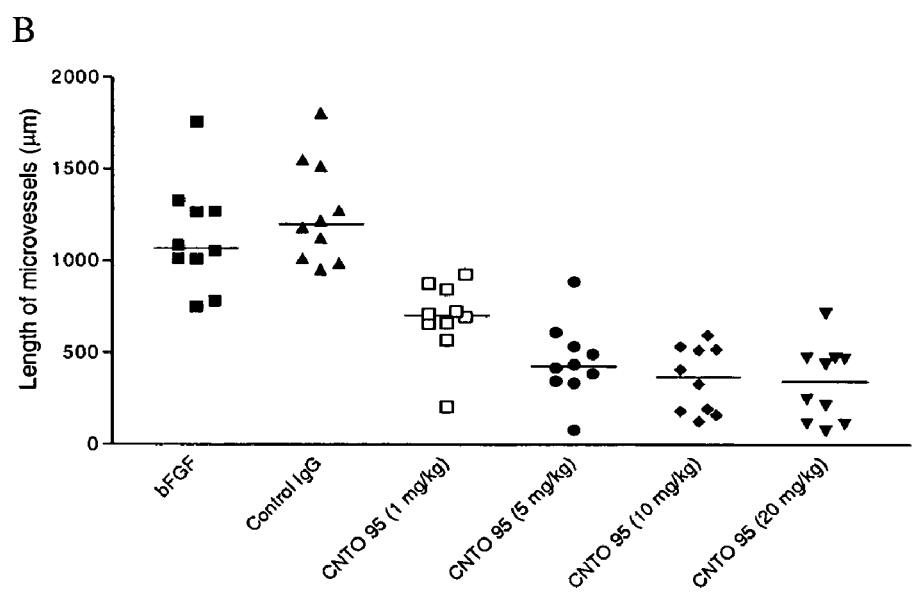

FIG. 24 are graphs of the data on length FIG. 24(A) and number FIG. 24(B) of blood vessels found in bFGF-impregnated Matrigel plugs in nude rats examined on day 7. Vessel number and length were assessed by microscopy (2×) aided by image analysis software (Phase 3 Image System). Each point represents average per view from one Matrigel sample (2 plugs/animal), the line represents the group mean. A two-tailed unpaired t-test indicated P<0.0001 for all four CNTO 95 dose groups compared to the control IgG group.

Figure 25A:
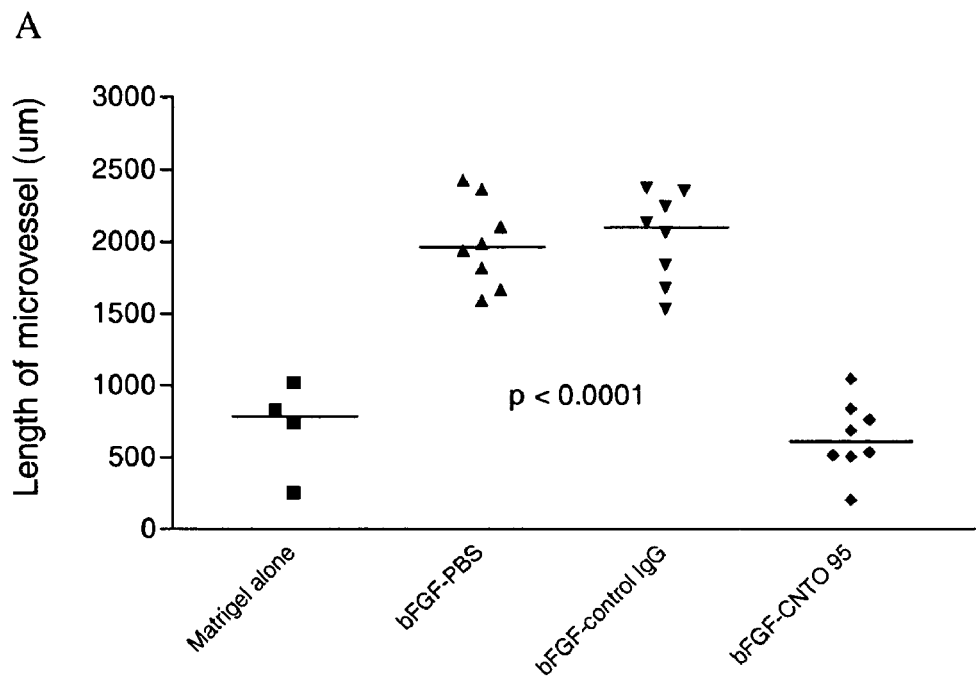
Figure 25B:
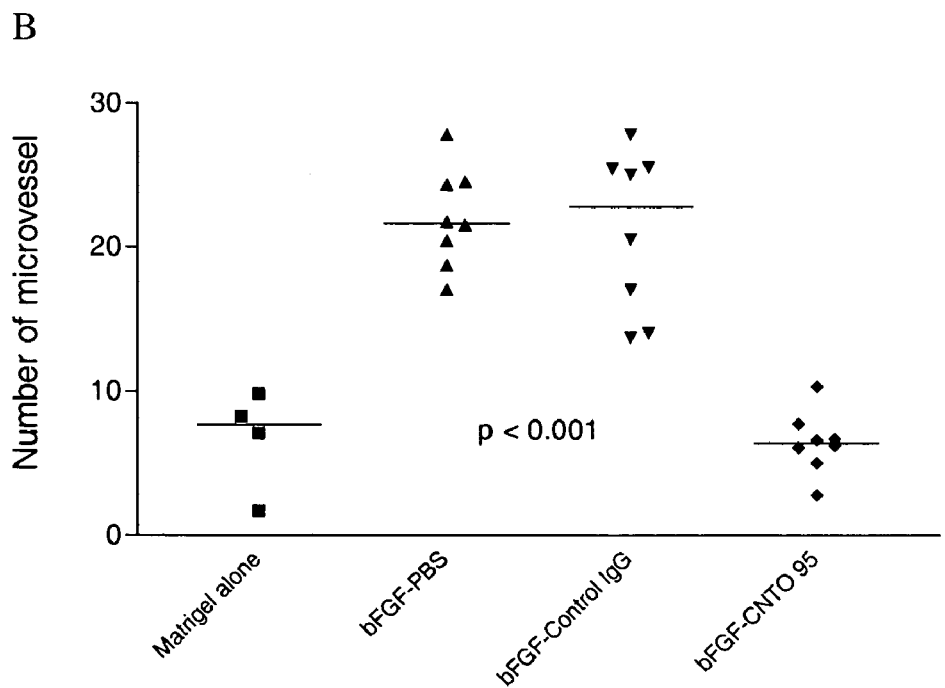
Figure 25C:
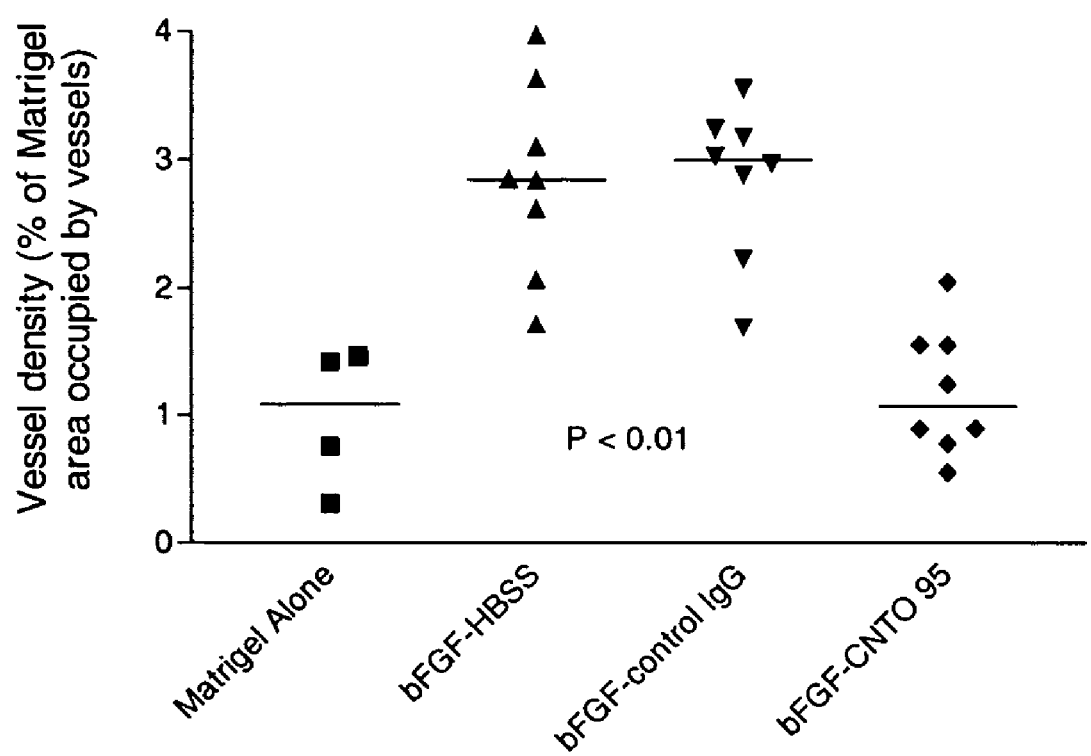

FIGS. 25A–C are graphs of the data on length FIG. (A), number FIG. (B) and density FIG. 25(C) of blood vessels found in bFGF-impregnated Matrigel plugs in monkeys examined on day 7. For FIG. 25(A) and FIG. 25(B) each point represents average per 2× field from one Matrigel sample (4 Matrigel plugs/animal). Horizontal lines indicate mean. Matrigel alone, bFGF-PBS, 5 ug/ml bFGF. bFGF-control IgG, 5 ug/ml bFGF, 10 ug/kg control IgG i.v. bFGF-CNTO 95, 5 ug/ml bFGF, 10 mg/kg CNTO 95 i.v. A two-tailed unpaired t-test analysis indicated P<0.001 for Matrigel alone and bFGF-CNTO 95 groups compared to the bFGF-PBS and bFGF-control IgG groups. There was no difference between bFGF-CNTO 95 and Matrigel alone groups (P>0.05). For FIG. 25(C), the percentage of Matrigel cross-sectional area occupied by vessels was calculated using computer-assisted image analysis. Each point represents the average density per Matrigel sample (4 samples/animal). A two-tailed unpaired t-test analysis indicated P<0.01 for Matrigel alone and bFGF-CNTO 95 groups compared to the bFGF-HBSS and bFGF-control IgG groups. There was no difference between bFGF-CNTO 95 and Matrigel alone groups (P>0.05).

Figure 26A:
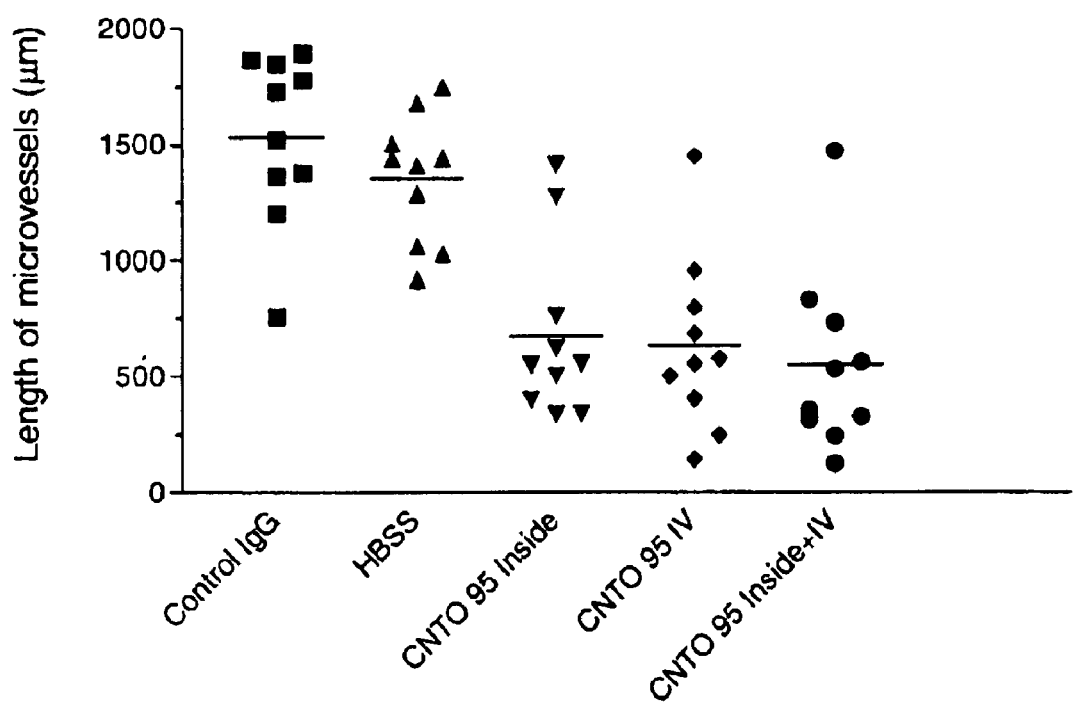

FIG. 26A is a graph of the data on length FIG. 26(A) of blood vessels found in bFGF-impregnated Matrigel plugs in nude rats. Each point represents average per view from one Matrigel plug and the line is the mean from 10 plugs (2 plugs/per animal). Inside refers to CNTO 95 (40 mg/ml) that was included in the Matrigel solution prior to injection. IV refers to CNTO 95 (10 mg/kg) that was injected intravenously as a bolus after the Matrigel solution was injected into the rats. Inside +IV refers to CNTO 95 that was mixed with the Matrigel solution and injected intravenously. A two-tailed unpaired t-test analysis indicated P<0.001 for all three CNTO 95 groups compared to the control IgG group. The three CNTO 95 groups were not statistically different from each other.

Figure 27:
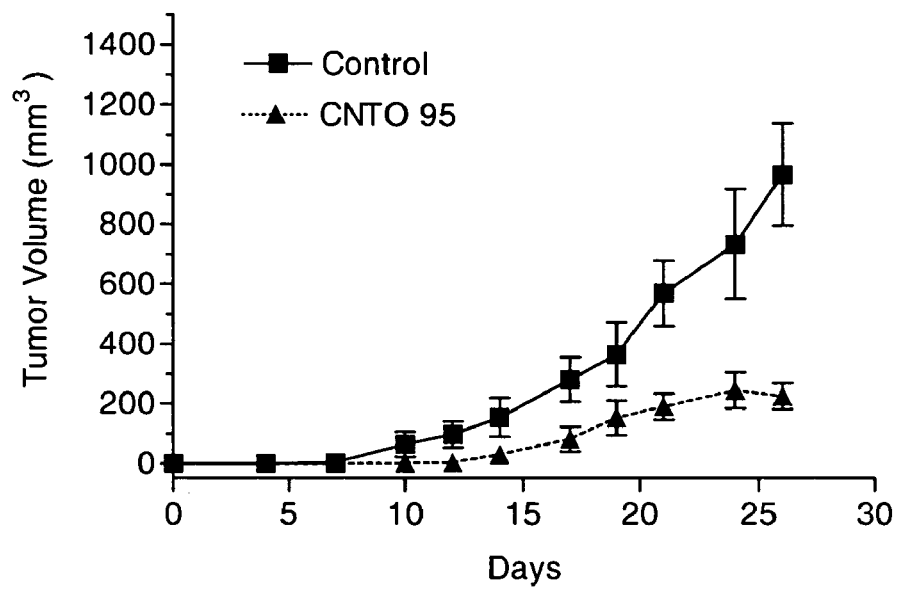

FIG. 27 is a graph showing the change volume over time of a human melanoma tumor in nude mice and the effect of administering CNTO 95. Mice were inoculated subcutaneously with A375.S2 cells (3×106), and dosing with CNTO 95 or control was initiated three days later. Mice were treated with CNTO 95 or vehicle three times per week at a dose of 10 mg/kg i.p. Each data point is the mean tumor volume from 10 tumor-bearing animals (±SEM). CNTO 95 given three times per week significantly inhibited growth of tumors when compared to control treated animals at day 26 (P=0.0005).

Figure 28:
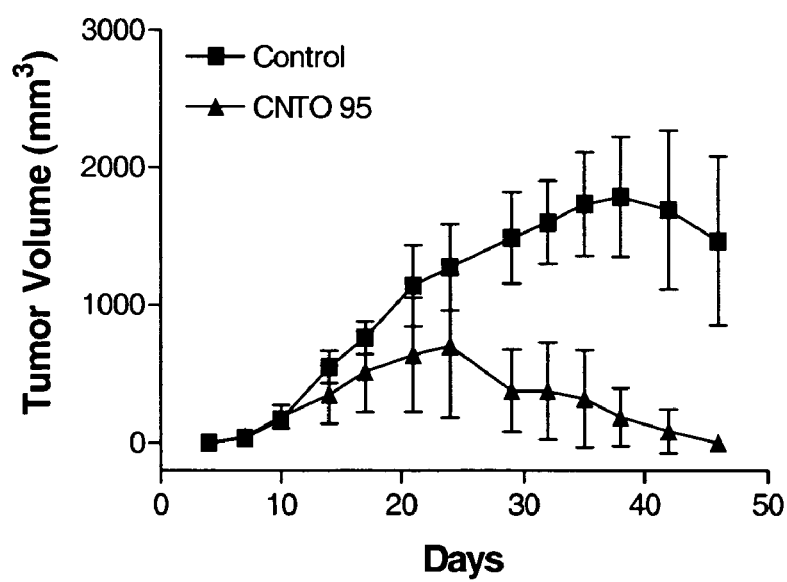

FIG. 28 is a graph showing the change volume over time of a human melanoma tumor in nude rats and the effect of administering CNTO 95. Rats were inoculated subcutaneously with A375.S2 cells (3×106), and therapy with CNTO 95 or control was initiated three days later. Rats were treated with CNTO 95 or vehicle once per week at a dose of 10 mg/kg i.v. Each data point is the mean tumor volume from 9 tumor-bearing animals (±SEM).

DETAILED DESCRIPTION OF THE INVENTION

The present invention provides isolated, recombinant and/or synthetic anti-alpha-V subunit human monoclonal antibodies and alpha-V subunit anti-idiotype antibodies thereto, as well as compositions and encoding nucleic acid molecules comprising at least one polynucleotide encoding at least one anti-alpha-V subunit antibody or anti-idiotype antibody. The present invention further includes, but is not limited to, methods of making and using such nucleic acids and antibodies and anti-idiotype antibodies, including diagnostic and therapeutic compositions, methods and devices. Therapies of the invention employ isolated human monoclonal antibodies and/or related compositions containing the antibodies which bind to an epitope present on the alpha V integrin subunit and is capable of blocking the binding of various alpha V containing integrins, regardless of the beta subunit to which it is associated. In a particular embodiment exemplified herein, the human antibodies are produced in a nonhuman transgenic animal, e.g., a transgenic mouse. Accordingly, aspects of the invention include not only antibodies, antibody fragments, and pharmaceutical compositions thereof, but also nonhuman transgenic animals, B-cells and hybridomas which produce monoclonal antibodies. Methods of using the antibodies of the invention to detect a cell expressing alpha V, or to inhibit growth, differentiation and/or motility of a cell expressing alpha V, either in vitro or in vivo, are also encompassed by the invention.

In order that the present invention may be more readily understood, certain terms are first defined. Additional definitions are set forth throughout the detailed description.

The term "alpha V integrin", "alpha V subunit integrin", and "alpha V subunit containing integrin" are used interchangeably herein to mean Alpha V transmembrane glycoprotein subunits of a functional integrins heterodimer and include all of the variants, isoforms and species homologs of alpha V. Accordingly, human antibodies of the invention may, in certain cases, cross-react with alpha V from species other than human, or other proteins which are structurally related to human alpha V (e.g., human alpha V homologs). In other cases, the antibodies may be completely specific for human alpha V and not exhibit species or other types of cross-reactivity.

As used herein, an "antibody" includes whole antibodies and any antigen binding fragment or a single chain thereof. Thus the antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, which can be incorporated into an antibody of the present invention. An "alpha V antibody", "alpha V subunit antibody" or "alpha V integrin antibody" is an antibody that affects the alpha V ligand, such as but not limited to where such antibody modulates, decreases, increases, antagonizes, angonizes, mitigates, aleviates, blocks, inhibits, abrogates and/or interferes with at least one alpha-V subunit activity or binding, or with alpha-V subunit receptor activity or binding, in vitro, in situ and/or in vivo. As a non-limiting example, a suitable anti-alpha-V subunit antibody, specified portion or variant of the present invention can bind at least one alpha-V subunit, or specified portions, variants or domains thereof. A suitable anti-alpha-V subunit antibody, specified portion, or variant can also optionally affect at least one of alpha-V subunit activity or function, such as but not limited to, RNA, DNA or protein synthesis, alpha-V subunit release, alpha-V subunit receptor signaling, membrane alpha-V subunit cleavage, alpha-V subunit activity, alpha-V subunit production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian alpha-V subunit. Examples of binding fragments encompassed within the term "antigen binding portion" of an antibody include (i) a Fab fragment, a monovalent fragment consisting of the VL, VH, CL and CH, domains; (ii) a F(ab')2 fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment (Ward et al., (1989) Nature 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (I 988) Science 242:423–426,—and Huston et al. (1988) Proc. Natl. Acad Sci. USA 85:5879–5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH, domain and/or hinge region of the heavy chain. The various portions of antibodies can be joined together chemically by conventional techniques, or can be prepared as a contiguous protein using genetic engineering techniques.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The term "native conformational epitope" or "native protein epitope" are used interchangeably herein, and include protein epitopes resulting from conformational folding of the integrin molecule which arise when amino acids from differing portions of the linear sequence of the integrin molecule come together in close proximity in 3 dimensional space. Such conformational epitopes are distributed on the extracellular side of the plasma membrane.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g. a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to cell surface antigens, such as alpha V, and to other targets, such as Fc receptors on effector cells.

The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad Sci. USA 90:6444–6448; Poljak, R. J., et al. (I 994) Structure 2:1121–1123). Bispecific, heterospecific, heteroconjugate or similar antibodies can also be used that are monoclonal, preferably human or humanized, antibodies that have binding specificities for at least two different antigens. In the present case, one of the binding specificities is for at least one alpha-V subunit protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

As used herein, the term "heteroantibodies" refers to two or more antibodies, antibody binding fragments (e.g., Fab), derivatives therefrom, or antigen binding regions linked together, at least two of which have different specificities. These different specificities include a binding specificity for an Fc receptor on an effector cell, and a binding specificity for an antigen or epitope on a target cell, e.g., a tumor cell.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. Thus as used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences.

In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further in Section 1, below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal I0 transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody," as used herein, is intended to refer to an antibody which is substantially free of other antibodies having different antigenic specificities (e.g., an isolated antibody that specifically binds to Alpha V is substantially free of antibodies that specifically bind antigens other than Alpha V). An isolated antibody that specifically binds to an epitope, isoform or variant of human Alpha V may, however, have cross-reactivity to other related antigens, e.g., from other species (e.g., Alpha V species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding" refers to antibody binding to a predetermined antigen. Typically, the antibody binds with a dissociation constant ($K_D$) of 10–7 M or less, and binds to the predetermined antigen with a $K_D$ that is at least twofold less than its $K_D$ for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "high affinity" for an IgG antibody refers to an antibody having a $K_D$ Of $10^{-8}$ M or less, more preferably $10^{-9}$ M or less and even more preferably $10^{-10}$ M or less. However, "high affinity" binding can vary for other antibody isotypes. For example, "high affinity" binding for an IgM isotype refers to an antibody having a $K_D$ of $10^{-7}$ M or less, more preferably $10^{-8}$ M or less. The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction, The term "$K_D$", as used herein, is intended to refer to the dissociation constant, which is obtained from the ratio of Kd to Ka (i. e,. Kd/Ka) and is expressed as a molar concentration (M).

As used herein, "isotype" refers to the antibody class (e.g., IgM or IgG1) that is encoded by heavy chain constant region genes.

The term "nucleic acid molecule", as used herein, is intended to include DNA molecules and RNA molecules. A nucleic acid molecule may be single-stranded or double-stranded, but preferably is double-stranded DNA. The term "isolated nucleic acid molecule," as used herein in reference to nucleic acids encoding antibodies or antibody portions (e.g., VH, VL, CDR3) that bind to Alpha V, is intended to refer to a nucleic acid molecule in which the nucleotide sequences encoding the antibody or antibody portion are free of other nucleotide sequences encoding antibodies or antibody portions that bind antigens other than Alpha V, which other sequences may naturally flank the nucleic acid in human genomic DNA. In one embodiment, the human anti-Alpha V antibody, or portion thereof, includes the nucleotide or amino acid sequence of CNTO 95, as well as heavy chain (VH) and light chain (VL) variable regions having the amino acid sequences shown in SEQ ID NOs: 7 and 8, respectively, and nucleotide sequences encoding them, including SEQ ID Nos: 18 and 19.

As disclosed and claimed herein, the sequences set forth in SEQ ID NOs. 1–8 and 10–15 include "conservative sequence modifications", i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into SEQ ID NOs: 1–8 and 10–15 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-Alpha V antibody is preferably replaced with another amino acid residue from the same side chain family.

Alternatively, in another embodiment, mutations can be introduced randomly along all or part of a anti-Alpha V antibody coding sequence, such as by saturation mutagenesis, and the resulting modified anti-Alpha V antibodies can be screened for binding activity.

Accordingly, antibodies encoded by the (heavy and light chain variable region) nucleotide sequences disclosed herein and/or containing the (heavy and light chain variable region) amino acid sequences disclosed herein (i.e., SEQ ID NOs: 1–8) include substantially similar antibodies encoded by or containing similar sequences which have been conservatively modified. Further discussion as to how such substantially similar antibodies can be generated based on the partial (i.e., heavy and light chain variable regions) sequences disclosed herein as SEQ ID NOs: 1–8 is provided below. For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the sequences hybridize under selective hybridization conditions, to the complement of segments with the strand. The percent identity between two sequences is a function of the number of identical positions shared by the sequences (i.e., % homology=# of identical positions/ total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http:Hwww.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (Comput. AppL Biosci., 4:11–17 (1988)) which has been incorporated into the ALIGN program (version 2.0), using a PAM 1 20 weight residue table, a gap length penalty of 12 and a gap penalty of 4. In addition, the percent identity between two amino acid sequences can be determined using the Needleman and Wunsch (J. Mol. Biol. 48:444–453 (1970)) algorithm which has been incorporated into the GAP program in the GCG software package (available at http:H/www.gcg.com), using either a Blossum 62 matrix or a PAM2 5 0 matrix, and a gap weight of 16, 14, 12, 10, 8, 6, or 4 and a length weight of 1, 2, 3, 4, 5, or 6. The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (I 990) J Mol. Biol. 215.403-1 0. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389 When utilizing BLAST and Gapped BLAST programs, the default parameters of the respective programs (e.g., XBLAST and NBLAST) can be used. See http:Hwww.ncbi.nim.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, colunm chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof, may be mutated in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasinid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells and lymphocytic cells.

As used herein, the term "subject" includes any human or nonhuman animal. The term "nonhuman animal" includes all vertebrates, e.g., mammals and nonmammals, such as nonhuman primates, sheep, dog, cow, chickens, amphibians, reptiles, etc.

The terms "transgenic, nonhuman animal" refers to a nonhuman animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-Alpha V antibodies when immunized with alpha V antigen and/or cells expressing Alpha V. The human heavy chain transgene can be integrated into the chromosomal DNA of the mouse, as is the case for transgenic, e.g., HuMAb mice, or the human heavy chain transgene can be maintained extrachromosomally, as is the case for transchromosomal (e.g., KM) mice as described in WO 02/43478. Such transgenic and transchromosomal mice are capable of producing multiple isotypes of human monoclonal antibodies to Alpha V (e.g., IgG, IgA and/or IgE) by undergoing V-D-J recombination and isotype switching.

Anti-alpha-V subunit antibodies (also termed alpha-V subunit antibodies) useful in the methods and compositions of the present invention are characterized by high affinity binding to alpha-V subunit and preferably having low toxicity. In particular, an antibody, specified fragment or variant of the invention, where the individual components, such as the variable region, constant region and framework, individually and/or collectively, optionally and preferably possess low immunogenicity, are useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., Lancet 344:1125–1127 (1994), entirely incorporated herein by reference).

Citations

All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987–2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994–2001); Colligan et al., Current Protocols in Protein Science, John Wiley & Sons, NY, N.Y., (1997–2001).

1. Productions of Antibodies

Anti-alpha-V subunit antibodies of the present invention can be optionally produced by a variety of techniques, including conventional monoclonal antibody techniques, e.g., the standard somatic cell hybridization technique of Kohler and Milstein (1975) Nature 256:495. A variety of cell lines, mixed cell lines, an immortalized cell or clonal population of immortalized cells, can be used, as well known in the art. See, e.g., Ausubel, et al., ed., Current Protocols in Molecular Biology, John Wiley & Sons, Inc., NY, N.Y. (1987–2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994–2001); Colligan et al., Current Protocols in Protein Science, John Wiley & Sons, NY, N.Y., (1997–2001), each entirely incorporated herein by reference.

Human antibodies that are specific for human alpha-V subunit proteins or fragments thereof can be raised against an appropriate immunogenic antigen, such as isolated and/or alpha-V subunit protein or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O or the like, or heteromyelomas, fusion products thereof, or any cell or fusion cell derived therefrom, or any other suitable cell line as known in the art. See, e.g., www.atcc.org, www.lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, Del.; Biovation, Aberdeen, Scotland, UK; BioInvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260 (May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); EP 614 989 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723, 323, 5,763,192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901–907 (1997); Sandhu et al., Crit. Rev. Biotechnol. 16:95–118 (1996); Eren et al., Immunol. 93:154–161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937–4942 (May 1997); Hanes et al., Proc. Natl. Acad. Sci. USA, 95:14130–14135 (November 1998)); single cell antibody producing technologies (e.g., selected lymphocyte antibody method ("SLAM") (U.S. Pat. No. 5,627,052, Wen et al., J. Immunol. 17:887–892 (1987); Babcook et al., Proc. Natl. Acad. Sci. USA 93:7843–7848 (1996)); gel microdroplet and flow cytometry (Powell et al., Biotechnol. 8:333–337 (1990); One Cell Systems, Cambridge, Mass.; Gray et al., J. Imm. Meth. 182:155–163 (1995); Kenny et al., Bio/Technol. 13:787–790 (1995)); B-cell selection (Steenbakkers et al., Molec. Biol. Reports 19:125–134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., in a number of public databases such as the NCBI database of the National Institute of Health or publications such as Kabat et al., Sequences of Proteins of Immunological Interest, U.S. Dept. Health (1983).

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR (framework) residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, W090/14430, EP 229246, each entirely incorporated herein by reference, included references cited therein.

The anti-alpha-V subunit antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-alpha-V subunit antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856–859 (1994), Taylor et al., Int. Immunol. 6(4)579–591 (1994), Green et al, Nature Genetics 7:13–21 (1994), Mendez et al., Nature Genetics 15:146–156 (1997), Taylor et al., Nucleic Acids Research 20(23):6287–6295 (1992), Tuaillon et al., Proc Natl Acad Sci USA 90(8) 3720–3724 (1993), Lonberg et al., Int Rev Immunol 13(1): 65–93 (1995) and Fishwald et al., Nat Biotechnol 14(7): 845–851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

To generate fully human monoclonal antibodies to Alpha V, HuMAb mice can be immunized with a purified or enriched preparation of Alpha V antigen and/or cells expressing Alpha V, as described by Lonberg, N. et al. (1994) Nature 3 68(6474) 856.859; Fishwild, D. et al. (1996) Nature Biotechnology 14: 845–851 and WO 98/24884. Preferably, the mice will be 6–16 weeks of age upon the first infusion. For example, a purified or enriched preparation (5–20 pg) of Alpha V antigen (e.g., purified from Alpha V-expressing LNCaP cells) can be used to immunize the HuMAb mice intraperitoneally. In the event that immunizations using a purified or enriched preparation of Alpha V antigen do not result in antibodies, mice can also be immunized 1 5 with cells expressing Alpha V, e.g., a tumor cell line, to promote immune responses. Cumulative experience with various antigens has shown that the HuMAb transgenic mice typically respond best when initially immunized intraperitoneally (IP) with antigen in complete Freund's adjuvant, followed by every other week i.p. immunizations (up to a total of 6) with antigen in incomplete Freund's adjuvant, followed by every other week IP/SC immunizations (up to a total of 10) with antigen in incomplete Freund's adjuvant. The immune response can be monitored over the course of the immunization protocol with plasma samples being obtained by retroorbital bleeds. The plasma can be screened by ELISA (as described below), and mice with sufficient titers of anti-Alpha V human immunoglobulin can be used for fusions. Mice can be boosted intravenously with antigen 3 days before sacrifice and removal of the spleen. It is expected that 2–3 fusions for each antigen may need to be performed. Several mice will be immunized for each antigen.

To generate hybridomas producing human monoclonal antibodies to Alpha V, splenocytes and lymph node cells from immunized mice can be isolated and fused to an appropriate immortalized cell line, such as a mouse myeloma cell line. The resulting hybridomas can be screened for the production of antigen-specific antibodies.

Human antibodies of the invention also can be produced in a host cell transfectorma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VI, segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino tem-finus of the antibody chain gene. The signal peptide can be an immunoglobulin signal peptide or a heterologous signal peptide (i.e., a signal peptide from a non-immunoglobulin protein).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (I 985) Immunology Today 6:12–13).

Preferred mammalian host cells for expressing the recombinant antibodies of the invention include Chinese Hamster Ovary (CHO cells) (including dhfrCHO cells, described in Urlaub and Chasin, (1980) Proc. Natl. Acad. Sci. USA 77:42164220, used with a DHFR selectable marker, e.g., as described in R. J. Kaufman and P. A. Sharp (I 982) Mol. Biol. 159:601–62 1), NSO myeloma cells, COS cells and SP2 cells.In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Screening antibodies for specific binding to similar proteins or fragments can also be conveniently achieved using peptide display libraries. This method involves the screening of large collections of peptides for individual members having the desired function or structure, antibody screening of peptide display libraries is well known in the art. The displayed peptide sequences can be from 3 to 5000 or more amino acids in length, frequently from 5–100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278. Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643, 768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5885793, assigned to Cambridge antibody Technologies; U.S. Pat. No. 5,750,373, assigned to Genentech, U.S. Pat. Nos. 5,618,920, 5,595,898, 5,576,195, 5,698,435, 5,693, 493, 5,698,417, assigned to Xoma, Colligan, supra; Ausubel, supra; or Sambrook, supra, each of the above patents and publications entirely incorporated herein by reference.

Antibodies of the present invention can also be prepared using at least one anti-alpha-V subunit antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat.

Nos. 5,827,690; 5,849,992; 4,873,316; 5,849,992; 5,994,616; 5,565,362; 5,304,489, and the like, each of which is entirely incorporated herein by reference.

Antibodies of the present invention can additionally be prepared using at least one anti-alpha-V subunit antibody encoding nucleic acid to provide transgenic plants and cultured plant cells (e.g., but not limited to tobacco, maize, and duckweed) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95–118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127–147 (1999) and references cited therein. antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101–109 (1998) and reference cited therein. Thus, antibodies of the present invention can also be produced using transgenic plants, according to know methods. See also, e.g., Fischer et al., Biotechnol. Appl. Biochem. 30:99–108 (Oct., 1999), Ma et al., Trends Biotechnol. 13:522–7 (1995); Ma et al., Plant Physiol. 109:341–6 (1995); Whitelam et al., Biochem. Soc. Trans. 22:940–944 (1994); and references cited therein. See, also generally for plant expression of antibodies, but not limited to, Each of the above references is entirely incorporated herein by reference.

2. Nucleic Acid Molecules

Using the information provided herein, such as the nucleotide sequences encoding at least 70–100% of the contiguous amino acids of at least one of SEQ ID NOS: 1, 2, 3, 4, 5, 6, 7, 8, specified fragments, variants or consensus sequences thereof, or a deposited vector comprising at least one of these sequences, a nucleic acid molecule of the present invention encoding at least one anti-alpha-V subunit antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain (e.g., SEQ ID NOS: 1–3) or light chain (e.g., SEQ ID NOS: 4–6); nucleic acid molecules comprising the coding sequence for an anti-alpha-V subunit antibody or variable region (e.g., SEQ ID NOS: 7, 8) including but not limited to SEQ ID Nos; 18 and 19; and nucleic acid molecules which comprise a nucleotide sequence substantially different from those described above but which, due to the degeneracy of the genetic code, still encode at least one anti-alpha-V subunit antibody as described herein and/or as known in the art. Of course, the genetic code is well known in the art. Thus, it would be routine for one skilled in the art to generate such degenerate nucleic acid variants that code for specific anti-alpha-V subunit antibodies of the present invention. See, e.g., Ausubel, et al., supra, and such nucleic acid variants are included in the present invention. Non-limiting examples of isolated nucleic acid molecules of the present inveniton include SEQ ID NOS: 10, 11, 12, 13, 14, 15, 18, and 19 corresponding to non-limiting examples of a nucleic acid encoding, respectively, HC CDR1, HC CDR2, HC CDR3, LC CDR1, LC CDR2, LC CDR3, HC variable region and LC variable region.

In another aspect, the invention provides isolated nucleic acid molecules encoding a(n) anti-alpha-V subunit antibody having an amino acid sequence as encoded by the nucleic acid contained in the plasmid designated clone C371A.

As indicated herein, nucleic acid molecules of the present invention which comprise a nucleic acid encoding an anti-alpha-V subunit antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

3. Polynucleotides which Selectively Hybridize to a Polynucleotides as Described Herein The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

4. Construction of Nucleic Acids

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

5. Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

6. Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70–100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or, cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

7. Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

8. Recombinant Expression Cassettes

The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

In addition to the antibody chain genes, the recombinant expression vectors of the invention carry regulatory sequences that control the expression of the antibody chain genes in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (I 990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or P-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with I 0 methotrexate selection/amplification) and the neo gene (for G418 selection).

9. Vectors and Host Cells

The present invention also relates to vectors that include isolated nucleic acid molecules of the present invention, host cells that are genetically engineered with the recombinant vectors, and the production of at least one anti-alpha-V subunit antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827, 739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1–4 and 16–18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29–17.42 and 18.1–18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, PerC.6 cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin such as myeloma and lymphoma cells.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773–781 (1983)). Additionally, gene sequences to control replication in the host cell can be incorporated into the vector, as known in the art. Also, to avoid high surface expression of heavy chain molecules, it may be necessary to use an expression vector that eliminates transmembrane domain variant splices.

10. Purification of an Antibody

An anti-alpha-V subunit antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997–2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37–17.42; Ausubel, supra, Chapters 10, 12, 13, 16, 18 and 20, Colligan, Protein Science, supra, Chapters 12–14, all entirely incorporated herein by reference.

11. Anti-Alpha-V Subunit Antibodies of the Invention

Since it is well known in the art that antibody heavy and light chain CDR3 domains play a particularly important role in the binding specificity/affinity of an antibody for an antigen, the recombinant antibodies of the invention prepared as set forth above preferably comprise the heavy and light chain CDR3s of CNTO 95. The antibodies further can comprise the CDR2s of CNTO 95. The antibodies further can comprise the CDR1s of CNTO 95. Accordingly, the invention further provides anti-alpha V antibodies comprising: (1) human heavy chain framework regions, a human heavy chain CDR1 region, a human heavy chain CDR2 region, and a human heavy chain CDR3 region, wherein the human heavy chain CDR3 region is selected from the CDR3s of CNTO 95 as shown in SEQ ID NO: 3, and (2) human light chain framework regions, a human light chain CDR1 region, a human light chain CDR2 region, and a human light chain CDR3 region, wherein the human light chain CDR3 region is selected from the CDR3s of CNTO 95 as shown in SEQ ID NO: 6, wherein the antibody binds Alpha V integrin. The antibody may further comprise the heavy chain CDR2 and/or the light chain CDR2 of CNTO 95. The antibody may further comprise the heavy chain CDR1 and/or the light chain CDR1 of CNTO 95.

As a non-limiting example, the antibody or antigen-binding portion or variant can comprise at least one of the heavy chain CDR3 having the amino acid sequence of SEQ ID NO:3, and/or a light chain CDR3 having the amino acid sequence of SEQ ID NO:6. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3 (e.g., SEQ ID NOS: 1, 2, and/or 3). In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 (e.g., SEQ ID NOS: 4, 5, and/or 6). In a preferred embodiment the three heavy chain CDRs and the three light chain CDRs of the anitbody or antigen-binding fragment have the amino acid sequence of the corresponding CDR of at least one of mAb CNTO 95, Gen0101, CNTO 95, C372A, as described herein. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

Preferably, the CDR1, 2, and/or 3 of the engineered antibodies described above comprise the exact amino acid sequence(s) as those of CNTO 95 disclosed herein. However, the ordinarily skilled artisan will appreciate that some deviation from the exact CDR sequences of CNTO 95 may be possible while still retaining the ability of the antibody to bind Alpha V effectively (e.g., conservative substitutions). Accordingly, in another embodiment, the engineered antibody may be composed of one or more CDRs that are, for example, 90%, 95%, 98% or 99.5% identical to one or more CDRs of CNTO 95. In addition to simply binding Alpha V, engineered antibodies such as those described above may be selected for their retention of other functional properties of antibodies of the invention, such as:

1). binding to live cells expressing human Alpha V; 2) binding to human Alpha V with a $K_D$ of $10^{-8}$ M or less (e.g., $10^{-9}$ M or $10^{-10}$ M or less); 3) binding to a unique epitope on Alpha V (to eliminate the possibility that monoclonal antibodies with complimentary activities when used in combination would compete for binding to the same epitope); 4) inhibition of angiogenesis resulting in growth inhibition of tumor cells in vivo.

Human monoclonal antibodies of the invention can be tested for binding to Alpha V by, for example, standard ELISA.

To determine if the selected human anti-alpha V monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using alpha V coated-ELISA plates. Biotinylated mAb binding can be detected with a strep-avidin-alkaline phosphatase probe.

To determine the isotype of purified antibodies, isotype ELISAs can be performed. In order to demonstrate binding of monoclonal antibodies to live cells expressing the alpha V, flow cytometry can be used. Anti-alpha V human IgGs can be further tested for reactivity with alpha V antigen by Western blotting.

In another aspect of the invention, the structural features of an human anti-alpha V antibodies of the invention, CNTO 95, are used to create structurally related human anti-Alpha V antibodies that retain at least one functional property of the antibodies of the invention, such as binding to Alpha V. More specifically, one or more CDR regions of CNTO 95 can be combined recombinantly with known human framework regions and CDRs to create additional, recombinantly-engineered, human anti-Alpha V antibodies of the invention.

Accordingly, in another embodiment, the invention provides a method for preparing an anti-Alpha V antibody comprising: preparing an antibody comprising (1) human heavy chain framework regions and human heavy chain CDRs, wherein at least one of the human heavy chain CDRs comprises an amino acid sequence selected from the amino acid sequences of CDRs shown in SEQ ID NOs: 1–3; and (2) human light chain framework regions and human light chain CDRs, wherein at least one of the human heavy chain CDRs comprises an amino acid-sequence selected from the amino acid sequences of CDRs shown in SEQ ID NOs: 4–6; wherein the antibody retains the ability to bind to Alpha V. The ability of the antibody to bind Alpha V can be determined using standard binding assays, such as those set forth in the Examples (e.g., an ELISA).

The antibodies of the invention can bind human alpha-V subunit with a wide range of affinities ($K_D$). In a preferred embodiment, at least one human mAb of the present invention can optionally bind human alpha-V subunit with high affinity. For example, a human mAb can bind human alpha-V subunit with a $K_D$ equal to or less than about $10^{-7}$ M, such as but not limited to, 0.1–9.9 (or any range or value therein) X $10^{-7}$, $10^{-8}$, $10^{-9}$, $10^{-10}$, $10^{-11}$, $10^{-12}$, $10^{-13}$ M or any range or value therein.

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Preferably, the human antibody or antigen-binding fragment of the invention binds human alpha-V subunit and, thereby partially or substantially neutralizes at least one biological activity of the protein. An antibody, or specified portion or variant thereof, that partially or preferably substantially neutralizes at least one biological activity of at least one alpha-V subunit protein or fragment can bind the protein or fragment and thereby inhibit activities mediated through the binding of alpha-V subunit to its ligand or through other alpha-V subunit-dependent or mediated mechanisms. As used herein, the term "neutralizing antibody" refers to an antibody that can inhibit an alpha-V subunit-dependent activity by about 20–120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-alpha-V subunit antibody to inhibit an alpha-V subunit-dependent activity is preferably assessed by at least one suitable alpha-V subunit protein or receptor assay, as described herein and/or as known in the art. A human antibody of the invention can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or lgG4. Antibodies of this type can be prepared by employing a transgenic mouse or other trangenic non-human mammal comprising at least one human light chain (e.g., IgG, IgA and IgM (e.g., □1, □2, □3, □4) transgenes as described herein and/or as known in the art. In another embodiment, the anti-human alpha-V subunit human antibody comprises an IgG1 heavy chain and a IgG1 light chain.

At least one antibody of the invention binds at least one specified epitope specific to at least one alpha-V subunit protein, subunit, fragment, portion or any combination thereof. The at least one epitope can comprise at least one antibody binding region that comprises at least one portion of said protein, which epitope is preferably comprised of at least one extracellular, soluble, hydrophillic, external or cytoplasmic portion of said protein. The at least one specified epitope can comprise any combination of at least one amino acid sequence of at least 1–3 amino acids to the entire specified portion of contiguous amino acids of the SEQ ID NOS:9, 16 or 17.

As previously stated, the invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human alpha-V subunit with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g, charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

An anti-alpha-V subunit antibody of the present invention can include one or more amino acid substitutions, deletions or additions, either from natural mutations or human manipulation, as specified herein.

Of course, the number of amino acid substitutions a skilled artisan would make depends on many factors, including those described above. Generally speaking, the number of amino acid substitutions, insertions or deletions for any given anti-alpha-V subunit antibody will not be more than 40, 30, 20, 19, 18, 17, 16, 15, 14, 13, 12, 11, 10, 9, 8, 7, 6, 5, 4, 3, 2, 1, such as 1–30 or any range or value therein, as specified herein.

Amino acids in an anti-alpha-V subunit antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081–1085 (1989)). The latter procedure introduces single alanine mutations at every residue in the molecule. The resulting mutant molecules are then tested for biological activity, such as, but not limited to at least one alpha-V subunit neutralizing activity. Sites that are critical for antibody binding can also be identified by structural analysis such as crystallization, nuclear magnetic resonance or photoaffinity labeling (Smith, et al., J. Mol. Biol. 224: 899–904 (1992) and de Vos, et al., Science 255:306–312 (1992)).

Anti-alpha-V subunit antibodies of the present invention can include, but are not limited to, at least one portion, sequence or combination selected from 5 to all of the contiguous amino acids of at least one of SEQ ID NOS:1, 2, 3, 4, 5, 6.

A(n) anti-alpha-V subunit antibody can further optionally comprise a polypeptide of at least one of 70–100% of the contiguous amino acids of at least one of SEQ ID NOS: 7, 8.

In one embodiment, the amino acid sequence of an immunoglobulin chain, or portion thereof (e.g., variable region, CDR) has about 70–100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of SEQ ID NOS:7, 8. For example, the amino acid sequence of a light chain variable region can be compared with the sequence of SEQ ID NO:8, or the amino acid sequence of a heavy chain CDR3 can be compared with SEQ ID NO:7. Preferably, 70–100% amino acid identity (i.e., 90, 91, 92, 93, 94, 95, 96, 97, 98, 99, 100 or any range or value therein) is determined using a suitable computer algorithm, as known in the art.

Exemplary heavy chain and light chain variable regions sequences are provided in SEQ ID NOS: 7, 8. The antibodies of the present invention, or specified variants thereof, can comprise any number of contiguous amino acid residues from an antibody of the present invention, wherein that number is selected from the group of integers consisting of from 10–100% of the number of contiguous residues in an anti-alpha-V subunit antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%–100% of that of the native (non-synthetic), endogenous or related and known antibody. Methods of assaying and quantifying measures of enzymatic activity and substrate specificity, are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$. wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include monoesters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent $C_1$–$C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., Bioconjugate Chem., 3:147–153 (1992); Werlen et al., Bioconjugate Chem., 5:411–417 (1994); Kumaran et al., Protein Sci. 6(10):2233–2241 (1997); Itoh et al., Bioorg. Chem., 24(1): 59–68 (1996); Capellas et al., Biotechnol. Bioeng., 56(4): 456–463 (1997)), and the methods described in Hermanson, G. T., Bioconjugate Techniques, Academic Press: San Diego, Calif. (1996).

12. Anti-Idiotype Antibodies to Anti-Alpha-V Subunit Antibody Compositions

In addition to monoclonal or chimeric anti-alpha-V subunit antibodies, the present invention is also directed to an anti-idiotypic (anti-Id) antibody specific for such antibodies of the invention. An anti-Id antibody is an antibody which recognizes unique determinants generally associated with the antigen-binding region of another antibody. The anti-Id can be prepared by immunizing an animal of the same species and genetic type (e.g. mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

13. Anti-Alpha-V Subunit Antibody Compositions

The present invention also provides at least one anti-alpha-V subunit antibody composition comprising at least one, at least two, at least three, at least four, at least five, at least six or more anti-alpha-V subunit antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-alpha-V subunit antibody amino acid sequence selected from the group consisting of 70–100% of the contiguous amino acids of SEQ ID NOS: 1, 2, 3, 4, 5, 6, 7, 8, or specified fragments, domains or variants thereof. Preferred anti-alpha-V subunit antibody compositions include at least one or two full length, fragments, domains or variants as at least one CDR or LBR containing portions of the anti-alpha-V subunit antibody sequence of 70–100% of SEQ ID NOS:1, 2, 3, 4, 5, 6, or specified fragments, domains or variants thereof. Further preferred compositions comprise 40–99% of at least one of 70–100% of SEQ ID NOS: 1, 2, 3, 4, 5, 6, or specified fragments, domains or variants thereof. Such composition percentages are by weight, volume, concentration, molarity, or molality as liquid or dry solutions, mixtures, suspension, emulsions or colloids, as known in the art or as described herein.

Anti-alpha-V subunit antibody compositions of the present invention can further comprise at least one of any suitable and effective amount of a composition or pharmaceutical composition comprising at least one anti-alpha-V subunit antibody to a cell, tissue, organ, animal or patient in need of such modulation, treatment or therapy, optionally further comprising at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteroid, (dexamethasone), an anabolic steroid (testosterone), a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin (rituximab), an immunosuppressive (e.g., basiliximab, cyclosporine, daclizumab), a growth hormone, a hormone antagonist, a reproductive hormone antagonist (flutamide, nilutamide), a hormone release modulator (leuprolide, goserelin), a hormone replacement drug, an estrogen receptor modulator (tamoxifen), a retinoid (tretinoin), a topoisomerase inhibitor (etoposide, irinotecan), a cytoxin (doxorubicin, dacarbazine), a mydriatic, a cycloplegic, an alkylating agent (carboplatin), a nitrogen mustard (melphalen, chlorabucil), a nitrosourea (carmustine, estramustine) an antimetabolite (methotrexate, cytarabine, fluorouracil), a mitotic inhibitor (vincristine, taxol), a radiopharmaceutical (lodine131-tositumomab), a radiosensitizer (misonidazole, tirapazamine) an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine (interferon alpha-2, IL2) or a cytokine antagonist (infliximab). Non-limiting examples of such cytokines include, but are not limted to, any of IL-1 to IL-23, IL-6, anti-tumor antibodies, chemotherapeutic agents or radiation therapies. Suitable dosages are well known in the art. See, e.g., Wells et al., eds., Pharmacotherapy Handbook, 2$^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), Shigella cytotoxin, Aeromonas enterotoxins, toxic shock syndrome toxin-1 (TSST-1), Staphylococcal enterotoxin A (SEA), B (SEB), or C (SEC), *Streptococcal enterotoxins* and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholera-suis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), Klebsiella species, *Pseudomonas aeruginosa*, and *Streptococci*. See, e.g., Stein, ed., INTERNAL MEDICINE, 3rd ed., pp 1–13, Little, Brown and Co., Boston, (1990); Evans et al., eds., Bacterial Infections of Humans: Epidemiology and Control, 2d. Ed., pp 239–254, Plenum Medical Book Co., New York (1991); Mandell et al, Principles and Practice of Infectious Diseases, 3d. Ed., Churchill Livingstone, New York (1990); Berkow et al., eds., The Merck Manual, 16th edition, Merck and Co., Rahway, N.J., 1992; Wood et al, FEMS Microbiology Immunology, 76:121–134 (1991); Marrack et al, Science, 248:705–711 (1990), the contents of which references are incorporated entirely herein by reference.

Anti-alpha-V subunit antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18$^{th}$ Edition, Mack Publishing Co. (Easton, Pa.) 1990. Pharmaceutically acceptable carriers can be routinely selected that are suitable for the mode of administration, solubility and/or stability of the anti-alpha-V subunit antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1–99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-alpha-V subunit antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, anti-alpha-V subunit antibody compositions of the invention can include polymeric excipients/additives such as polyvinylpyrrolidones, ficolls (a polymeric sugar), dextrates (e.g., cyclodextrins, such as 2-hydroxypropyl-□-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-alpha-V subunit antibody, portion or variant compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), the disclosures of which are entirely incorporated herein by reference. Preferrred carrier or excipient materials are carbohydrates (e.g., saccharides and alditols) and buffers (e.g., citrate) or polymeric agents.

14. Formulations

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one anti-alpha-V subunit antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001–5%, or any range or value therein, such as, but not limited to 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1–2% m-cresol (e.g., 0.2, 0.3. 0.4, 0.5, 0.9, 1.0%), 0.1–3% benzyl alcohol (e.g., 0.5, 0.9, 1.1., 1.5, 1.9, 2.0, 2.5%), 0.001–0.5% thimerosal (e.g., 0.005, 0.01), 0.001–2.0% phenol (e.g., 0.05, 0.25, 0.28, 0.5, 0.9, 1.0%), 0.0005–1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-alpha-V subunit antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-alpha-V subunit antibody, and a second vial comprising an aqueous diluent of prescribed buffer or preservative, wherein said packaging material comprises a label that instructs a patient to reconstitute the at least one anti-alpha-V subunit antibody in the aqueous diluent to form a solution that can be held over a period of twenty-four hours or greater.

The at least one anti-alpha-V subunitantibody used in accordance with the present invention can be produced by recombinant means, including from mammalian cell or transgenic preparations, or can be purified from other biological sources, as described herein or as known in the art.

The range of at least one anti-alpha-V subunit antibody in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-alpha-V subunit antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-alpha-V subunit antibody and preservative in an aqueous diluent is carried out using conventional dissolution and mixing procedures. To prepare a suitable formulation, for example, a measured amount of at least one anti-alpha-V subunit antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one anti-alpha-V subunit antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1–12 months, one-half, one and a half, and/or two years.

The solutions of at least one anti-alpha-V subunit antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-alpha-V subunit antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-alpha-V subunit antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®' NovoPen®, B-D®Pen, AutoPen®, and OptiPen®, GenotropinPen®, Genotronorm Pen®, Humatro Pen®, Reco-Pen®, Roferon Pen®, Biojector®, iject®, J-tip Needle-Free Injector®, Intraject®, Medi-Ject®, e.g., as made or developed by Becton Dickensen (Franklin Lakes, N.J., www.bectondickenson.com), Disetronic (Burgdorf, Switzerland, www.disetronic.com; Bioject, Portland, Oregon (www.bioject.com); National Medical Products, Weston Medical (Peterborough, UK, www.weston-medical.com), Medi-Ject Corp (Minneapolis, Minn., www.mediject.com). Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one anti-alpha-V subunit antibody in the aqueous diluent to form a solution and to use the solution over a period of 2–24 hours or greater for the two vial, wet/dry, product. For the single vial, solution product, the label indicates that such solution can be used over a period of 2–24 hours or greater. The presently claimed products are useful for human pharmaceutical product use.

The formulations of the present invention can be prepared by a process that comprises mixing at least one anti-alpha-V subunit antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one anti-alpha-V subunit antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one anti-alpha-V subunit antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

15. Therapeutic Applications

The anti-alpha-V subunit antibodies of the present invention or specified variants thereof can be used to measure or effect in an cell, tissue, organ or animal (including mammals and humans), to diagnose, monitor, modulate, treat, alleviate, help prevent the incidence of, or reduce the symptoms of, at least one condition mediated, affected or modulated by alpha V integrins. Such conditions are selected from, but not limited to, diseases or conditions mediated by cell adhesion and/or angiogenesis. Such diseases or conditions include an immune disorder or disease, a cardiovascular disorder or disease, an infectious, malignant, and/or neurologic disorder or disease, or other known or specified alpha-V integrin subunit related conditions. In particular, the antibodies are useful for the treatment of diseases that involve angiogenesis such as disease of the eye and neoplastic disease, tissue remodeling such as restenosis, and proliferation of certain cells types particularly epithelial and squamous cell carcinomas. Particular indications include use in the treatment of atherosclerosis, restenosis, cancer metastasis, rheumatoid arthritis, diabetic retinopathy and macular degeneration. The neutralizing antibodies of the invention are also useful to prevent or treat unwanted bone resorption or degradation, for example as found in osteoporosis or resulting from PTHrP overexpression by some tumors. The antibodies may also be useful in the treatment of various fibrotic diseases such as idiopathic pulmonary fibrosis, diabetic nephropathy, hepatitis, and cirrhosis.

Thus, the present invention provides a method for modulating or treating at least one alpha-V subunit related disease, in a cell, tissue, organ, animal, or patient, as known in the art or as described herein, using at least one alpha-V subunit antibody of the present invention. Particular indications are discussed below:

Malignant Disease

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, renal cell carcinoma, breast cancer, nasopharyngeal carcinoma, malignant histiocytosis, paraneoplastic syndrome/hypercalcemia of malignancy, solid tumors, adenocarcinomas, squamous cell carcinomas, sarcomas, malignant melanoma, particularly metastatic melanoma, hemangioma, metastatic disease, cancer related bone resorption, cancer related bone pain, and the like.

Immune Related Disease

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, OKT3 therapy, anti-CD3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

Cardiovascular Disease

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherloscierotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one anti-alpha-V subunit antibody to a cell, tissue, organ, animal or patient in need of such modulation, treatment or therapy.

Neurologic Disease

The present invention also provides a method for modulating or treating at least one neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi.system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16$^{th}$ Edition, Merck & Company, Rahway, N.J. (1992).

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottitis, e. coli 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, mycobacterium tuberculosis, mycobacterium avium intracellulare, pneumocystis carinii pneumonia, pelvic inflammatory disease, orchitis/epidydimitis, legionella, lyme disease, influenza a, epstein-barr virus, vital-associated hemaphagocytic syndrome, vital encephalitis/aseptic meningitis, and the like.

Any method of the present invention can comprise administering an effective amount of a composition or pharmaceutical composition comprising at least one anti-alpha-V subunit antibody to a cell, tissue, organ, animal or patient in need of such modulation, treatment or therapy. Such a method can optionally further at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluroquinolone, a macrolide, a penicillin, a sulfonamide, a tetracycline, another antimicrobial), an antipsoriatic, a corticosteriod (dexamethasone), an anabolic steroid (testosterone), a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin (rituximab), an immunosuppressive (e.g., basiliximab, cyclosporine, daclizumab), a growth hormone, a hormone antagonist, a reproductive hormone antagonist (flutamide, nilutamide), a hormone release modulator (leuprolide, goserelin), a hormone replacement drug, an estrogen receptor modulator (tamoxifen), a retinoid (tretinoin), a topoisomerase inhibitor (etoposide, irinotecan), a cytoxin (doxorubicin), a mydriatic, a cycloplegic, an alkylating agent (carboplatin), a nitrogen mustard (melphalen, chlorabucil), a nitrosourea (carmustine, estramustine) an antimetabolite (methotrexate, cytarabine, fluorouracil), a mitotic inhibitor (vincristine, taxol), a radiopharmaceutical (Iodine131-tositumomab), a radiosensitizer (misonidazole, tirapazamine) an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine (interferon alpha-2, IL2) or a cytokine antagonist (inflixamab). Suitable dosages are well known in the art. See, e.g., Wells et al., eds., Pharmacotherapy Handbook, 2$^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Particular combinations for treatment of neoplastic diseases comprise co-administration or combination therapy by administering, before concurrently, and/or after, an antineplastic agent such as an alkylating agent, a nitrogen mustard, a nitrosurea, an antibiotic, an anti-metabolite, a hormonal agonist or antagonist, an immunomodulator, and the like. For use in metastatic melanoma and other neoplastic diseases, a preferred combination is to co-administer the antibody with dacarbazine, interferon alpha, interleukin-2, temozolomide, cisplatin, vinblastine, Imatinib Mesylate, carmustine, paclitaxel and the like. For metastatic melanoma, dacarbazine is preferred.

Therapeutic Treatments

Typically, treatment of pathologic conditions is effected by administering an effective amount or dosage of at least one anti-alpha-V subunit antibody composition that total, on average, a range from at least about 0.01 to 500 milligrams of at least one anti-alpha-V subunitantibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1–5000 µg/ml serum concentration per single or multiple adminstration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100–500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3,4, 5,6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5–99.999% by weight based on the total weight of the composition.

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1–10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes of can be used according to the present invention for administering pharmaceutically effective amounts of at least one anti-alpha-V subunit antibody according to the present invention. While pulmonary administration is used in the following description, other modes of administration can be used according to the present invention with suitable results.

Alpha-V subunit antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aquous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semi-synthtetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Alternative Delivery

The invention further relates to the administration of at least one anti-alpha-V subunit antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one anti-alpha-V subunit antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59–90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration

For pulmonary administration, preferably at least one anti-alpha-V subunit antibody composition is delivered in a particle size effective for reaching the lower airways of the lung or sinuses. According to the invention, at least one anti-alpha-V subunit antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one anti-alpha-V subunit antibody is delivered by a dry powder inhaler or a sprayer. There are a several desirable features of an inhalation device for administering at least one antibody of the present invention. For example, delivery by the inhalation device is advantageously reliable, reproducible, and accurate. The inhalation device can optionally deliver small dry particles, e.g. less than about 10 □m, preferably about 1–5 □m, for good respirability.

Administration of Alpha-V Subunit Antibody Compositions as a Spray

A spray including alpha-V subunit antibody composition protein can be produced by forcing a suspension or solution of at least one anti-alpha-V subunit antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one anti-alpha-V subunit antibody composition protein delivered by a sprayer have a particle size less than about 10 □m, preferably in the range of about 1 μm to about 5 μm, and most preferably about 2 μm to about 3 μm.

Formulations of at least one anti-alpha-V subunit antibody composition protein suitable for use with a sprayer typically include antibody composition protein in an aqueous solution at a concentration of about 0.1 mg to about 100 mg of at least one anti-alpha-V subunit antibody composition protein per ml of solution or mg/gm, or any range or value therein, e.g., but not lmited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition protein, such as a buffer, a reducing agent, a bulk protein, or a carbohydrate. Bulk proteins useful in formulating antibody composition proteins include albumin, protamine, or the like. Typical carbohydrates useful in formulating antibody composition proteins include sucrose, mannitol, lactose, trehalose, glucose, or the like. The antibody composition protein formulation can also include a surfactant, which can reduce or prevent surface-induced aggregation of the antibody composition protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as alpha-V subunit antibodies, or specified portions or variants, can also be included in the formulation.

Administration of Alpha-V Subunit Antibody Compositions by a Nebulizer

Antibody composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 µm, preferably in the range of about 1 µm to about 5 µm, and most preferably about 2 µm to about 3 µm.

Formulations of at least one anti-alpha-V subunit antibody suitable for use with a nebulizer, either jet or ultrasonic, typically include a concentration of about 0.1 mg to about 100 mg of at least one anti-alpha-V subunit antibody protein per ml of solution. The formulation can include agents such as an excipient, a buffer, an isotonicity agent, a preservative, a surfactant, and, preferably, zinc. The formulation can also include an excipient or agent for stabilization of the at least one anti-alpha-V subunit antibody composition protein, such as a buffer, a reducing agent, a bulk protein, or a carbohydrate. Bulk proteins useful in formulating at least one anti-alpha-V subunit antibody composition proteins include albumin, protamine, or the like. Typical carbohydrates useful in formulating at least one anti-alpha-V subunit antibody include sucrose, mannitol, lactose, trehalose, glucose, or the like. The at least one anti-alpha-V subunit antibody formulation can also include a surfactant, which can reduce or prevent surface-induced aggregation of the at least one anti-alpha-V subunit antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

Administration of Alpha-V Subunit Antibody Compositions by a Metered Dose Inhaler In a metered dose inhaler (MDI), a propellant, at least one anti-alpha-V subunit antibody, and any excipients or other additives are contained in a canister as a mixture including a liquefied compressed gas. Actuation of the metering valve releases the mixture as an aerosol, preferably containing particles in the size range of less than about 10 µm, preferably about 1 µm to about 5 µm, and most preferably about 2 µm to about 3 µm. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one anti-alpha-V subunit antibody for use with a metered-dose inhaler device will generally include a finely divided powder containing at least one anti-alpha-V subunit antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. Preferably the propellant is a hydrofluorocarbon. The surfactant can be chosen to stabilize the at least one anti-alpha-V subunit antibody as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein such as protein can also be included in the formulation.

One of ordinary skill in the art will recognize that the methods of the current invention can be achieved by pulmonary administration of at least one anti-alpha-V subunit antibody compositions via devices not described herein.

Oral Formulations and Administration

Formulations for oral rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, .alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925, 673). Furthermore, carrier compounds described in U.S. Pat. Nos. 5,879,681 and 5,5,871,753 are used to deliver biologically active agents orally are known in the art.

Mucosal Formulations and Administration

For absorption through mucosal surfaces, compositions and methods of administering at least one anti-alpha-V subunit antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

Transdermal Formulations and Administration

For transdermal administration, the at least one anti-alpha-V subunit antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Prolonged Administration and Formulations

It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

16. Diagnostic and Research Applications.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^{3}H$, $^{14}C$, $^{32}P$, $^{36}S$, or $^{126}I$, a fluorescent or chemiluminescent compound, such as fluorescein isothiocyanate, rhodamine, or luciferin; radioactive isotopic labels, such as, e.g., $^{125}I$, $^{32}P$, $^{14}C$, technicium, or $^{3}H$, or an enzyme, such as alkaline phosphatase, beta-galactosidase or horseradish peroxidase.

Any method known in the art for separately conjugating the antibody to the detectable moiety may be employed, including those methods described by Hunter, et al., Nature 144:945 (1962); David, e at., Biochemistry 13:1014 (1974); Pain, et al., J. Immunol. Meth. 40:219 (1981); and Nygren, J. Histochem. and Cytochem. 30:407 (1982).

The antibodies of the present invention may be employed in any known assay method, such as competitive binding assays, direct and indirect sandwich assays, and immunoprecipitation assays. Zola, Monoclonal Antibodies: A Manual of Techniques, pp.147–158 (CRC Press, Inc., 1987).

Competitive binding assays rely on the ability of a labeled standard (which may be alpha.v or an immunologically reactive portion thereof) to compete with the test sample analyte (alpha.v) for binding with a limited amount of antibody. The amount of .alpha.v in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies of the invention also are useful for in vivo imaging, wherein an antibody labeled with a detectable moiety such as a radio-opaque agent or radioisotope is administered to, a host, preferably into the bloodstream, and the presence and location of the labeled antibody in the host is assayed. This imaging technique is useful in the staging and treatment of neoplasms or bone disorders. The antibody may be labeled with any moiety that is detectable in a host, whether by nuclear magnetic resonance, radiology, or other detection means known in the art.

Having generally described the invention, the same will be more readily understood by reference to the following examples, which are provided by way of illustration and are not intended as limiting.

EXAMPLE 1

Cloning and Expression of Alpha-V Subunit Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277–279 (1991); Bebbington, et al., Bio/Technology 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen, et al., Molec. Cell. Biol. 5:438–447 (1985)) plus a fragment of the CMV-enhancer (Boshart, et al., Cell 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells

The vector pC4 is used for the expression of alpha-V subunit antibody. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., J. Biol. Chem. 253: 1357–1370 (1978); J. L. Hamlin and C. Ma, Biochem. et Biophys. Acta 1097:107–143 (1990); and M. J. Page and M. A. Sydenham, Biotechnology 9:64–68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438–447 (1985)) plus a fragment isolated from the enhancer of the immediate early gene of human cytomegalovirus (CMV) (Boshart, et al., Cell 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the alpha-V subunit antibody in a regulated way in mammalian cells (M. Gossen, and H. Bujard, Proc. Natl. Acad. Sci. USA 89: 5547–5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The DNA sequence encoding the complete alpha-V subunit antibody is used, corresponding to HC and LC variable regions of a alpha-V subunit antibody of the present invention, according to known method steps. Isolated nucleic acid encoding a suitable human constant region (i.e., HC and LC regions) is also used in this.

The isolated variable and constant region encoding DNA and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 μg of the expression plasmid pC4 is cotransfected with 0.5 μg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 μg/ml G418. After 2 days, the cells are trypsinized and seeded in hybridoma cloning plates (Greiner, Germany) in alpha minus MEM supplemented with 10, 25, or 50 ng/ml of methotrexate plus 1 μg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100–200 mM. Expression of the desired gene product is analyzed, for instance, by SDS-PAGE and Western blot or by reverse phase HPLC analysis.

EXAMPLE 2

Method of Making and Characterization on Non-Limiting Example of Fully Human Alpha-V Subunit Antibody Summary. (CBA/J×C57/BL6/J) $F_2$ hybrid mice (Taylor et al., International Immunology 6:579–591 (1993); Lonberg et al., Nature 368:856–859 (1994); Neuberger, Nature Biotechnology 14:826 (1996); Fishwild et al., Nature Biotechnology 14:845–851 (1996)) containing human variable and constant region antibody transgenes for both heavy and light chains were immunized with human placental αVβ3. One fusion yielded 2 totally human αVβ3 reactive IgGIK monoclonal antibodies, named CNTO 95 and GenO.101. The totally human anti-αVβ3 antibodies were further characterized and both were found to be reactive to the αVβ3 and αVβ5 subunits suggesting specificity for the shared alpha chain of both molecules. One Mab, CNTO 95, also known as CNTO 95, inhibits the binding of both αVβ3 and αVβ5 to vitronectin in cell based assays.

Abbreviations:
BSA—bovine serum albumin
$CO_2$—carbon dioxide
DMSO—dimethyl sulfoxide
EIA—enzyme immunoassay
FBS—fetal bovine serum
$H_2O_2$—hydrogen peroxide
HC—heavy chain
HRP—horseradish peroxidase
Ig—immunoglobulin
IP—intraperitoneal
IV—intravenous
Mab—monoclonal antibody
OD—optical density
OPD—o-Phenylenediamine dihydrochloride
PEG—polyethylene glycol
PSA—penicillin, streptomycin, amphotericin
RT—room temperature
SQ—subcutaneous
TBS—Tris buffered saline
v/v—volume per volume
w/v—weight per volume Introduction:

We have utilized transgenic mice that contain human heavy and light chain immunoglobulin genes to generate totally human monoclonal antibodies that are specific to the αV integrins. These novel antibodies can be used therapeutically to inhibit the angiogenic process by blocking the binding of αV integrins to their respective ECM ligands and provide additional tools in the treatment of various cancers.

Materials and Methods

Animals

Transgenic mice have been developed by GenPharm International that express human immunoglobulins but not mouse IgM or Igκ. These mice contain human sequence transgenes that undergo V(D)J joining, heavy-chain class switching and somatic mutation to generate a repertoire of human sequence immunoglobulins (Taylor et al., International Immunology 6:579–591 (1993)). The light chain transgene is derived in part from a yeast artificial chromosome clone that includes nearly half of the germline human Vκ region. In addition to several VH genes, the heavy-chain (HC) transgene encodes both human μ and human γ1 (Lonberg et al., Nature 368:856–859 (1994)) and/or γ3 constant regions. A mouse derived from the HC012 genotypic lineage was used in the immunization and fusion process to generate these monoclonal antibodies.

Purification of Human αVβ3

Human placenta (disrupted using a meat grinder) or M21 human melanoma cells expressing the αVβ3 integrin were extracted with saline containing 20 mM Tris pH 7.5, 1 mM $CaCl_2$, 1 mM $MnCl_2$, 100 mM Octylthioglucoside (OTG from Pierce), 0.05% sodium azide and 1 mM phenylmethylsulfonyl fluoride (Sigma). The mixture was stirred for 1 hr at room temperature and clarified by centrifugation at 10,000×g. The supernatant from placental extracts was applied to an affinity column consisting of Mab 10E5 coupled to sepharose (Pharmacia) to remove GPIIb/IIIa and the flow-through fraction was applied to an affinity column consisting of Mab c7E3 Fab coupled to sepharose (Pharmacia) to bind αVβ3. The c7E3 column was washed with PBS containing 1 mM $CaCl_2$, 1 mM $MnCl_2$, and 0.1% OTG followed by 0.1M sodium acetate pH 4.5, 1 mM $CaCl_2$, 1 mM $MnCl_2$, and 0.1% OTG, pH 3.0. The column was eluted with 0.1M glycine, 2% acetic acid, 1 mM $CaCl_2$, 1 mM $MnCl_2$, and 0.1% OTG. The eluate containing purified αVβ3 was neutralized using 2M Tris pH 8.5. Purity of the preparations was characterized by SDS-PAGE analysis and ELISA to rule out GPIIb/IIIa contamination (Wayner, et al., J. Cell Biol. 113: 919–929 (1991)).

Immunizations

A fifteen to 17 week old surgically castrated male mouse obtained from GenPharm was immunized IP (200 μL) and in 2 sites SQ (100 μL per site) with a total of 20 μg of placental αVβ3 (prep V fraction, JG21197) emulsified with an equal volume of complete Freund's adjuvant (day 0). The mouse was immunized two weeks later in the same manner with αVβ3 emulsified with an equal volume of incomplete Freund's adjuvant. Three subsequent 10 μg IP/10 μg SQ injections with incomplete Freund's adjuvant were administered on days 28, 42, and 56. The mouse was then bled on days 42 and 56 by retro-orbital puncture without anti-coagulant. The blood was allowed to clot at RT for one hour and the serum was collected and titered using an αVβ3 solid phase EIA assay. The fusion, named GenO, was performed when repeated injections did not cause titers to increase. At that time, the mouse with a specific human IgG titer of 1:1280 against αVβ3 was given a final IV booster injection of 10 μg αVβ3 diluted in 100 μL physiological saline. Three days later, the mouse was euthanized by cervical dislocation and the spleen was removed aseptically and immersed in 10 mL of cold phosphate buffered saline (PBS) containing 100 U/mL penicillin, 100 μg/mL streptomycin, and 0.25 μg/mL amphotericin B (PSA). The splenocytes were harvested by sterilely perfusing the spleen with PSA-PBS. The cells were washed once in cold PSA-PBS, counted using Trypan blue dye exclusion and resuspended in RPMI 1640 media containing 25 mM Hepes.

Cell Lines

The non-secreting mouse myeloma fusion partner, SP2/0 was employed. The cell line was expanded in αMEM (modified) medium (JRH Biosciences) supplemented with 10% (v/v) FBS (Cell Culture Labs), 1 mM sodium pyruvate, 0.1 mM NEAA, 2 mM L-glutamine (all from JRH Biosciences) and cryopreserved in 95% FBS and 5% DMSO (Sigma), then stored in a vapor phase liquid nitrogen freezer in CBS. The cell bank was sterile (Quality Control Centocor, Malvern) and free of mycoplasma (Bionique Laboratories). Cells were maintained in log phase culture until fusion. They were washed in PBS, counted, and viability determined (>95%) via trypan blue dye exclusion prior to fusion.

The M21 cell line, a human melanoma expressing the αVβ3 and αVβ5 integrins, was expanded and cryopreserved. The 10-vial research cell bank was received into Cell Biology Services and stored in liquid nitrogen. The cell bank was sterile and free of mycoplasma (Bionique Laboratories). The MDAMB435L2 cell line, a human breast carcinoma, was a gift from Dr. Janet Price (MD Anderson, Houston Tex.) expresses the integrin αVβ3. The cell line was cryopreserved in Cell Biology Services. The cell bank was sterile and free of mycoplasma (Bionique Laboratories). M21 and MDAMB435L2 cells were thawed, propagated in appropriate media and maintained in log phase for several days prior to use in bioassays or allowed to reach confluency for use in the purification of αVβ3 protein (M21 cells).

Cell Fusion

Fusion was carried out at a 1:1 ratio of murine myeloma cells (SP2/0) to viable spleen cells. Briefly, spleen cells and myeloma cells were pelleted together. The pellet was slowly resuspended, over 30 seconds, in 1 mL of 50% (w/v) PEG/PBS solution (PEG molecular weight 3,000, Sigma) at 37° C. The fusion was stopped by slowly adding 1 mL of Dulbecco's PBS (JRH) (37° C.) over 1 minute. An additional 19 mL of PBS was added over the next 90 seconds. The fused cells were centrifuged for 5 minutes at 750 rpm. The cells were then resuspended in HAT medium ((αMEM medium containing 20% Fetal Bovine Serum (JRH), 1 mM sodium pyruvate, 2 mM L-glutamine, 0.1 mM Non-essential amino acids, 10 μg/mL gentamicin, 2.5% Origen culturing supplement (Fisher), 50 μM 2-mercaptoethanol, 100 μM hypoxanthine, 0.4 μM aminopterin, and 16 μM thymidine) and then plated at 200 μL/well in thirteen 96-well flat bottom tissue culture plates. The plates were then placed in a humidified 37° C. incubator containing 5% $CO_2$ and 95% air for 7–10 days.

Detection of Human IgG Anti-αVβ3 Antibodies in Mouse Serum

Solid phase EIAs were used to screen mouse sera for human IgG antibodies specific for human αVβ3. Briefly, plates were coated with αVβ3 at 1 μg/mL in PBS overnight. After washing in 0.15M saline containing 0.02% (v/v) Tween 20, the wells were blocked with 1% (w/v) BSA in HBSS with $Ca^{++}$ and $Mg^{++}$, 200 μL/well for 1 hour at RT. Plates were used immediately or frozen at −20° C. for future use. Mouse sera were incubated in doubling dilutions on the αVβ3 coated plates at 50 μL/well at RT for 1 hour. The plates were washed and then probed with 50 μL/well HRP-labeled goat anti-human IgG, Fc specific (Accurate) diluted 1:30,000 in 1% BSA-PBS for 1 hour at RT. The plates were again washed and 100 μL/well of the citrate-phosphate substrate solution (0.1M citric acid and 0.2M sodium phosphate, 0.01% $H_2O_2$ and 1 mg/mL OPD) was added for 15 minutes at RT. Stop solution (4N sulfuric acid) was then added at 25 μL/well and the OD's were read at 490 nm via an automated plate spectrophotometer.

Detection of Totally Human Immunoglobulins in Hybridoma Supernatants

Because the GenPharm mouse is capable of generating both mouse and human immunoglobulin chains, growth positive hybridomas secreting fully human immunoglobulins were detected using two separate EIA sysetms. Plates were coated as described above and undiluted hybridoma supernatants were incubated on the plates for one hour at 37° C. The plates were washed and probed with either HRP labeled goat anti-human kappa (Southern Biotech) antibody diluted 1:10,000 in 1% BSA-HBSS or HRP labeled goat anti-human IgG Fc specific antibody diluted to 1:30,000 in 1% BSA-HBSS for one hour at 37° C. The plates were then incubated with substrate solution as described above.

Isotyping

Isotype determination of the antibodies was accomplished using an EIA in a format similar to that used to screen the mouse immune sera for specific titers. αVβ3 was coated on 96-well plates as described above and purified antibody at 2 μg/mL was incubated on the plate for one hour at RT. The plate was washed and probed with HRP labeled goat anti-human $IgG_1$ (Binding Site) or HRP labeled goat anti-human $IgG_3$ diluted at 1:4000 (Zymed) in 1% BSA-HBSS for one hour at RT. The plate was again washed and incubated with substrate solution as described above.

Preparation of Anti-Idiotype Antibodies to CNTO95

Seventeen monoclonal antibodies were made to the variable region of CNTO 95. Six of them are non-blocking. The remaining eleven appear to block the active site of CNTO 95 and inhibit the binding of CNTO 95 to human integrin aVb3 and do not bind to CNTO 95 prebound to its receptor. The non-blocking Mab, CNTO 1073, can detect CNTO 95 pre-bound to aVb3. Pooled human serum does not interfere with the binding of 16 of 17 CNTO 95 anti-variable region Mabs.

The anti-idiotype Mabs are useful in pharmacokinetic or immunohistochemical detection of CNTO 95 in patient and animal tissue or sera samples as well as in epitope mapping efforts to define the binding regions of CNTO 95 to its targe Binding Characteristics of Human Monoclonal Antibodies to AlphaV by EIA Binding characteristics for the antibodies were assessed using an αVβ3 capture EIA. Linbro plates were coated with αVβ3 at 1 μg/ML in TBS with 2 mM calcium overnight at 4° C. Plates were washed and blocked with TBS/1% BSA/calcium for at least one hour at room temperature. Purified antibodies were incubated in doubling dilutions from a starting concentration of 2 μg/mL. Plates were washed and conjugated antibodies (HRP-labeled goat anti-human IgG Fc at 1:30,000) were added and incubated on plates for one hour at room temperature. Plates were washed OPD substrate was added to wells. Plates were read via an automated plate spectrophotometer.

Competition of Binding of CNTO95 to M21 Cells by Various Commercial Anti-Integrin Mabs M21 Cells were trypsinized from culture flasks, washed and resuspended in HBSS/calcium to $2 \times 10^6$ cell/mL. GenO95 was prelabeled with FYFC-goat anti-human Fc (Jackson) for 30 minutes at RT. 10× concentrations of GenO95 of 200 μg/mL or 20 μg/mL were incubated with FITC-goat anti-human IgG at 250 μg/mL. Aliquots of 100 μL of M21 cells ($2 \times 10^5$ cells) were incubated with 12 μL 10× GenO95 at high (20 μg/mL final) and low (2 μg/mL final) concentrations±12 μL of the following murine antibodies:

m7E3 IgG, anti-αVβ3 (clone LM609, Chemicon), anti-αVβ5 (clone P1F6, Gibco), anti-β3 (Chemicon, AMAC), or anti-αV (clone VNR139, Gibco) antibodies (at 20 μg/mL) for 45 minutes at 37° C. An aliquot was removed from each tube (for two-color analysis) and the remainder was fixed with 1% paraformaldehyde and analyzed on a flow cytometer. For two-color analysis, an aliquot (50 μL) was incubated with PE-goat anti-mouse IgG for 30 minutes at RT to label murine anti-αVβ3, anti-αVβ3, anti-β3, or anti-αV antibodies for two-color analysis. All tubes were fixed with 1% paraformaldehyde.

Inhibition of αVβ3 or αVβ5 Dependent M21 Cell or MDA MB435L2 Cell Adhesion to Vitronectin Coated Plates by αVβ3/αVβ5 Specific Mabs Linbro plates were coated for 1 hour at room temperature 50 μL/well of vitronectin (Collaborative, Becton Dickinson) at 5 μg/mL in TBS with 2 mM calcium. Plates were washed with HBSS/calcium and blocked with TBS containing 2 mM calcium and 1% BSA for 30 minutes at RT. M21 cells were trypsinized, washed once with media containing FCS and resuspended in 3 mL HBSS without calcium. All washes were done with 10 minute spins at 1000 rpm in the Sorvall tabletop centrifuge. To fluorescently label the cells, calcein (Molecular Probes) (5 mg/mL in DMSO) was added to the cells to a final concentration of 100 μg/mL in a 50 mL conical tube (wrapped in foil). Cells were incubated 10 to 15 minutes at 37° C. Calcein labeled cells were washed once with HBSS and resuspended in HBSS supplemented with 0.1% BSA and 1 mM $MgCl_2$. Antibodies were titrated (14-fold dilution series) in HBSS/0.1% BSA/2 mM calcium at 10× final concentration. Cells (300 μL at $7.5 \times 10^6$/mL) were preincubated with antibody titrations (37 μL of 10× solution)±anti-αVβ5 (P1F6) ascites (Chemicon) (37 μL of 1:600 (10×)) for 15 min at 37° C. The cell-antibody mixture was added to the vitronectin-coated plates at 100 μL/well in triplicate (approximately $6 \times 10^5$ cells/well). Plates were incubated for 45 minutes at 37° C. Unbound cells were removed by two washes with HBSS/calcium (150 μL/well). 100 μl HBSS/calcium was added to each well and the plate read on the Fluoroskan at 485–538 nm.

In a separate assay, MDA-MB435-L2 human breast carcinoma cells were harvested with versene and suspended in serum free media at 500,000 cells/mL and incubated with various concentrations of GenO95. After 10 minutes of incubation tumor cell suspension (100 μL) was added to vitronectin (10 μg/mL) coated Linbro plates and incubated at 37° C. After 1 hour, wells were washed three times with serum free media (200 μL/wash) and the MTT based Cell Titer AQ dye (Promega, Madison, Wis.) was added to each well. Extent of cell adhesion was determined in an ELISA plate reader where OD490 nm is directly proportional to cell adhesion. Cell adhesion to BSA coated wells served as negative control.

Determination of $Ca^{++}$ Dependence for Binding of Anti-Human alphaVbeta3/alphaVbeta5 Mabs to Their Ligands To determine cation dependence in the binding of CNTO 95 and C372 to $\alpha_v\beta_3$ or $\alpha_v\beta_5$, a liquid phase EIA was utilized. EIA plates (Coming) were coated with CNTO 95, C372, c7E3 or LM609 IgG Mabs at 10 :g/mL in carbonate coating buffer overnight at 4EC. Plates were blocked with 1% BSA diluted in HBSS in the presence or absence of 2 mM $Ca^{++}$ for at least one hour at 37 EC. Doubling dilutions of alphaVbeta3 (log JG52599) or alphaVbeta5 (Chemicon) starting at 10 :g/mL were preincubated with 50 mM EDTA (Sigma) in 1% BSA/HBSS without $Ca^{++}$ or with 1% BSA/HBSS with $Ca^{++}$ for 30 minutes at 37° C. The mixtures were then added to the plates and incubated for 30 minutes at 37° C. The plates were then washed and non-competing Mabs were added to the plates as follows: to the CNTO 95, C372, c7E3 coated plates to detect alphaVbeta3 binding, Mab LM609 was added at 20 microgm/mL in 1% BSA/HBSS $Ca^{++}$; to the LM609 coated plate to detect alphaVbeta3 binding, Mab CNTO 95 was added at 20 :g/mL in 1% BSA/HBSS w $Ca^{++}$ to the CNTO 95, C372, c7E3 coated plates to detect alphaVbeta5 binding Mab VNR139 (Gibco) was added at 10 microg/mL in 1% BSA/HBSS w $Ca^{++}$ and incubated for 30 minutes at 37° C. The plates were again washed and probed with either HRP labeled goat anti-mouse IgG Fc or HRP labeled goat anti-human IgG Fc in appropriate buffer and incubated for 30 minutes at 37° C. The plates were washed, OPD substrate was added and the OD 490 measured as previously described.

Results and Discussion

Generation of Totally Human Anti-Human αVβ3 Integrin Monoclonal Antibodies

One fusion, named GenO, was performed from a GenPharm mouse immunized with alphaVbeta3 protein. From this fusion, 129 growth positive hybrids were screened. Two hybridoma cell lines were identified that secreted totally human IgG antibodies reactive with human alphaVbeta3. These two cell lines, CNTO 95.9.12 and GenO.101.17.22, each secrete immunoglobulins of the human IgG1κ isotype and both were subcloned twice by limiting dilution to obtain stable cell lines (>90% homogeneous). CNTO 95.9.12 was assigned C-code #C371A and GenO.101.17.22 was assigned C-code #C372A. Each of the cell lines was frozen in 12-vial research cell banks stored in LN2.

Binding Characteristics of Human Monoclonal Antibodies by EIA

Figure 1:
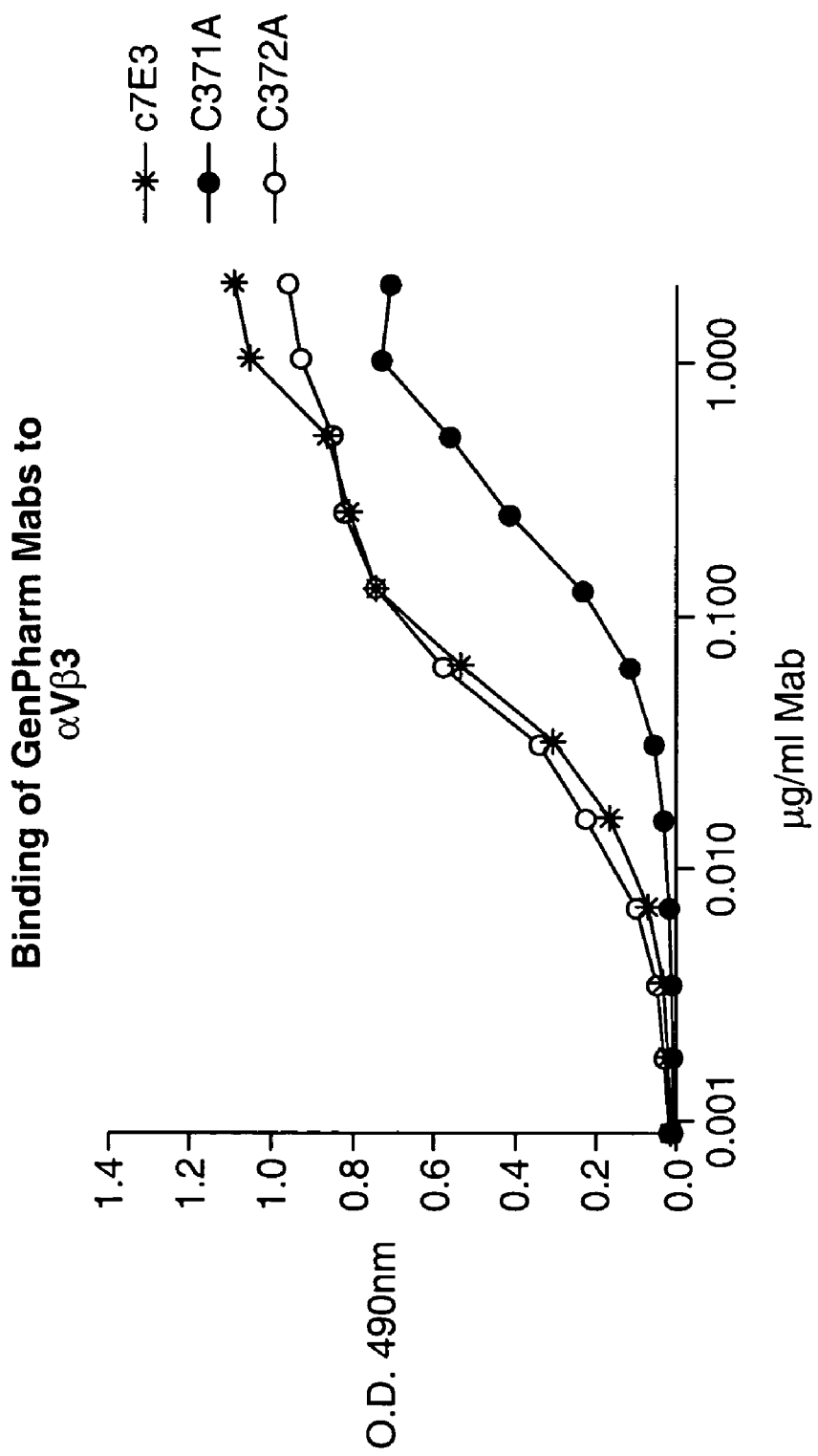
FIG. 1 shows a graph of doubling dilutions of anti-$\alpha V\beta 3$ Mabs which were incubated on $\alpha V\beta 3$ coated plates for 1 hour at RT. Plates were washed twice and probed with HRP labeled goat anti-human IgG kappa specific antibody for 1 hour at RT. Plates were again washed, developed with OPD substrate and OD's measured at 490 nm.

ELISA analysis confirmed that purified antibody from the two hybridomas, C371A (also called Mab CNTO 95) and C372A, bind alphaVbeta in a concentration-dependent manner. FIG. 1 shows the results of the relative binding efficiency of the antibodies. Fifty percent binding is achieved at 0.07 and 0.7 μg/mL for C372A and CNTO 95 respectively. In the same assay, c7E3 IgG demonstrated fifty-percent maximal binding at 0.07 μg/mL.

Competition of Binding of Mab CNTO95 to M21 Cells by Commercially Available Anti-Integrin Mabs By single-color analysis, none of the murine anti-alphaVbeta3, anti-alphaVbeta5, anti-beta3, or anti-alphaV antibodies competed with CNTO 95 for binding to M21 cells (Table 1). This experiment also demonstrates that CNTO 95 binds to M21 cells in a dose dependent manner. The two-color analysis demonstrated that the murine anti-alphaVbeta3, anti-alphaVbeta5, anti-beta3, or anti-alphaV antibodies were able to bind to M21 cells (data not shown).

TABLE 1

Competition of Binding of CNTO95 to M21 Cells by Murine anti-Integrin Mabs

| | FITC-goat anti-human Fc-labeled CNTO95 | | | |
|---|---|---|---|---|
| | 2 μg/mL | | 20 μg/mL | |
| Competing Antibody | MCF | % Positive | MCF | % Positive |
| negative (no GenO95) | 2.69 | | 2.69 | |
| Positive (saline) | 4.33 | 100% | 14.33 | 100% |
| m7E3 IgG | 5.73 | 132% | 14.72 | 103% |
| LM609 (anti-$\alpha_v\beta_3$) | 4.78 | 110% | 13.34 | 93% |
| anti-$\beta_3$ (Chemicon) | 5.42 | 125% | 13.10 | 91% |
| anti-$\beta_3$ (AMAC) | 4.61 | 106% | 13.10 | 91% |

TABLE 1-continued

Competition of Binding of CNTO95 to M21 Cells by Murine anti-Integrin Mabs

| | FITC-goat anti-human Fc-labeled CNTO95 | | | |
|---|---|---|---|---|
| | 2 µg/mL | | 20 µg/mL | |
| Competing Antibody | MCF | % Positive | MCF | % Positive |
| P1F6 (anti-$\alpha_v\beta_5$) | 4.87 | 112% | 14.46 | 101% |
| VNR139 (anti-$\alpha_v$) | 4.61 | 106% | 14.86 | 104% |

MCF = Median Channel Fluorescence

Figure 2:
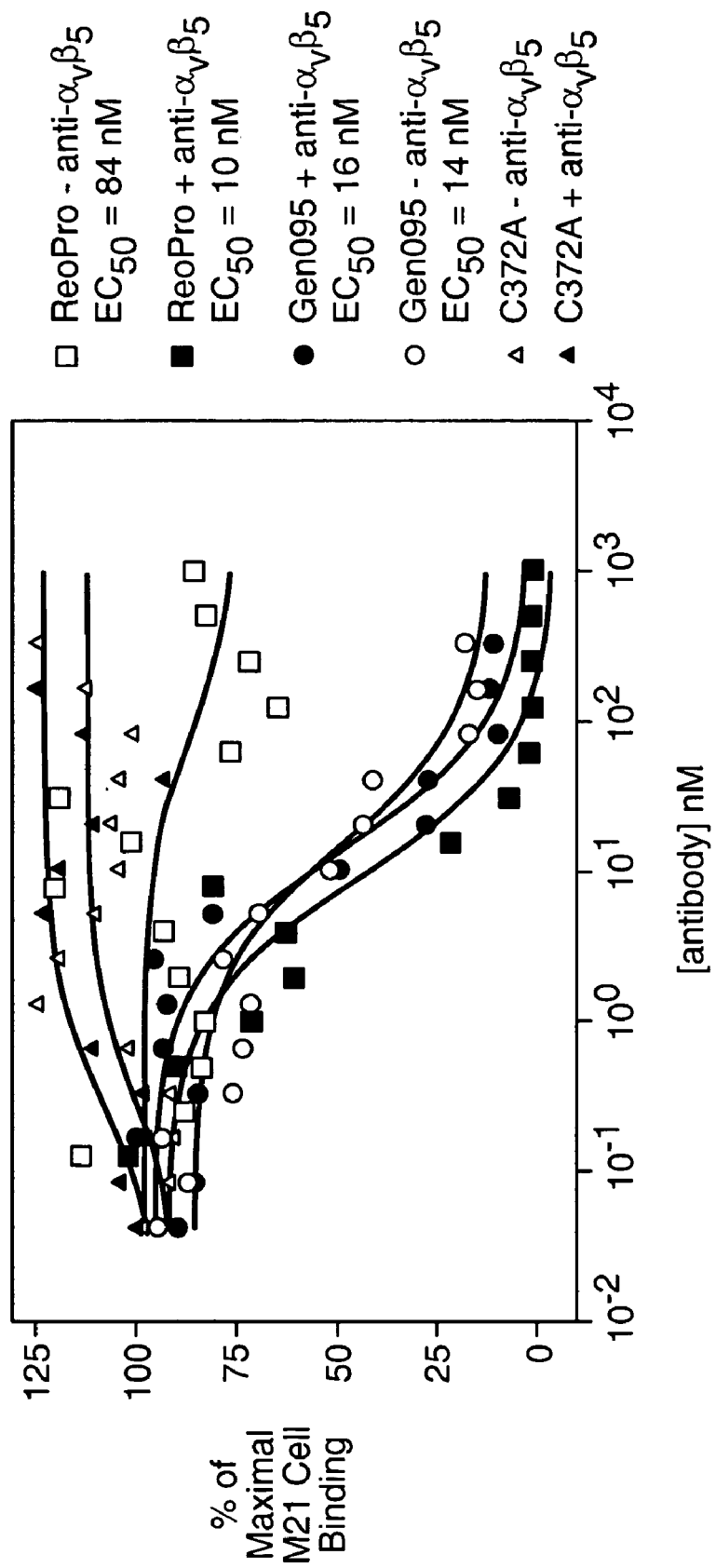
FIG. 2 shows a graph of calcein-labeled M21 cells which were preincubated with antibody samples in the absence or presence of P1F6, anti-$\alpha V\beta 5$ ascites for 30 minutes, then added to vitronectin coated plates for 45 minutes. Non-bound M21 cells were removed with two 150 μL/well washes with HBSS with calcium. Plate was read on a fluorometer at 485–538 nm.

Inhibition of $\alpha V\beta 3$ or $\alpha V\beta 5$ Dependent M21 Cell or MDA-MB435-L2 Cell Adhesion to Vitronectin Coated Plates by $\alpha V\beta 3/\alpha V\beta 5$ Specific Mabs M21 cells adhere to vitronectin coated plates in an $\alpha V\beta 3$ and $\alpha V\beta 5$ dependent manner. Therefore, blockade of both $\alpha V\beta 3$ and $\alpha V\beta 5$ is required to completely inhibit M21 cell adhesion to vitronectin coated plates. C372A did not inhibit M21 cell adhesion in the presence or absence of P1F6, anti-$\alpha V\beta 5$ ascites (FIG. 2). GenO95 (CNTO 95) completely inhibited M21 cell adhesion to vitronectin coated plates both with and without anti-$\alpha_v\beta_5$ (P1F6) ascites, indicating that the antibody blocks both $\alpha V\beta 3$ and $\alpha V\beta 5$. As a control for the assay parameters, ReoPro (c7E3 Fab) which blocks $\alpha V\beta 3$ (in addition to GPIIb/IIIa) was included. ReoPro alone only partially inhibited M21 cell adhesion, ReoPro in the presence of anti-$\alpha_v\beta_5$ (P1F6) ascites completely inhibited adhesion, which demonstrates that M21 cells bind to vitronectin through both $\alpha_v\beta_3$ or $\alpha_v\beta_5$ integrins. Data were normalized to percent of maximal M21 cell binding in the absence of antagonist +/− anti-$\alpha V\beta 5$ (PIF6) ascites. For antagonist titration without P1F6, data were normalized to maximal M21 cell binding in the absence of antagonist or P1F6. For antagonist titration in the presence of P1F6, data were normalized to maximal binding in the absence of antagonist but in the presence of P1F6. Data were graphed as percent of maximal binding (no antibody) and non-linear regression performed using GraphPad Prism.

Figure 3:
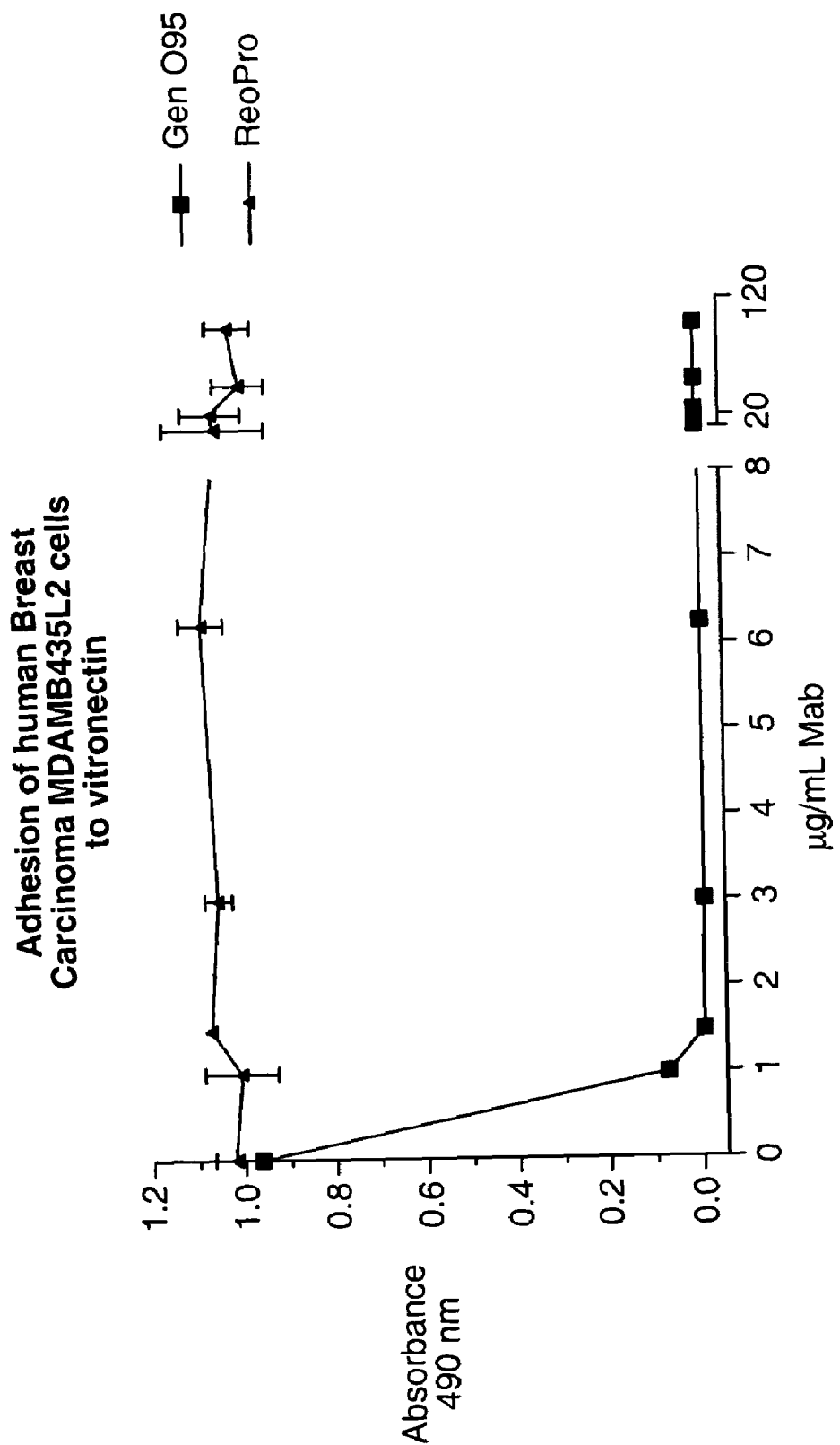
FIG. 3 shows a graph of cell adhesion where MDA MB 435L2 cells were harvested and pre-incubated with various concentrations of CNTO95 for 10 minutes. Tumor cells were then added to vitronectin coated Linbro plates and incubated at 37° C. for one hour. Wells were washed three times and the MTT based Cell Titer AQ dye was added to each well. Cell adhesion was determined in an ELISA plate reader where OD490 nm is directly proportional to cell adhesion. Cell adhesion to BSA coated wells served as negative control (data not shown). Each data point is the mean of triplicate determinations.

CNTO95 Mab also demonstrated the ability to completely inhibit MDAMB435L2 cell adhesion to vitronectin at a minimal concentration of 1.5 µg/mL (FIG. 3). These data, in combination with the data indicating inhibition of M21 cell adhesion, confirm the ability of GenO95 to functionally inhibit the $\alpha V\beta 3$ and/or $\alpha V\beta 5$ receptor interaction with vitronectin.

Figure 4A:
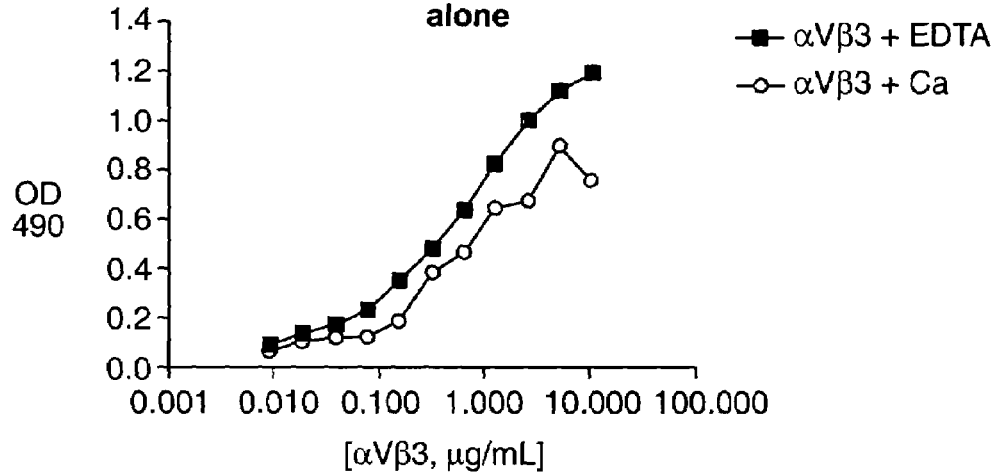
FIGS. 4A–D show graphs of antibody binding to $\alpha v\beta 3$ where this ligand was preincubated in doubling dilutions starting at 10 ug/mL with 50 mM EDTA in 1% BSA-HBSS (in the absence of Ca++) or with 1% BSA-HBSS (with Ca++) for 30 min, 37 EC. Mixtures added to plates coated with CNTO 95, C372, c7E3 or LM609 IgG and incubated for 1 hour, 37° C. LM609 or CNTO 95 added at 20:g/mL in appropriate buffer (+/−Ca++) for 30 min, 37° C. Plates probed with goat anti-mouse IgG Fc, HRP or goat anti-human IgG Fc, HRP.
Figure 4B:
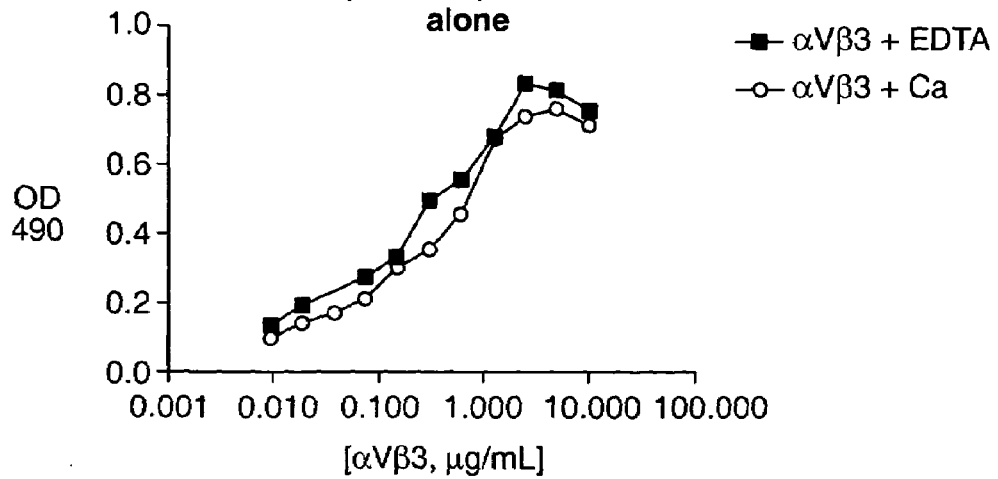
Figure 4C:
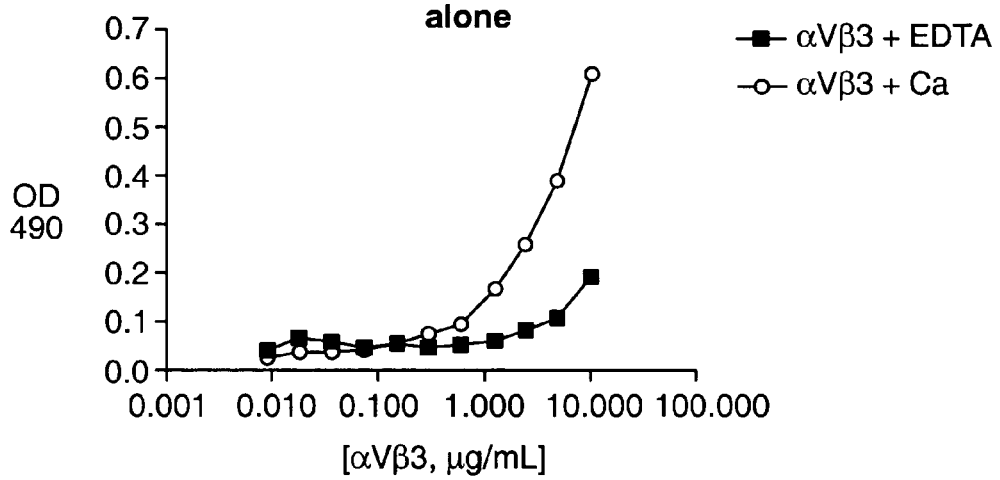
Figure 4D:
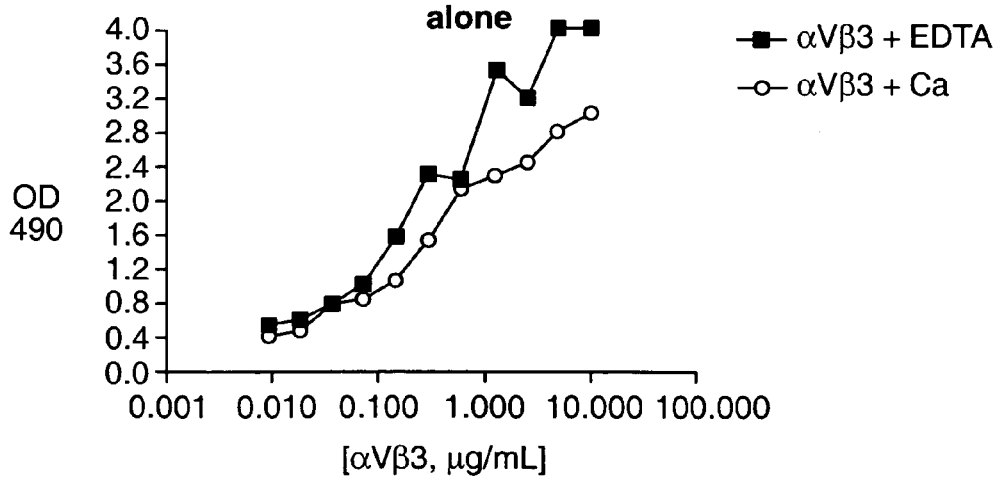
Figure 4E:
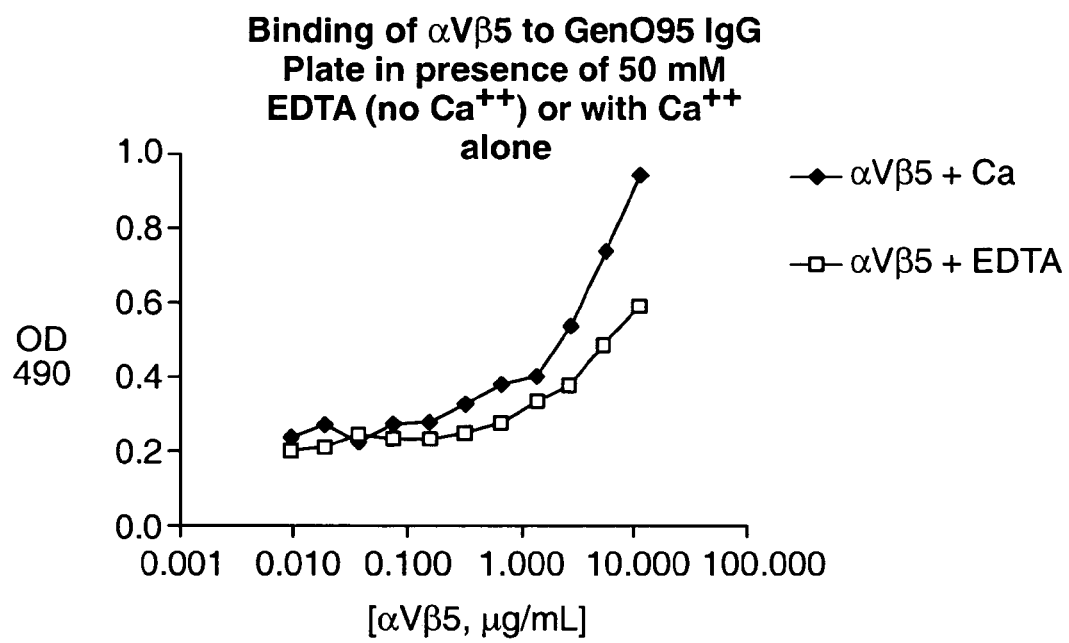
FIGS. 4E–G show graphs of antibody binding to a alphaVbeta5, where this ligand was preincubated in doubling dilutions starting at 10 ug/mL with 50 mM EDTA in 1% BSA-HBSS (in the absence of Ca++) or with 1% BSA-HBSS (with Ca++) for 30 min, 37° C. Mixtures added to plates coated with CNTO 95, C372, c7E3 IgG and incubated for 1 hour, 37° C. VNR139 was added at 10 mg/mL in appropriate buffer (+/−Ca++) for 30 min, 37° C. Plates probed with goat anti-mouse IgG Fc, HRP.
Figure 4F:
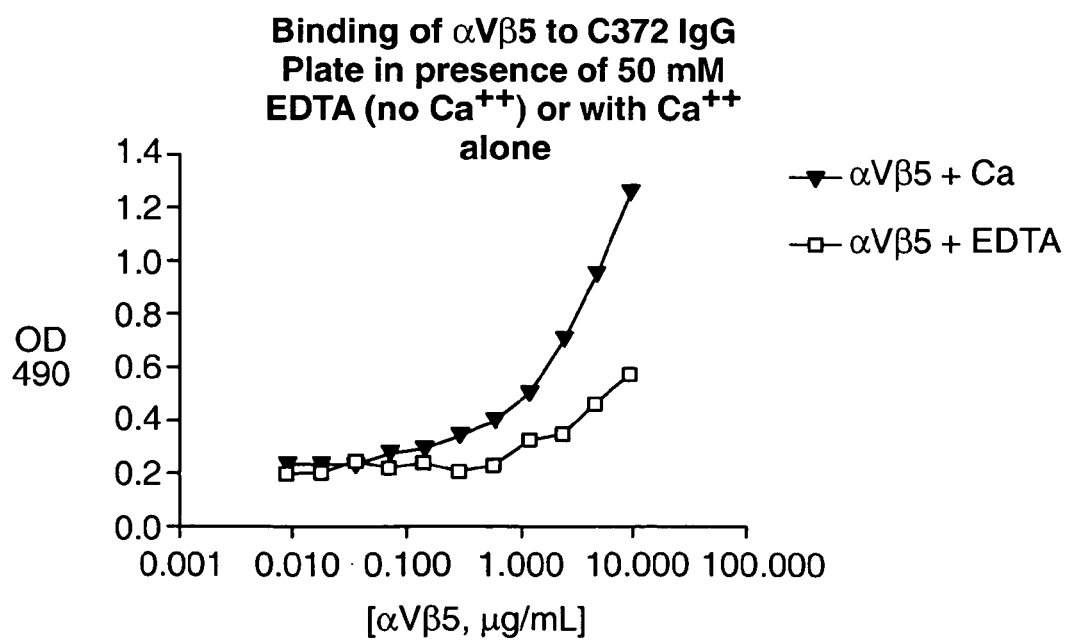
Figure 4G:
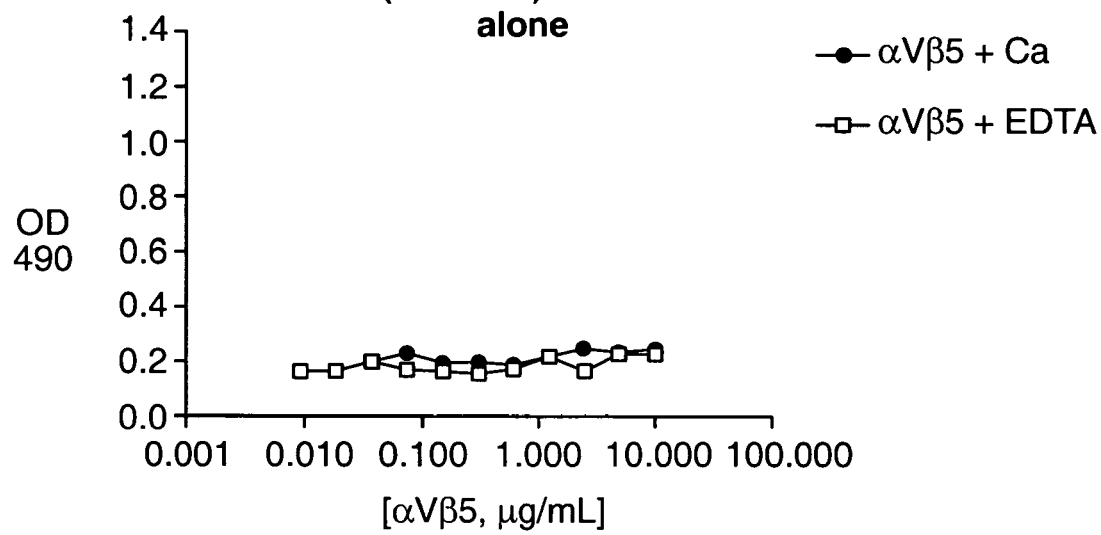

Determination of $Ca^{++}$ Dependence for Binding of Anti-Human alphaVbeta3/alphaVbeta 5 Mabs to Their Ligands It is known that the presence of the cation calcium is necessary for the Mab c7E3 to bind alphaVbeta 3 and is not a requirement for binding of Mab LM609 to $\alpha V\beta 3$ as demonstrated in FIGS. 4c and 4d respectively. This experiment was conducted to assess whether calcium dependence also applies to the binding characteristics of CNTO 95 or C372 for alphaVbeta 3 or alphaVbeta 5 integrins. An excess concentration of EDTA was introduced into the assay format to chelate the Ca present within the binding pocket of the integrin subunits and therefore, binding was assessed in the absence of the cation. It was found that CNTO 95 and C372 binding to alphaVbeta 3 is not dependent upon the presence of Ca (FIGS. 4a, 4b). The same is true for CNTO 95 binding to alphaVbeta 5 but not so, however, for C372 binding to alphaVbeta 5 (FIGS. 4e, 4f) as binding appears to be increased in the presence of Ca.

Conclusion

The GenO fusion was performed utilizing splenocytes from a hybrid mouse containing human variable and constant region antibody transgenes that was immunized with human $\alpha V\beta 3$. Two totally human $\alpha V\beta 3$ reactive IgG monoclonal antibodies of the IgG1κ isotype were generated. These Mabs were further characterized and it was found that both bind $\alpha V\beta 3$ and $\alpha V\beta 5$ integrins. The binding of the two Mabs was demonstrated to be calcium independent to $\alpha V\beta 3$ and calcium dependent to $\alpha V\beta 5$ only for C372 binding. Moreover, one Mab, GenO95 (CNTO 95), is able to completely inhibit the binding of $\alpha V\beta 3$ and $\alpha V\beta 5$ to the ligand vitronectin in cell based assays. This Mab may prove useful in anti-angiogenic and other cancer related applications.

REFERENCES

1. Taylor et al., International Immunology 6:579–591 (1993).
2. Lonberg et al., Nature 368:856–859 (1994).
3. Neuberger, Nature Biotechnology 14:826 (1996).
4. Fishwild et al., Nature Biotechnology 14:845–851 (1996).
5. Gastl et al., Oncology 54: 177–184 (1997).
6. Eliceiri, et al., J. Clin. Invest. 103: 1227–1230 (1999).
7. Friedlander et al., Science 270: 1500–1502 (1995).
8. Wayner, et al., J. Cell Biol. 113: 919–929 (1991).

EXAMPLE 3

Binding Affinities for Alpha-V Subunit Antibody

CNTO 95, (CNTO 95) as described in Example 2, is a human monoclonal antibody generated by immunizing (CBA/J×C57/BL6/J, GenPharm International) F2 hybrid mice with $\alpha_v\beta_3$ integrin purified from human placenta. The antibody is composed of human variable and IgG1 kappa constant regions and found to be reactive to both $\alpha_v\beta_3$ and $\alpha_v\beta_5$, suggesting a specificity for the alpha chain shared by both integrin molecules.

The purpose of this study is to characterize the binding affinity of GenO.05 for $\alpha_v\beta_3$ and $\alpha_v\beta_5$ purified integrins and for beta integrin expressing cell lines. For further characterization, the binding values will be compared between CNTO 95 and ReoPro.

Abbreviations $K_D$, equilibrium dissociation constant, expressed in M

Bmax=maximal number of binding sites

Materials And Methods

Cell Lines

A375S2 cells, a human melanoma cell line expressing $\alpha_v\beta_3$ and $\alpha_v\beta_5$ integrins, were cultured in Dulbelcco's minimal media (DMEM) containing 10% fetal bovine serum (FBS, Cell Culture Labs), 1 mM sodium pyruvate, 0.1 mM nonessential amino acids, and 2 mM L-glutamine (all from JRH Biosciences).

HT29 cells, a human colon carcinoma cell line expressing $\alpha_v\beta_5$ and minimal $\alpha_v\beta_3$ (NB 4546, p207) were cultured in DMEM containing 10% FBS, 1 mM sodium pyruvate, 0.1 mM nonessential amino acids, and 2 mM L-glutamine.

M21 cells, a human melanoma expressing $\alpha_v\beta_3$ and $\alpha_v\beta_5$ integrins, obtained from Dr. J. Jakubowski (Eli Lilly, Inc.), were cultured in RPMI media (JRH Biosciences) containing 10% FBS, 1 mM sodium puruvate, 0.1 mM nonessential amino acids, and 2 mM L-glutamine.

Integrins

α$_v$β$_3$ lot JG22499 was purified at Centocor from human placenta. Another α$_v$β$_3$ integrin lot (octyl formulation, lot 19100991) was purchased from Chemicon. α$_v$β$_5$ (Triton formulation, lot 20030055, lot 1910990 and octyl formulation, lot 19060747) was purchased from Chemicon.

Antibodies

CNTO 95 was purified from cell culture supernatant by Protein A chromatography. ReoPro was manufactured at Centocor, Inc. LM609, a murine anti-human α$_v$β$_3$ antibody, (1976ZK, lot 20020559 and lot 1910329) and P1F6, a murine anti-human α$_v$β$_5$ antibody (1961 P-K, lot 17110560) were purchased from Chemicon.

Radiolabeling

Antibodies were radiolabeled with 125-I Na (Amersham, IL) using Iodobeads (Pierce Chemicals, IL) to a specific activity of 1–2 μCi/μg. Antibody concentration (mg/ml) was determined by dividing the adsorption (OD/ml) at 280 nm by 1.4. Specific activity of the iodinated antibody was determined by diluting the antibody and counting an aliquot in the gamma counter or Topcounter (Packard).

Specific activity (cpm/ug)=cpm/volume (ml)×dilution factor concentration (μg/ml determined by OD$_{280}$ reading)

Integrin-coated plate binding assay

α$_v$β$_3$ or α$_v$β$_5$ integrin was diluted to 1 μg/ml in Tris-buffered saline (TBS, 10 mM Tris, 100 mM NaCl, pH 7.5) containing 2 mM calcium chloride (TBS/Ca$^{++}$) and coated at 50 μl per well onto 96 well polystyrene Linbro plates (Flow/ICN) overnight at 4° C. Plates were washed with TBS/Ca$^{++}$ and blocked with 1% bovine serum albumin (BSA) in TBS/Ca$^{++}$ for 1 h at room temperature. Fifty microliters of diluted antibody was added in triplicate to coated wells and incubated for 2 h at 37° C. After three washes with TBS-Tween buffer (TBS+0.1% Tween 20), peroxidase conjugated goat anti-human IgG F(ab')$_2$ (H+L, Jackson lot 16869), at 1:40:000 dilution in 1% BSA-TBS was added and incubated for 1 h at room temperature. Plates were washed three times, and developed with o-phenylenediamine dihydrochloride substrate solution (OPD, Sigma) consisting of 0.1 M citric acid, 0.2M sodium phosphate, 0.01% H$_2$O$_2$ and 1 mg/ml OPD. Color development was stopped after 15 min at room temperature with 0.3 N H$_2$SO$_4$, and plates were read at OD$_{490}$ nm in the Molecular Dynamics plate reader.

Binding curves were generated with GraphPad PRISM (version 3, GraphPad Software). Results were expressed as % maximal binding of the saturation value. K$_D$, the equilibrium dissociation binding constant (expressed as M), was determined from a non-linear regression fit of the data using PRISM.

Cell Binding Assay

Fifty microliters of diluted radiolabeled antibody in 2% RPMI media containing 2% bovine serum albumin (JRH Biosciences) were added in triplicate to confluent cells cultured in 96 well tissue culture plates (Packard). Cells were incubated for 1.5 h at 37° C.; gently washed three times with Hanks buffered saline containing calcium and magnesium (HBSS++, JRH Biosciences) and then aspirated. One hundred microliters of Mycosinct 20 (Packard) was added per well, and cell-bound radioactivity was quantified in the TopCounter (Packard).

To determine nonspecific binding, experiments were performed with a similar set of dilutions in the presence of 100-fold excess of unlabeled antibody.

To determine the number of cells plated in each well, cells from several wells were removed with trypsin, pooled and counted under the microscope. The receptor number per cell was calculated as follows:

Receptor number/cell=specific bound cpms×6.023×10$^{23}$ molecules/mole specific activity (cpm/g)×mol. wt. (g/mole)×cell number Bmax, the maximal binding sites per cell, and the K$_D$ were determined from a nonlinear regression fit of the data using PRISM.

Results and Discussion

Determination of the binding affinity values was performed by measuring the binding of various concentrations of CNTO 95 (and ReoPro) to purified α$_v$β$_3$ and α$_v$β$_5$ integrins and to cell surface receptors at equilibrium. The saturation binding curves were rectangular hyperbolas, suggesting a single receptor binding site for CNTO 95 and ReoPro (FIGS. 5–6; Motulsky H, 1999). Analysis of these saturation binding data (sometimes called Scatchard experiments) were performed using a one-site hyperbola nonlinear regression fit in PRISM to obtain an affinity, K$_D$, and receptor number, Bmax (Motulsky H, 1999).

Several lots of CNTO 95, ReoPro and purified integrins were used to ensure an accurate determination of binding affinity values. The saturation binding curve of CNTO 95 on an α$_v$β$_3$ coated plate (FIG. 5A) and the binding curve of ReoPro on an α$_v$β$_3$ coated plate (FIG. 5B) represent the mean and standard deviation of six separate experiments. Results obtained with Triton formulation of α$_v$β$_3$ were found to be more reproducible than those obtained from the octyl formulation. On α$_v$β coated plates, the CNTO 95 mean K$_D$ was 2.1±1.33×10$^{-10}$M; and the mean ReoPro Kd was 2.5±1.46×10$^{-10}$M.

The saturation binding curve of CNTO 95 on an α$_v$β$_5$ coated plate (FIG. 6A) and the binding curve of ReoPro on an α$_v$β$_5$ coated plate (FIG. 6B) are shown as the mean and standard deviation of six separate experiments. Results obtained with the octyl formulation were more consistent than those obtained with the Triton formulation. The CNTO 95 mean K$_D$ on α$_v$β$_5$ was 2.5±1.04×10$^{-11}$ M. ReoPro showed no binding and no dose-response on α$_v$β$_5$ coated plates.

The binding affinity values for purified integrins were compared to binding to receptors expressed on various cell lines. FIG. 7A–C shows the binding of 125-I CNTO 95 with A375S2 cells which express α$_v$β$_3$ and α$_v$β$_5$ (FIG. 7A). Mean affinity values on A375S2 cells were: Kd=5.2±2.04×10$^{-9}$ M; and 120,000±37,000 receptors/cell. HT-29 cells express α$_v$β$_5$. Affinity values for 125-I CNTO 95 binding to HT-29 cells were: Kd=1.3±3.76×10$^{-10}$ M; and 81,000±24,000 receptors/cell (FIG. 7B). M21 cells express α$_v$β$_3$ and α$_v$β$_5$ integrins. 125-I CNTO 95 binding to M21 celllls were: Kd=8.5±3.03×10$^{-9}$ M; and 200,000±80,000 receptors/cell (FIG. 7C).

Similar cell binding studies were performed with 125-I ReoPro on various cell lines. FIG. 8A–C shows the binding of 125-I ReoPro with A375S2 cells and the mean values obtained were: Kd=22±3.7×10$^{-9}$ M; and 370,000±190,000 receptors/cell (FIG. 8A). On HT-29 cells, 125-I ReoPro showed minimal binding (FIG. 8B). 125-I ReoPro binding to M21 cells showed: Kd=10±2.00×10$^{-9}$ M and 660,000±120,000 receptors/cell (FIG. 8C). The binding values of 125-I ReoPro on M21 cells are consistent with values previously published (Tam et al, 1998).

A summary of binding results is shown in Tables 2–3.

TABLE 2

Summary of CNTO 95 and abciximab
affinities to purified integrins

| mAb | alphaVbeta 3 coated plate (n = 6) Kd (M) | alphaVbeta 5 coated plate (n = 6) Kd (M) |
|---|---|---|
| CNTO 95 | $2.1 + 1.33 \times 10^{-10}$ | $2.5 + 1.04 \times 10^{-11}$ |
| abciximab | $2.5 + 1.46 \times 10^{-10}$ | Negligible |

TABLE 3

Summary of CNTO 95 and abciximab affinities to cells

| | A375S2 cells Kd (M) | A375S2 cells Receptors percell | HT-29 cells Kd(M) | HT-29 cells Receptors per cell | M21 cells Kd (M) | M21 cells Receptors per cell |
|---|---|---|---|---|---|---|
| CNTO 95 | $5.2 \pm 2.04 \times 10^{-9}$ (n = 5) | $120,000 \pm 37,000$ (n = 7) | $1.3 \pm 0.38 \times 10^{-9}$ (n = 5) | $81,000 \pm 24,000$ (n = 7) | $8.5 \pm 3.03 \times 10^{-9}$ (n = 4) | $200,000 \pm 80,000$ (n = 8) |
| abciximab | $22 \pm 3.7 \times 10^{-9}$ (n = 3) | $370,000 \pm 190,000$ (n = 6) | Negligible (n = 4) | Negligible (n = 4) | $10 \pm 2.00 \times 10^{-9}$ (n = 3) | $660,000 \pm 120,000$ (n = 7) |
| anti $\alpha_v\beta_3$ LM609 | nd | 300,000 (n = 2) | nd | nd | nd | nd |
| anti-$\alpha_v\beta_5$ PIF6 | nd | $70,000 \pm 50,000$ (n = 4) | nd | 73,000 (n = 1) | nd | 44,000 (n = 2) |

Several observations were notable in the binding characterizations. Affinity values (Kd) of CNTO 95 on $\alpha_v\beta_5$ were lower than on $\alpha_v\beta_3$. Lower Kd values indicate a higher affinity; thus the affinity for CNTO 95 binding to $\alpha_v\beta_5$ purified integrin was about 8-fold higher than binding to $\alpha_v\beta_3$ purified integrin. However, when both integrin receptors are present on the same cells, the overall affinity value more closely approximates the value corresponding to the integrin in greater abundance. Thus, on A375S2 and M21 cells where there is more $\alpha_v\beta_3$ than $\alpha_v\beta_5$, the affinity of CNTO 95 binding to these cells was similar to the affinity on $\alpha_v\beta_3$, $\sim 7\times 10^{-9}$ M. In contrast, on HT-29 cells which express $\alpha_v\beta_5$, the CNTO 95 affinity was slightly higher, $1\times 10^{-9}$ M. The approximately 2-fold discrepancy in receptor sites per cell between CNTO 95 and ReoPro binding may be explained by the difference in antibody valency. CNTO 95 (IgG) is bivalent and likely binds two adjacent receptors, whereas ReoPro (Fab) is monovalent and can only bind to one receptor (BRD930001).

REFERENCES

Fraker D J, Speck J C. Protein and cell membrane iodination with a sparingly soluble chloramide 1,3,4,5-tetrachloro-3a-diphenyl-glycoluril. *Biocheem Biophys Res Commun.* 80:849, 1978.
Motulsky H. *Analyzing Data with GraphPad Prism.* Graph-Pad Software, Inc. San Diego, Calif. 1999.
Tam S H, Sassoli P M, R Jordan, M T Nakada. *Circulation*, 1999.

EXAMPLE 4

Effect of Alpha-V Subunit Antibody on Angiogenesis Modulation

GenO95 is a human IgG1κ monoclonal antibody that recognizes integrins $\alpha_v\beta_3$ and $\alpha_v\beta_5$ as well as $\alpha_v\beta_1$ and $\alpha_v\beta_6$. These integrins participate in endothelial cell adhesion, migration, survival and proliferation, processes that are important for angiogenesis. Endothelial cell sprouting mimics angiogenesis in vitro because it involves cell adhesion, migration, proliferation and survival. We utilized the sprouting assay to determine whether GenO95 could inhibit $\alpha_v\beta_3$ and $\alpha_v\beta_5$ function. This example describes that GenO95 is an inhibitor of sprouting of endothelial cells that are cultured in three dimensional fibrin matrix, thereby demonstrating that this antibody may have potential anti-angiogenic properties.

There is now considerable evidence that progressive tumor growth is dependent upon angiogenesis, the formation of new blood vessels. These blood vessels provide tumors with nutrients and oxygen, carry away waste products and act as conduits for the metastasis of tumor cells to distant sites (1). Recent studies have further defined various roles of integrins in the angiogenic process. Integrins are subunitic transmembrane proteins that play an important role in mediating cell adhesion, migration, survival, and proliferation (2). Expression of integrin αvβ3 is minimal on resting or normal blood vessels but is significantly up-regulated on angiogenic vascular cells (1–3). The closely related but distinct integrin αvβ5 has also been shown to mediate the angiogenic process. An antibody generated against αvβ3 blocked basic fibroblast growth factor (bFGF) induced angiogenesis, whereas an antibody specific to αvβ5 inhibited vascular endothelial growth factor (VEGF) induced angiogenesis (1–5).

Angiogenesis can be mimicked in vitro by an endothelial sprouting assay. This system involves endothelial cell migration and proliferation. GenO95 is a human monoclonal antibody that recognizes integrins αvβ3 and αvβ5, and these integrins regulate endothelial cell migration and proliferation. Therefore, we determined whether GenO95 could inhibit sprouting of endothelial cells. This example describes experiments that demonstrate that GenO95 inhibits sprouting of human endothelial cells growing in a fibrin matrix.

Materials

Human basic fibroblast growth factor (bFGF) and human vascular endothelial growth factor 165 ($VEGF_{165}$) were obtained from R&D Systems (Minneapolis, Minn.). MAB 1976Z (LM609), a monoclonal antibody against integrin αvβ3 and MAB1961 (PIF6), a monoclonal antibody against integrin αvβ5 were purchased from Chemicon (Temecula, Calif.). ReoPro and GenO95 were obtained from Centocor's Clinical Pharmacology and Antibody Technology Department. Human fibrinogen (plasminogen free, >95% clottable protein) and bovine skin gelatin were purchased from Sigma (Saint Louis, Mich.).

Cell Lines

Huvecs, Human umbilical vein endothelial cells, were purchased from Clonetics (Walkersville, Mass.). Huvecs were cultured in endothelial basal media (EBM) kit (Clonetics) containing 10% FBS, long R insulin-like growth factor-1, ascorbic acid, hydrocortisone, human epidermal growth factor, human vascular endothelial growth factor, hFGF-b, gentamicin sulfate, and amphotericin-B. Cells were incubated at 37° C. and 5% $CO_2$ and media was changed every 2 to 3 days. Only passages 3 to 8 were used in all experiments.

Fibrin Microcarrier-based Sprouting Assay

A modification of the methods of Nehls and Drenckhahn (6) was used to measure capillary tube formation in three-dimensional fibrin-based matrix. Gelatin-coated cytodex-3 microcarriers (MCs, Sigma) were prepared according to recommendations of the supplier. Freshly autoclaved MCs were suspended in EBM-2+20% FBS and endothelial cells were added to a final concentration of 40 cells/MC. The cells were allowed to attach to the MCs during a 4-hour incubation at 37° C. The MCs were then suspended in a large volume of medium and cultured for 2 to 4 days at 37° C. in 5% $CO_2$ atmosphere. MCs were occasionally agitated to prevent aggregation of cell coated beads. MCs were embedded in a fibrin gel that was prepared as follows: human fibrinogen (2 mg/ml) was dissolved in plain, bFGF or serum containing EBM-2 media. This solution also contained various antibodies. To prevent excess fibrinolysis by fibrin-embedded cells, aprotinin was added to the fibrinogen solution and to growth media at 200 U/ml. Cell-coated microcarriers were added to the fibrinogen solution at a density of 100 to 200 MCs/ml (50–100 beads/per well-48 well plate) and clotting was induced by addition of thrombin (0.5 U/ml). After clotting was complete, 0.5 ml solution (containing all components described above except fibrinogen and thrombin) was added to the fibrin matrices. The plates were incubated at 37° C. and 5% $CO_2$ for 1 to 3 days. After 1–3 days, gels were fixed with 3% paraformaldehyde dissolved in PBS, and the number of capillary sprouts with length exceeding the diameter of the MC bead (150 µm) was quantified.

Results and Discussion

Huvecs can form capillary-like sprouts when cultured in a fibrin gel (FIG. 9). Endothelial cells migrate outwards from the gelatin coated beads and extend into long filopodia. The long sprouts consist of several cells forming a lumen. This process resembles microcapillary formation in vivo, because it involves endothelial cell migration, invasion and cell proliferation. Quantification of sprout formation revealed that GenO95 inhibited endothelial cell sprout formation in bFGF or complete media (FIG. 10). Combination of LM609 and P1F6 routinely inhibited sprouting more effectively than GenO95 (FIG. 11).

Conclusion

Formation of new blood vessels from existing blood vessels is a hallmark of angiogenesis. This process can be mimicked in vitro by the endothelial sprouting assay. These sprouts represent microcapillaries that are formed in response to angiogenic stimuli such as bFGF or a variety of stimuli that are present in serum. GenO95 dose dependently inhibited bFGF- and complete media-stimulated endothelial cell sprouting, suggesting that this antibody can effectively inhibit αvβ3 and αvβ5 function. Why GenO95 was not as effective as the combination of LM609 and P1F6 is unknown, but it is possible that GenO95 recognizes αvβ3 and αvβ5 with lower affinity when compared to LM609 and P1F6, respectively. Collectively, these data demonstrate that GenO95 can inhibit the complex process of microcapillary formation in vitro.

REFERENCES

1. Gastl G, Hermann T, Steurer M, Zmija J, Gunsilius E, Unger C, and Kraft A. 1997. Angiogenesis as a Target for Tumor Treatment. *Oncology* 54:177–184.
2. Eliceiri B P, and Cheresh D A. 1999. The role of αV integrins during angiogenesis: insights into potential mechanisms of action and clinical development. *The Journal of Clinical Investigation* 103:1227–1230.
3. Brooks P C, Montgomery A M, Rosenfeld M, Reisfeld R A, 1994. Integrin αvβ3 antagonists promote tumor regression by inducing apoptosis of angiogenic blood vessels. *Cell* 79: 1157–1164.
4. Enenstein J, Walweh N S, and Kramer R H. 1992. Basic FGF and TGF-β differentially modulate integrin expression of human microvascular endothelial cells. *Exp. Cell Res.* 203:499–503.
5. Friedlander M, Brooks P C, Shaffer R W, Kincaid C M, Varner J A, and Cheresh D A. 1995. Definition of two angiogenic pathways by distinct αV integrins. *Science* 270:1500–1502.
6. Nehls, V and Drenckhahn, D. 1995. A novel, microcarrier-based in vitro assay for rapid and reliable quantification of three-dimensional cell migration and angiogenesis. *Microvascular Res.* 50:311–322.

EXAMPLE 5

Effect of Alpha-V Subunit Antibody on Endothelial and Tumor Cell Adhesion, Migration and Invasion (CBA/J×C57/BL6/J) $F_2$ hybrid mice (1–4) containing human variable and constant region antibody transgenes for both heavy and light chains were immunized with human placental αvβ3. One fusion yielded a totally human αVβ3 reactive IgG1κ monoclonal antibody named GenO95. The totally human antibody was found to be reactive to the αVβ3 and αVβ5 integrins (5). These integrins participate in endothelial and tumor cell adhesion, migration, and invasion. Therefore, we characterized the effect of CNTO 95 on integrin mediated cell motility. CNTO 95 inhibits human umbilical vein endothelial (HUVEC) and human melanoma cell binding to vitronectin, denatured collagen, fibrinogen and fibrin, but it does not block cell adhesion to fibronectin and type I collagen. GenO95 also inhibits migration of endothelial cells that have been stimulated with basic fibroblast growth factor and low-dose serum. GenO95 inhibits invasion of tumor cells through a fibrin gel. In conclusion, GenO95 functionally blocks αVβ3 and αVβ5 in a variety of cell-based assays in vitro.

Abbreviations

BSA—bovine serum albumin
$CO_2$—carbon dioxide
DMSO—dimethyl sulfoxide
FBS—fetal bovine serum
Ig—immunoglobulin
Mab—monoclonal antibody
OD—optical density
RT—room temperature
HUVECS—human umbilical vein endothelial cells
bFGF—bovine basic fibroblast growth factor Introduction There is now considerable evidence that progressive tumor growth is dependent upon angiogenesis. The formation of new blood vessels provide tumors with nutrients and oxygen, carry away waste products and act as conduits for the spread of tumor cells to distant sites. Several studies have defined the role of integrins in the angiogenic process. Integrins are subunitic trans-membrane proteins that play a critical role in cell adhesion to the extracellular matrix (ECM) and mediate cell survival, proliferation and migration (6). During the angiogenic process, αvβ3 and αvβ5 are upregulated on the surface of activated endothelial cells, which in turn helps these cells to migrate and proliferate (6). An antibody generated against αVβ3 blocks basic fibroblast growth factor (bFGF) induced angiogenesis, whereas an antibody specific to αVβ5 inhibits vascular endothelial growth factor (VEGF) induced angiogenesis (6,7). In addition to regulating angiogenesis, αVβ5 and αVβ3 regulate tumor cell adhesion, migration and invasion, processes required for tumor cell metastases. Previous studies indicated that CNTO 95 binds to purified αVβ5 and αVβ3 integrins, therefore, we determined whether this antibody could functionally block αVβ3- and αVβ5-mediated endothelial and tumor cell adhesion, migration and invasion.

Materials and Methods

Materials

Bovine fibroblast growth factor (bFGF) and human vascular endothelial growth factor 165 ($VEGF_{165}$) were obtained from R&D Systems (Minneapolis, Minn.). MAB 1976Z (LM609), a monoclonal antibody against integrin αvβ3 and MAB1961 (PIF6), a monoclonal antibody against integrin αvβ5 were purchased from Chemicon (Temecula, Calif.). ReoPro (lot: 94A04ZE) and CNTO 95 (lot: JG100899) were obtained from Centocor. BIOCOAT cell culture inserts (pore size: 8 μm) were purchased from Becton Dickinson (Bedford, Mass.). Vybrant™ cell adhesion assay kit (V-13181) was purchased from Molecular Probes (Eugene, Oreg.). Human plasminogen free fibrinogen (VWF/Fn depleted) was purchased from Enzyme Research Labs (South Bend, Ind.). Bovine skin gelatin was purchased from Sigma (Saint Louis, Mo.). Human vitronectin was purchased from Promega (Madison, Wis.), and type I collagen was purchased from GIBCO BRL (Gaithersburg, Md.).

Cell Lines

Human umbilical vein endothelial cells (HUVECS), were purchased from Clonetics (Walkersville, Mass.), and they were cultured in EBM medium kit (Clonetics) containing 10% FBS, long R insulin-like growth factor-1, ascorbic acid, hydrocortisone, human epidermal growth factor, human vascular endothelial growth factor, gentamicin sulfate and amphotericin-B. Cells were grown at 37° C. and 5% $CO_2$ and media was changed every 2 to 3 days. Cells were passaged when they reached 80% confluence. Passages 3 to 8 were used in all experiments.

The A375S.2 human melanoma cell line expressing the αVβ3 and αVβ5 integrins was obtained from Centocor Cell Bank where the cell line was deemed free of mycoplasma and bacterial contaminants. The cells were cultured in DMEM medium supplemented with 10% FBS, 2 mM L-glutamine, 1 mM sodium pyruvate, and 0.1 mM non-essential amino acids.

Human colon carcinoma HT29 cells were obtained from Centocor Cell Biology Service Department, where the cell line was deemed free of mycoplasma and bacterial contaminant. The cells were cultured in α-MEM medium supplemented with 10% FBS, 2 mM L-glutamine, 1 mM sodium pyruvate, and 0.1 mM nonessential amino acids.

Flow Cytometry

For the detection of surface integrins, cells were harvested, rinsed, suspended in unsupplemented RPMI media, and sequentially incubated for 60 minutes on ice with anti-integrin mAb (10 ∞g/ml) and FITC-labeled goat anti-mouse antibody (1:100) or FHTC-labeled anti-integrin antibody (10 μg/ml). Absence of primary antibody or substitution of primary antibody with isotype matched antibody served as negative controls. Cells were immediately analyzed with a FACS Scan II flow cytometer (Becton Dickinson, Mountain View, Calif.).

Adhesion Assay

Microtiter plates (Linbro-Titertek, ICN Biomedicals, Inc) were coated at 4° C. overnight with vitronectin (1 μg/ml), gelatin (0.1%), fibrinogen (100 μg/ml), type I collagen (10 μg/ml), or fibronectin (10 μg/ml). Immediately before use plates were rinsed with PBS and blocked for 1 hour with 1% BSA/PBS (pH 7.4). Fibrin-coated Microtiter wells were formed by thrombin treatment (1 U/ml) of fibrinogen. Adherent cells (HUVECS HT29 and A375S.2) were labeled with Calcein AM fluorescent dye (Molecular Probes, Eugene, Oreg.) according to the manufacturer's instructions, harvested, washed twice, and suspended in 0.1% BSA in DMEM medium. After cell density was adjusted to $5 \times 10^5$/ml, cells were incubated with various concentrations of antibodies for 15 min at 37° C. The cell-antibody mixture was added to wells (100 μl per well).and incubated for 1 h at 37° C. Plates were rinsed twice with PBS to remove unbound cells and adhesion was measured in a fluorescence plate reader (Fluoroskan) at 485–538 nm. Cell adhesion to BSA-coated wells served as a negative control. Isotype matched antibodies served as a negative control.

Chemotactic Migration Assay

Cell migration assays were performed in 24-Transwell chambers with a polystyrene membrane (6.5 mm diameter, 10 μm thickness, and a pore size of 8 μm). Sub-confluent 24-hr cell cultures (HUVECS or A375S.2) were harvested with trypsin-EDTA, washed twice, and resuspended in their respective serum free medium containing 0.1% BSA. Cells (100,000/500 μl) were added to the upper chamber in the presence or absence of antibodies. To facilitate chemotactic cell migration, 750 μl of medium containing 0.1% BSA and vitronectin (2 μg/ml) or serum (2% for HUVECS and 10% for A375S2 cells) was added to the bottom chambers and the plate was placed in a tissue culture incubator. Migration was terminated after 4 to 8 hrs by removing the cells on the top with a cotton swab and then the filters were fixed with 3% paraformaldehyde and stained with Crystal Violet. The extent of cell migration was determined by light microscopy and images were analyzed using the Phase 3 image analysis software (Glen Mills, Pa.). The software analyzes the total area occupied by the stained cells on the bottom side of the filter and this is directly proportional to the extent of cell migration.

Haptotactic Migration Assay

Cell migration assays were performed using the transwell chambers as described above with slight modifications. Briefly, the underside of the membrane was coated with vitronectin (2 μg/ml) for 60 minutes at room temperature, and then blocked with a solution of 1% BSA/PBS at room temperature for 60 min. Next, membranes were washed with PBS and air dried. Serum free medium (750 μl) containing 0.1% BSA and bFGF (20 ng/ml) was added to the lower chambers. Sub-confluent 24 h cultures were harvested with trypsin-EDTA, washed twice, and resuspended in serum free medium. Cells (100,000/500 μl) were added to the upper chambers in the presence or absence of antibodies. The chambers were placed in a tissue culture incubator and migration was allowed to proceed for 6 h. Extent of cell migration was determined as described above.

Invasion Assay

Fibrinogen (Plasminogen-free, 100 μl of 10 mg/ml) and 100 μl of 1 U/ml thrombin was mixed and immediately added to the top chamber of 24 well transwell plates (6.5 mm diameter, 10 μm thickness and a pore size of 8.0 μm, Costar). The plates were incubated at 37° C. for 30 minutes to form a fibrin gel. Confluent tumor cells (A375S.2) were trypsinized, centrifuged, resuspended in basal medium supplemented with 0.1% BSA and 10 μg/ml plasminogen (Enzyme Research Labs, South Bend, Ind.) with various concentrations of antibodies, and incubated for 15 minutes at room temperature. Cells (100,000/500 μl) were added to the upper chamber in the presence or absence of antibodies. The lower compartment of the invasion chamber was filled with 0.75 ml of 10% FBS-DMEM, which served as a chemoattractant and the plate was transferred to a tissue culture incubator. After 24 hours, invasion was terminated by removing the cells on the top with a cotton swab, and the filters were fixed with 3% paraformaldehyde and stained with Crystal Violet. The extent of cell migration was analyzed using the Phase 3 image analysis software as described above.

Results and Discussion

CNTO 95 inhibits αvβ3- and αvβ5-mediated cell adhesion

Since CNTO 95 binds to αVβ3 and αVβ5 integrins, we determined whether our tumor cells (A375S.2 and HT29) and endothelial cells express these integrins. Flow cytometry indicated that A375S.2 and HUVEC cells express both αVβ3 and αVβ5 integrins, but HT29 cells express αVβ5, but not αVβ3 integrin (FIG. 12A–I).

HT29 cells (12A, B and C) express αvβ5, but not αvβ3 integrin on their surface. HUVEC (12D, E and F) and A375S.2 (12G, H and I) cells express αvβ5 and αvβ3 integrin on their surface. Tumor cells and endothelial cells were stained by immunofluorescence and analyzed by flow cytometry. The histogram on the left represents background fluorescence in the presence of isotype matched antibody. The histogram on the right indicates positive staining. A, D, G, LM609 (mAb directed to αvβ3, 10 μg/ml); B, E, H, PIF6 (mAb directed to αvβ5, 10 μg/ml); and C, F, I, GenO95 (10 μg/ml).

The effect of CNTO 95 on adhesion of HUVEC, A375S.2 and HT 29 cells to various matrix proteins was determined in detail. GenO95 completely inhibited adhesion of HUVEC and A375S.2 cells to vitronectin, and partially to fibrinogen, gelatin and fibrin coated plates, indicating that the antibody can block αVβ3 and αVβ5 (FIGS. 13 and 14, Table 1 and 2). GenO95 completely inhibited HT-29 cell adhesion to vitronectin coated plates, indicating that the antibody blocks αVβ5 (FIG. 15). GenO95 completely inhibited adhesion of HUVEC and A375S.2 cells to vitronectin coated plates, indicating that the antibody blocks αVβ3 and αVβ5 (FIGS. 13 and 14). Data were graphed as percent of maximal binding (no antibody) and non-linear regression performed using GraphPad Prism.

Adhesion of HUVECS to matrix protein-coated plates. Adhesion assay was performed as described in Methods. Plate was read on a fluorometer at 485–538 nm. Cell adhesion to BSA coated wells served as a negative control. In FIG. 13, the extent of cell adhesion in the presence of various concentrations of antibody was plotted as a percent of cell adhesion in the absence of antibody that was considered as 100%. Each data point is the mean of triplicate determinations (+/−SD).

Adhesion of human melanoma cells to matrix protein-coated plates. Adhesion assay was performed as described in Methods. Cell adhesion to BSA coated wells served as a negative control. In FIG. 14 the extent of cell adhesion in the presence of various concentrations of antibody was plotted as a percent of cell adhesion in the absence of antibody that was considered as 100%. Each data point is the mean of triplicate determinations (+/−SD).

Table 4 shows the extent of HUVECs adhesion to vitronectin, gelatin, fibrinogen, fibrin, fibronectin and type I collagen in the presence of various concentration of antibody was plotted as a percent of cell adhesion in the absence of antibody that was considered as 100%. Each data point is the mean of triplicate determinations (+/−SD). The concentration of antibodies used was 10 μg/ml.

TABLE 4

|  | Vitronectin | Gelatin | Fibrinogen | Fibrin | Fibronectin | Type I collagen |
|---|---|---|---|---|---|---|
| Human IgG | 96.3 ± 11.4 | 109.0 ± 8.8 | 108.0 ± 6.3 | 99.7 ± 4.5 | 96.8 ± 4.7 | 99.3 ± 4.1 |
| LM609 | 26.3 ± 3.7 | 36.5 ± 4.7 | 14.3 ± 2.5 | 48.1 ± 1.5 | 102.8 ± 7.2 | 108.8 ± 12.7 |
| PIF6 | 39.8 ± 5.9 | 94.4 ± 15.1 | 94.5 ± 4.2 | 96.7 ± 4.5 | 103.2 ± 3.8 | 115.7 ± 8.1 |
| LM609-PIF6 | 3.7 ± 0.4 | 32.2 ± 5.2 | 10.7 ± 1.1 | 30.7 ± 8.9 | 99.6 ± 4.7 | 116.2 ± 4.1 |
| CNTO 95 | 3.3 ± 0.6 | 54.8 ± 4.0 | 34.5 ± 1.7 | 45.1 ± 2.4 | 101.6 ± 6.1 | 97.7 ± 3.9 |
| ReoPro | 54.9 ± 0.9 | 2.5 ± 2.3 | 8.7 ± 2.9 | 35.8 ± 3.0 | 96.3 ± 2.8 | 99.6 ± 6.0 |

Table 5 shows the extent of A375S.2 cells adhesion to vitronectin, gelatin, fibrinogen, fibrin, fibronectin and type I collagen in the presence of various concentration of antibody. The data is expressed as a percent of cell adhesion in the absence of antibody that was considered as 100%. Each data point is the mean of triplicate determinations (+/−SD). The concentration of antibodies used is 10 μg/ml.

TABLE 5

|  | Vitronectin | Gelatin | Fibrinogen | Fibrin | Fibronectin | Type I collagen |
|---|---|---|---|---|---|---|
| Human IgG | 104.0 ± 5.3 | 94.6 ± 12.4 | 102.5 ± 5.9 | 99.5 ± 4.0 | 100.0 ± 5.5 | 99.1 ± 3.3 |
| LM609 | 42.1 ± 6.1 | 25.2 ± 7.1 | 14.0 ± 1.8 | 50.0 ± 1.9 | 104.0 ± 8.1 | 100.0 ± 1.5 |
| PIF6 | 28.5 ± 3.8 | 87.4 ± 7.8 | 99.4 ± 3.6 | 92.9 ± 4.7 | 101.0 ± 5.7 | 101.0 ± 7.3 |
| LM609-PIF6 | 0.9 ± 0.3 | 1.1 ± 1.5 | 10.3 ± 2.6 | 47.6 ± 3.2 | 109.0 ± 4.1 | 102.0 ± 4.6 |

TABLE 5-continued

|  | Vitronectin | Gelatin | Fibrinogen | Fibrin | Fibronectin | Type I collagen |
|---|---|---|---|---|---|---|
| CNTO 95 | 1.4 ± 0.4 | 23.2 ± 7.2 | 11.4 ± 2.8 | 43.3 ± 3.5 | 103.0 ± 4.5 | 104.0 ± 5.9 |
| ReoPro | 38.1 ± 0.7 | 6.0 ± 1.0 | 6.5 ± 2.1 | 12.9 ± 3.8 | 104.0 ± 5.6 | 93.1 ± 3.1 |

The adhesion human colon carcinoma HT29 cells to vitronectin in the presence of antibody was performed as described above. Cell adhesion to BSA coated wells served as a negative control. The data shown in FIG. 15 are plotted as percent of maximum binding (absence of antibody), and are the mean of triplicate determinations (+/−SD).

CNTO95 Blocks Human Melanoma and Endothelial Cell Migration

Integrins $\alpha V\beta 3$ and $\alpha V\beta 5$ participate in cell migration, therefore we determined whether CNTO 95 could block vitronectin-stimulated cell migration. Vitronectin-stimulated cell migration involves $\alpha V\beta 3$ and $\alpha V\beta 5$. CNTO 95 dose dependently inhibited endothelial cell migration when vitronectin was used as a chemoattractant (FIG. 17). Interestingly, CNTO 95 also inhibited migration of both HUVECS and A375S.2 cells to serum (FIGS. 18 and 19). These findings could be potentially important for angiogenic and tumor therapy because they suggest that the targets for CNTO 95, $\alpha V\beta 3$ and $\alpha V\beta 5$, are central receptors that are activated by a variety of migratory factors that are present in serum.

FIG. 16 shows the migration of HUVECS toward 2 μg/ml vitronectin. The assay was performed as described in Methods and cells were allowed to migrate for 6 h. Photomicrographs are representative fields (10× objective lens) of cell migration in FIGS. 16A, absence of antibody, (16B), CNTO 95 (5 μg/ml), (16C), CNTO 95 (40 μg/ml). FIG. 16D is graphical representation of cell migration in the presence of varying concentrations of GenO95. The data were normalized to percent of control (no antibody) which was considered as 100%, and each point is the mean of three transwell filters (+/−SD).

FIG. 17 shows the migration of HUVECS toward 2 μg/ml vitronectin in the presence of antibodies to $\alpha v\beta 3$ and $\alpha v\beta 5$. The migration assay was performed as described in Methods, and cells were allowed to migrate for 6 hours. LM609 and P1F6 are mAbs directed to $\alpha v\beta 3$ and $\alpha v\beta 5$, respectively. The data shown in FIG. 17 were normalized to percent of control (no antibody) which was considered as 100%, and each bar is the mean of three transwell filters (+/−SD). BSA, mouse IgG and human IgG served as negative controls. LM609-P1F6 represents combinations of both antibodies. The antibodies and BSA were used at a concentration of 10 μg/ml.

FIG. 18 shows the migration of HUVECS towards 2% FBS. Migration assay was allowed to proceed for 4 h and the data was captured as described in Methods. FIG. 18(A) is a graphical representation of cell migration in the presence of LM609, P1F6, combination of LM609+P1F6, isotype matched control antibodies (human and mouse). The antibodies and proteins were used at a concentration of 10 μg/ml. FIG. 18(B) is a graphical representation of cell migration in the presence of ReoPro and GenO95. Photomicrographs are representative fields (10× objective lens) of cell migration in FIG. 18(C), the absence of antibody, FIG. 18(D), GenO95 (5 μg/ml), and FIG. 18(E), GenO95 (20 μg/ml). The data were normalized to percent of control (no antibody) which was considered as 100%, and each point is the mean of three transwell filters (+/−SD).

FIG. 19 shows the migration of A375S.2 cells toward 10% FBS. Migration assay was allowed to proceed for 4 h and the data was captured as described in Methods. Antibodies were used at a concentration of 10 μg/ml. FIG. 19(A) is a graphical representation of cell migration in the presence of varying concentrations of GenO95. FIG. 19(B) is a graphical representation of cell migration in the presence of LM609, P1F6, combination of LM609+P1F6, isotype matched control antibodies (human and mouse). The data were normalized to percent of control, which was considered as 100%, and each point is the mean of three transwell filters (+/−SD). Photomicro-graphs are representative fields (10× objective lens) of cell migration in FIG. 19(C), absence of antibody, FIG. 19(D), GenO95 (5 μg/ml), and FIG. 19(E), GenO95 (20 μg/ml).

Results described above indicate that CNTO 95 blocks tumor and endothelial migration to vitronectin and serum. Next, we determined whether this antibody could inhibit bFGF-stimulated cell migration. As shown in FIG. 20, bFGF stimulated HUVEC cell migration towards vitronectin, and CNTO 95 significantly blocked this stimulated cell migration.

FIG. 20 shows the migration of HUVECS towards vitronectin in the presence of bFGF. The undersides of migration chamber filters were coated with 2 μg/ml vitronectin, and the assay was performed as described in Methods. Cells were allowed to migrate for 6 h. In FIG. 20A–E, each data point is the mean of 3 transwell filters (+/−SD). FIG. 20(A), bFGF; FIG. 20(B), CNTO 95 (5 μg/ml); FIG. 20(C), CNTO 95 (40 μg/ml); FIG. 20(D), no-bFGF. FIG. 20(E), Inhibition of cell migration in the presence of various antibodies is shown graphically.

GenO95 Blocks Human Melanoma Cell Invasion

Results described above indicate that CNTO 95 can inhibit cell adhesion and migration. Therefore, we questioned whether this antibody could block tumor cell invasion, a multistep process that involves cell adhesion, degradation of the matrix, and migration of cells through the degraded matrix. We chose fibrin as a matrix for tumor cells because CNTO 95 was able to block tumor cell adhesion to fibrin (FIG. 3). As shown in FIG. 10, invasion of A375S.2 cells could be inhibited by LM609, suggesting the involvement of at least $\alpha v\beta 3$ in this process. CNTO 95 dose dependently inhibited tumor cell invasion through fibrin. Irrelevant IgG and a mAb directed to platelet GPIIb/IIIa (10E5) served as negative controls. Collectively, these data suggest that CNTO 95 can effectively block invasion of human melanoma cells.

Invasion of A375S.2 cells through a fibrin gel (5 mg/ml). Invasion assay was allowed to proceed for 24 h and data was captured as decribed in Methods. Photomicrographs are representative fields (4× objective lens) of cell invasion in FIG. 21(A) the absence of antibodies, FIG. 21(B) CNTO 95 (10 μg/ml), FIGS. 21(C) and (D) are graphical representation of cell invasion in presence of CNTO 95, 10E5 F(ab')$_2$, LM609, P1F6, LM-PIF6 (LM609+P1F6), human and mouse IgGs (H-IgG and M-IgG). Graph FIG. 21(D): The concentration of all antibodies and proteins is 10 μg/ml. The data were normalized to percent of control (no antibody) which was considered as 100%, and each point is the mean of three transwell filters (+/−SD).

Conclusion

Cell adhesion, migration and invasion requires integrins such as αvβ3 and αvβ5. CNTO 95 is able to functionally block αvβ3 and αvβ5 integrins that are expressed by endothelial and tumor cells. CNTO 95 was able to block migration and invasion of cells that were stimulated by bFGF or serum. These results suggest that the CNTO 95 is a potent inhibitor of tumor and endothelial cell expressed αvβ3 and αvβ5 integrins.

REFERENCES

1. Taylor, L. D., C. E. Carmack, D. Huszar, K. M. Higgins, R. Mashayekh, G. Sequar, S. R. Schramm, C-C. Kuo, S. L. O'Donnell, R. M. Kay, C. S. Woodhouse, and N. Lonberg. 1993. Human immunoglobulin transgenes undergo rearrangement, somatic mutation and class switching in mice that lack endogenous IgM. International Immnunology 6:579–591.
2. Lonberg, N., L. D. Taylor, F. A. Harding, M. Trounstine, K. M. Higgins, S. R. Schramm, C-C. Kuo. R. Mashayekh, K. Wymore, J. G. McCabe, D. Munoz-O'Regan, S. L. O'Donnell, E. S. G. Lapachet, T. Bengoechea, D. M. Fishwild, C. E. Carmack, R. M. Kay, and D. Huszar. 1994. Antigen-specific human antibodies from mice comprising four distinct genetic modifications. Nature 368:856–859.
3. Neuberger, M. 1996. Generating high-avidity human Mabs in mice. Nature Biotechnology 14:826.
4. Fishwild, D. M., S. L. O'Donnell, T. Bengoechea, D. V. Hudson, F. Harding, S. L. Bernhard, D. Jones, R. M. Kay, K. M. Higgins, S. R. Schramm, and N. Lonberg. 1996. High-avidity human IgG monoclonal antibodies from a novel strain of minilocus transgenic mice. Nature Biotechnology 14:845–851.
5. Gastl, G., T. Hermann, M. Steurer, J. Zmija, E. Gunsilius, C. Unger, and A. Kraft. 1997. Angiogenesis as a Target for Tumor Treatment. Oncology 54: 177–184.
6. Eliceiri, B. P., and D. A. Cheresh. 1999. The role of αV integrins during angiogenesis: insights into potential mechanisms of action and clinical development. The Journal of Clinical Investigation 103: 1227–1230.
7. Friedlander M., P. C. Brooks, R. W. Shaffer, C. M. Kincaid, J. A. Varner, and D. A. Cheresh. 1995. Definition of two angiogenic pathways by distinct αV integrins. Science 270: 1500–1502.

EXAMPLE 6

Production and Characterization of Antibodies to the Variable Region of CNTO 95

Anti-anti-bodies were prepared by immunization of Balb/c mice with CNTO 95. Initial titers from mice immunized with CNTO 95 ranged from a high of >1:40,000, to a low of 1:20,000.

For fusions C371idD, C371idH, C371idI and C371idJ, mice #2, 11, 12 and 14 respectively, were IV boosted with 50 mg of CNTO 95 diluted to 100 mL in phosphate buffered saline (PBS). For fusions C371idK and C371idL, mice #16 and 17 respectively, were boosted using 50 mg CNTO 95-mouse albumin conjugate as above. Three days after the IV injection, the mice were sacrificed by cervical dislocation and the spleen was removed aseptically, spleenocytes were isolated, and fused to the non-secreting mouse myeloma fusion partner, P3×63 Ag 8.653.

From six fusions utilizing CNTO 95 immunized Balb/c mice, seventeen anti-variable region antibody-producing hybridomas were identified based on their specific reactivity with the variable region of the human aVb3 and aVb5 antibody, CNTO 95 (IgG1k), and for their nonrecognition of isotypic antigenic determinants.

TABLE 2

Characterization of CNTO 95 Anti-variable region Mabs

| | Murine Isotype | Anti-ID Mab binding to CNTO 95 Prebound to αVβ3 | Anti-ID Mab inhibition of CNTO 95 binding to αVβ3 | Inhibition of ID binding in the presence of 0.5% NHS | Inhibition of ID binding in the presence of 5% NHS | Inhibition of ID binding in the presence of 50% NHS |
|---|---|---|---|---|---|---|
| C508 | IgG2b κ | − | + | − | − | − |
| C577 | IgG1 κ | − | + | − | − | inhibition |
| C580 | IgG1 κ | − | − | − | − | − |
| C581 | IgG1 κ | − | + | − | − | − |
| C582 | IgG1 κ | − | + | − | − | − |
| C583 | IgG1 κ | − | + | − | − | − |
| C571 | IgG1 κ | − | − | − | − | − |
| C578 | IgG2b κ | + | − | − | − | − |
| C585 | IgG2b κ | − | + | − | − | − |
| C572 | IgG1 κ | − | − | − | − | − |
| C573 | IgG1 κ | − | − | − | − | − |
| C574 | IgG1 κ | − | + | − | − | − |
| C575 | IgG1 κ | − | − | − | − | − |
| C576 | IgG1 κ | − | + | − | − | − |
| C579 | IgG1 κ | − | + | − | − | − |
| C584 | IgG1 κ | − | + | − | − | − |
| C586 | IgG1 κ | − | + | − | − | − |

(NHS = Normal Human Serum)

Seventeen monoclonal antibodies were made to the variable region of CNTO 95. Six of them (C571–3, C575, C578 and C580) were demonstrated not to block binding of the antibody to alpha-V-beta3. The remaining eleven (C508, C576–7, C581–6,C574 and C579) appear to block the active site of CNTO 95 and inhibit the binding of CNTO 95 to human integrin aVb3 and do not bind to CNTO 95 prebound to its receptor. The non-blocking Mab, C578, can detect CNTO 95 pre-bound to aVβ3. Pooled human serum does not interfere with the binding of 16 of 17 CNTO 95 anti-variable region Mabs.

These seventeen Mabs could prove useful in pharmacokinetic or immunohistochemical detection of CNTO 95 in patient and animal tissue or sera samples.

EXAMPLE 7

Demonstration of Anti-Alpha-V Subunit Antibody Binding to Alpha-V Beta-6 on the Surfaces of Cells CNTO 95 is capable of recognizing the alpha-V (or alpha5) subunit as it is presented on cell surfaces when complexed with the beta subunits designated beta-III (beta-3) and beta-5. It is important to ascertain that the epitope for binding the alpha-V subunit is still available when alpha-V is present in other heterodimeric forms of integrins such as alpha-V, beta-1 or alpha-V, beta-6.

The following study confirms that CNTO 95 has the capability to bind the heterodimeric receptor alpha-5,beta-6 as it occurs on the surface of a cell.

Materials and Methods

CNTO 95 antibody was from Centocor (Malvern, Pa. 19355). All other antibody reagents listed below were purchased from Chemicon, International, Inc. (Temecula Calif.). The control and comparator antibodies included: H IgG 557276, MAB 1959 to beta1, MAB 2076Z to beta6, MAB 1953Z to alpha-V, MAB 1976Z to alpha-V-beta-3, MAB 1961Z to alpha-V-beta-5, MAB 2077Z to alpha-V-beta6, MAB 2075Z to beta6, and MAB 2074Z to alpha-V-beta6.

HEK-293 cells (Human embryonal kidney cells, ATCC CRC-1573) were transfected with cDNA constructs to over-express either human av, b6, or avb6 integrins.

Cell Staining and Flow Cytometric Analysis:

Cell suspensions were prepared by trypsinizing adherent cell cultures, washing and resuspending the cells in serum free media (SFM). Thereafter, the cells were reacted with primary antibody, washed and reacted with a second antibody carrying a fluorescent marker.

Primary antibody reaction: cells ($1 \times 10^6$ cells/ml) were resuspended in 200 microL SFM, and 2 µL of antibody was added to give a final antibody concentration 10 mcirogm/ml in each tube. Cells were incubated from 45 minutes to 1 hour on ice, keeping tubes in the dark. To wash away extra antibody, 3 ml of DPBS was added, and tubes were centrifuged at 1300 RPM for 3 minutes at 4° C.

Secondary antibody: Phycoerythrin-conjugated secondary antibodies were added as described above. After 1 hour, tubes were centrifuged at 1300 RPM for 3 minutes at 4° C., and cells were resuspended in 0.5 ml of FACS buffer.

Flow cytometry: Samples were mixed thoroughly before analysis. Flow cytometric analysis was performed on a Becton-Dickinson FACSCalibur, using both green (FITC) and red (phycoerythrin) channels.

Results

As seen in the upper row of FIG. 22A, mock transfected HEK 293 cells demonstrated immunoreactivity for integrin alpha-V, and some immunoreactivity for beta-6 and avb6 (weak), as shown by comparing the position of the open curve (control stain) against the shaded curve (test antibody). Transfection of HEK 293 cells with either b6 or avb6 cDNA caused a high level of immunoreactivity for avb6 integrin as demonstrated by comparing the shaded curves in the third panels of rows 3 and 4 against the shaded curve in the third panel of row 1. A stronger shift toward the right indicates stronger immunoreactivity and higher protein expression.

Transfection with avb6 did not cause a change in expression of avb3 (column 1), avb5 (column 2), or b1 (column 3) integrins compared to mock transfected cells (FIG. 22B). The positions of the shaded curves in each of the panels in the lower row (avb6 transfected) are nearly identical to the positions of the corresponding shaded curves in the upper row (mock transfected). Therefore, any change seen in CNTO 95 binding would not be due to changes in avb3 or avb5 expression.

As shown in FIG. 22C, overexpression of human integrin subunits aV (panel 2) or b6 (panel 3) alone caused a small increase in CNTO 95 immunoreactivity, which is indicated by a shift toward the right of the shaded curves compared to panel 1. Transfection with the heterodimeric human avb6 integrin (panel 4) caused a dramatic increase in CNTO 95 staining as demonstrated by a large proportion of the shaded curve to the right of the vertical line. As a further confirmation, cells were double-stained for both avb6 and CNTO 95 (FIG. 22D). As seen previously, mock transfected cells showed a small amount of immunoreactivity for avb6 (panel A) and substantial immunoreactivity for CNTO 95 (FIG. 22D panel B). Plotting immunoreactivity of avb6 (vertical axis) against CNTO 95 (horizontal axis), a large proportion of mock transfected cells fell into the lower-right quadrant (FIG. 22D, panel C), indicating immunoreactivity to CNTO 95 alone. Analysis of avb6 transfected cells showed a large increase in immunoreactivity for avb6 (FIG. 22D panel D), as well as for CNTO 95 (FIG. 22D panel E). Plotting immunoreactivity of avb6 (vertical axis) against CNTO 95 (horizontal axis) revealed a strong shift in the population of cells toward the upper-right quadrant (FIG. 22D panel F), indicating that cells which stained intensely for avb6 also stained intensely for CNTO 95. Taken together, the results indicate that CNTO 95 binds to alphavbeta6 integrin.

EXAMPLE 8

Characterization of CNTO 95 Ligands in Human Placental Tissue

Human placenta is a source of a spectrum of adhesion molecules including known integrins. Ligands binding CNTO 95 from a human placental extract were identified using commercially available Mabs with known specificity.

Human placenta was donated with consent. Approximately 300 g tissue was washed with ice cold buffered saline followed by addition of 600 ml of extraction buffer (TBS, pH7.5, 1 mM $CaCl_2$, 1 mM $MnCl_2$, 100 mM Octylglucoside (OTG), and EDTA-free protease inhibitor tablets from Roche Applied Sciences). The tissue was minced with scissors and then homogenized using a blender. After homogenation, 17.52 g OTG was added to the homogenate and the mixture was rotated at 4° C. overnight. The extract was the supernatant taken after centrifugation in a SORVALL RC5CPLUS centrifuge in a SLA 3000 rotor at 10,000 rpm for 1 hour at 4° C. Extracts were stored at 4° C.

CNTO 95 (Centocor, Malvern, Pa.) and MAB1978 (anti-integrin alphaV purchased from Chemicon, Temecula, Calif. as ascites fluid and purified using an immobilized protein A (Pierce Chemicals) were coupled to CNBr-activated sepharose 4 Fast Flow (Amersham) according to standard procedures.

Placenta extracts were incubated with CNTO 95- or MAB1978-conjugated resin overnight at 4° C. Resins were then loaded to empty columns. Columns were washed with 10 ml of column wash buffer I followed by 10 ml of column wash buffer H. Integrin fractions were eluted with 10 ml of elution buffer from the columns. The eluted materials were concentrated and stored at 4° C. for further analysis.

Western blot. The integrin fraction were separated by electrophoresis on 4–12% SDS polyacrylamide gels and then transferred to nitrocellulose filters. The filters were blocked with 5% nonfat dry milk in TBS containing 0.05% Tween 20 (wash buffer) at room temperature for 1 hour and then incubated with anti-integrin antibodies (anti-a5 (P-19) Santa Cruz, goat polyclonal IgG 1:500 dilution; anti-aIIb, Chemicon, mouse monoclonal IgG1, 1:1000 dilution; anti-aV (Q-20), Santa Cruz, goat polyclonal IgG, 1:500 dilution; anti-b1 (4B7R), Santa Cruz, mouse monoclonal IgG1, 1:500 dilution; anti-b1 (N-20), Santa Cruz, goat polyclonal IgG, 1:500 dilution; anti-β3 (H-96), Santa Cruz, rabbit polyclonal IgG, 1:500 dilution; anti-β5 (H-96), Santa Cruz, rabbit polyclonal IgG, 1:500 dilution; anti-β6 (H-110), Santa Cruz, rabbit polyclonal IgG, 1:250 dilution). After thorough washing, filters were incubated with appropriate peroxidase-conjugated secondary antibodies (1:20000 dilution). The antigen-antibody complexes were visualized using Super-Signal West Pico Chemiluminescent Substrate kit (Pierce).

To identify which integrins eluted fraction from CNTO 95 affinity column Western blot analysis was performed on strips of the blot incubated with individual antibody preparations. The strips labeled positively with anti-integrin-aV, -b1, -b3, -b5; and -b6, demonstrating that the above integrin subunits are components of integrin complexes bound by CNTO 95. Since integrins are subunits of alpha subunits and beta subunits, the results indicate that CNTO 95 binds aVb1, aVb3, aVb5, and aVb6 subunit integrins.

To further define the integrin specificity of CNTO 95, integrin fractions purified from CNTO 95 affinity column were examined by Western blots with antibodies against integrin a5 and integrin aIIb, it should be noted that placenta contains abundant integrin a5b1 and integrin aIIbb3. Purified integrin aSbl and crude placenta extract, were stained by anti-integrin a5 or anti-aIIb antibody. However, there were no detectable signals for a5 and aIIb in lanes loaded with proteins purified by CNTO 95 affinity chromatography.

Therefore, CNTO 95 binds all subunit of the integrins containing alphaV tested and not a5 or aIIb containing heterodimers.

EXAMPLE 9

In Vitro Angiogenesis: Microvessel Sprouting

Rat aortic ring assay. An early event during tumor-induced angiogenesis is the formation of microvessel sprouts from established blood vessels that migrate towards the tumor. A microvessel sprouting assay was used to test the in vitro anti-angiogenic activity of CNTO 95. In this assay, freshly excised rat aortas were cultured in 3-dimensional fibrin or collagen gels. In the presence of various angiogenic factors such as bFGF, the aorta sprouts microcapillaries after a few days. This process is a representation of angiogenesis, as it involves endothelial cell adhesion, migration, invasion, and proliferation.

The rat aortic ring assay was performed as described by Nicosia et al. (Lab Invest. 63: 115–122, 1990) with slight modifications (Sassoli, et al. Thromb Haemost, 85: 896–902, 2001). 10 mm diameter agarose wells (1.5%) prepared in 100×15 mm tissue culture dishes were filled with M199 media containing rat tail type 1 collagen (2.8 mg/ml, Becton Dickinson), NaHCO3 (28 mM) and either CNTO 95 (10 ug/ml), nonspecific control murine IgG (20 mg/ml) or BSA (20 mg/ml). Rat aortic ring sections (1 mm) were placed on top of collagen gels within the agarose rings; wells were filled with collagen solution and incubated at 37° C. After the collagen had gelled, the collagen-aortic ring sandwiches were transferred to 12 well plates containing 1 ml EBM-2 medium, BSA (0.1%), bFGF (10 ng/ml), penicillin (100 U/ml), streptomycin (100 mg/ml), amphotericin B (0.25 mg/ml) (all from Clonetics), and either CNTO 95 (increasing concentrations), non-specific control mIgG (20 ug/ml), or BSA (20 mg/ml). Plates were maintained in a 37° C. tissue culture incubator with media changes every other day. After 10 days, the number and length of microvessel sprouts originating from each aortic ring was quantified microscopically using the Phase 3 Image Analysis System.

As shown in FIG. 23, CNTO 95 inhibited sprouting of microvessels from aortas excised from rats in a dose-dependent manner These results demonstrate that CNTO 95 is an inhibitor of angiogenesis in vitro.

EXAMPLE 10

Anti-Alpha V Antibody Blocks Angiogenesis in Vivo

Rat and Monkey Matrigel Assays

In order to determine whether CNTO 95 could functionally block aVb3 and aVb5 integrins, a non-human primate model and a nude rat model of growth factor-induced angiogenesis and in a nude rat model of tumor cell-induced angiogenesis were used. The monkey study was performed at Charles River Laboratories (Worcester, Mass.) on young adult female Cynomolgus monkeys (species macaca fascicularis). Nude female rats (5–7 weeks old) were obtained from Harlan (Indianapolis, Ind.). Recombinant human bFGF was obtained from R&D Systems. Matrigel, prepared from the Engelbreth-Holm-Swarm tumor, was obtained from Becton Dickinson.

Liquid Matrigel was maintained at 4° C. The angiogenesis assays were performed as described (Trikha, et al. Cancer Res., 62: 2824–2833, 2002). For growth factor induced angiogenesis, human bFGF (5 mg/ml) was added to the Matrigel solution and allowed to mix thoroughly overnight. The Matrigel was then mixed with antibodies or control solutions and kept on ice. For tumor-cell induced angiogenesis, human melanoma M21 cells were harvested with trypsin-EDTA, centrifuged, washed twice with DMEM, and resuspended in ice-cold DMEM. M21 cells were gently added to the Matrigel solution at a final concentration of $0.5 \times 10^6$/ml. The tumor cell-Matrigel solution was gently mixed and stored on ice until it was injected into nude rats.

Monkeys were injected at each site subcutaneously with 2 ml of Matrigel solution, while rats were injected with 1 ml of Matrigel each. In the tumor cell-induced study, rats were injected at two sites with 1 ml of the ice-cold tumor cell-Matrigel solution. Gel formation was confirmed after injection. Animals received test article via intravenous or intraperitoneal bolus injection. At the end of each study, animals were euthanized and Matrigel harvested from the injection sites. Matrigel implants were weighed, photographed and graded for angiogenesis using the Phase 3 Image Analysis System. To measure the total area of neovessels, photomicrographs were taken from both the top surface and the bottom surface of each Matrigel plug at 2× magnification on the inverted phase contrast microscope. The vessel length and number of vessels per field were calculated using the tracing function within the Phase 3 Image System. The mean value from all 2× fields was calculated for each Matrigel plug, and the mean vessel number and vessel length for each test group was calculated.

As a third method to measure angiogenesis, immunohistochemistry was performed on 10 mm serial cryostat sections cut from frozen Matrigel plugs. Sections were immediately fixed in cold acetone (5 min) and air-dried. The sections were washed 3 times in PBS to remove frozen mounting media, blocked for 1 hour with 5% mouse serum and 5% goat serum in PBS and rinsed in PBS. The sections were then blocked with Avidin-Biotin solution (X0590, DAKO Corporation, Carpinteria, Calif.) for 10 min. After washing, endogenous peroxidase was quenched by incubation in 3% hydrogen peroxide for 10 min. Then, the sections were incubated for 60 min with primary antibody (mouse anti-human PECAM, BD PharMingen, Bedford, Mass.; 10 mg/ml) diluted with DAKO antibody diluent solution (S3022, DAKO). Immunoreactive sites were detected using a DAKO Kit, and sections were counterstained with hematoxylin. An irrelevant mouse IgG1 was used as a negative control in all cases. Photomicrographs were taken from all slides at 20× magnification; each entire section was photographed. The vessel density per field was calculated using the Phase 3 Image System software. Vessel density was quantitated by measuring the percentage of cross-sectional area of each Matrigel section occupied by stained microvessels. The mean value for each slide was calculated, and the mean vessel density for each group was determined.

Results

Inclusion of human bFGF in Matrigel implants in monkeys and rats resulted in increased angiogenesis as measured by vessel length, number, and vessel density (FIG. 24–26). Systemic treatment of rats with CNTO 95 significantly inhibited bFGF-stimulated increases in vessel length and total vessel number within Matrigel implants as measured by visual inspection. Inhibition of angiogenesis by CNTO 95 was dose-dependent, with a dose of 1 mg/kg being active in this model (FIG. 24). Results of the immunostaining of vessels with anti-CD31 were consistent with those obtained by direct visual counting of microvessels.

Subcutaneous injection of Matrigel containing human bFGF in cynomolgus monkeys resulted in increased angiogenesis as measured by vessel length, number, and vessel density (FIG. 25A–C). Systemic treatment of monkeys with CNTO 95 significantly inhibited bFGF-stimulated increases in vessel length (FIG. 25A) and total vessel number (FIG. 25B) within Matrigel implants as measured by image analysis quantification. Systemic treatment of monkeys with CNTO 95 also reduced the bFGF-stimulated increase in microvessel density within Matrigel implants as measured by immunostaining for CD31 expression and image analysis (FIG. 25C).

In the tumor cell-induced angiogenesis model, a single dose of 10 mg/kg of CNTO 95 inhibited tumor cell-induced angiogenesis. No difference in inhibitory activity was observed when CNTO 95 was administered as a single intravenous dose or when it was mixed with the Matrigel-tumor cell suspension prior to injection into the rats. Inhibition of angiogenesis by CNTO 95 was demonstrated by decrease in the length and number of microvessels (FIG. 26) and decrease in hemoglobin content in the Matrigel plugs (data not shown).

Collectively, these results indicated that CNTO 95 inhibited angiogenesis stimulated by either bFGF in both nude rats and non-human primates. CNTO 95 also prevents human tumor cell induced angiongenesis in an immunosuppressed animal.

EXAMPLE 11

Anti-Tumor Effect of Anti-Alpha V Antibody in Nude Mice and Rats

For studies performed in nude mice, female nude mice, aged 4–5 weeks, were purchased from Charles River Laboratories (Wilmington, Mass.), and were maintained according to the NIH standards established in the 'Guidelines for the Care and Use of Experimental Animals'. Twenty mice were inoculated subcutaneously with A375.S2 cells (3×106) in the flank region (day 0). On day 3, the mice were randomly divided into two groups. One group was injected i.p. with CNTO 95 (10 mg/kg in PBS), while the other group received vehicle. Dosing was continued three times a week thereafter until day 26. Tumors were measured by calipers twice a week, and tumor volumes were calculated by the formula (length×width2/2). Body weights were also recorded weekly.

For studies performed in nude rats, female nude rats, aged 6–7 weeks, were purchased from Harlan (Indianapolis, Ind.), and were maintained according to the NIH standards established in the 'Guidelines for the Care and Use of Experimental Animals'. Twenty rats were inoculated subcutaneously with A375.S2 cells (3×106) in the flank region (day 1). On day 4, the rats were randomly assigned to two groups. One group was injected i.v. with CNTO 95 (10 mg/kg in PBS), while the other group received an isotype-matched control IgG (10 mg/kg). Dosing was continued weekly thereafter until day 46 (total of 6 doses). Tumors were measured by calipers twice a week, and tumor volumes were calculated by the formula (length×width2/2). Body weights were also recorded weekly. Statistical comparison of group mean tumor volumes was performed using Student's t-test, 2-tailed analysis.

Results

To determine the anti-tumor efficacy of CNTO 95 in vivo, a human A375.S2 melanoma xenograft tumor model was established in nude mice. Mice were treated with CNTO 95 (10 mg/kg) 3 times per week by i.p. injection, starting 3 days after tumor inoculation. As shown in FIG. 27, dosing with CNTO 95 inhibited growth of human melanoma tumors in nude mice. At day 26 CNTO 95 inhibited tumor growth by ~80% compared to tumors from control-treated animals. In this model CNTO 95 does not interact with host angiogenic vessels, since CNTO 95 does not bind mouse integrins, suggesting that blockade of human tumor-expressed integrins alone can inhibit tumor growth in mice independent of anti-angiogenic effects.

To determine the anti-tumor efficacy of CNTO 95 in another xenograft animal model, an A375.S2 human melanoma model was developed in female nude rats. In this model CNTO 95 is capable of blocking both rat angiogenic integrins and human tumor cell expressed integrins. Weekly treatment of tumor-bearing nude rats with CNTO 95 at 10 mg/kg reduced tumor growth compared to the isotype-matched human IgG control mAb (FIG. 28). By day 46, treatment with CNTO 95 resulted in a significant reduction in final tumor size compared to control-treated nude rats (P=0.0007).

In addition to blocking integrins on angiogenic endothelium, CNTO 95 has the ability to inhibit integrin function on tumor cells themselves. AlphaV integrins have been suggested to play critical roles in tumor cell biology. Therefore, the use of CNTO 95 has applicability to multiple tumor types with different integrin expression patterns.

In the nude mouse xenograft model, CNTO 95 does not cross-react with host integrins, however, treatment with CNTO 95 significantly inhibited the growth of the $\alpha v\beta 3$/$\beta 5$ positive melanoma tumors. In a previous report (Trikha et al. supra), it was demonstrated that antibody against $\alpha v\beta 3$ on the surface of human melanoma cells partially inhibited tumor growth in nude mice. In that study, m7E3 F(ab')2, a murine antibody which binds and blocks human $\alpha v\beta 3$ and $\alpha IIb\beta 3$, directly reduced growth of a human melanoma xenograft without blocking host cell integrins. CNTO 95 differs from m7E3 F(ab')2 in that it is a full-length human IgG that recognizes αvβ3 and αvβ5, but not the αIIbβ3 that is predominantly expressed on platelets.

Together these data suggest that through combined blockade of αvβ3 and αvβ5 integrins on tumor and endothelial cells, CNTO 95 may have multiple mechanisms of action that contribute to its observed antitumor efficacy in animal models.

It is becoming increasingly clear that although targeted therapy holds great promise, combination drug regimens will likely be necessary for optimal efficacy. CNTO 95 by itself targets multiple crucial receptors involved in tumor growth, angiogenesis and metastasis. An additional advantage of CNTO 95 is its fully-human nature, which will allow long-term and repeated use with anticipated safety due to lack of the HAMA reactions seen with murine antibodies.

It will be clear that the invention can be practiced otherwise than as particularly described in the foregoing description and examples.

Numerous modifications and variations of the present invention are possible in light of the above teachings and, therefore, are within the scope of the appended claims.

What is claimed is:

1. An isolated human monoclonal antibody comprising human heavy chain and human light chain variable regions comprising the amino acid sequences shown in SEQ ID NO: 7 and SEQ ID NO: 8, respectively.

2. The antibody of claim 1 which completely inhibits M21 cell adhesion to vitronectin.

3. The antibody of claim 1, comprising a human IgG heavy chain and a human kappa light chain.

4. The antibody of claim 1, comprising an IgG1 or IgG3 heavy chain.

5. A pharmaceutical composition comprising the antibody of claim 1 and a pharmaceutically acceptable carrier.

6. A composition according to claim 5 wherein the antibody is combined with an anti-neoplastic agent selected from the group consisting of a radiopharmaceutical, an estrogen receptor modulator, a retinoid, a topoisomererase inhibitor, a cytotoxin, an alkylating agent, a nitrogen mustard, a nitrosourea , an antimetabolite, a mitotic inhibitor, and a radiosensitizer.

7. A composition according to claim 6 wherein the alkylating agent is dacarbazine.

8. An immunoconjugate comprising the antibody according to claim 1 linked to a therapeutic agent.

9. The immunoconjugate of claim 8 wherein the therapeutic agent is a cytotoxin.

10. The immunoconjugate of claim 9 wherein the therapeutic agent is a radioisotope.

11. A pharmaceutical composition comprising the immunoconjugate of claim 8 and a pharmaceutically acceptable carrier.

12. An article of manufacture for human pharmaceutical or diagnostic use, comprising packaging material and a container comprising a solution or a lyophilized form of isolated human anti-alpha-V subunit antibody according to claim 1.

13. The article of manufacture of claim 12, wherein said container is a component of a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

14. An isolated human monoclonal antibody according to claim 1 produced by a method comprising transfecting a host cell or transgenic animal or transgenic plant or plant cell capable of expressing in recoverable amounts said antibody with a nucleic acid molecule encoding said antibody and recovering the antibody from cell, animal or plant.

15. An isolated human monoclonal antibody according to claim 1, wherein said antibody binds purified human $\alpha_v\beta_3$ and $\alpha_v\beta_5$ integrins with an affinity of at least one selected from at least $10^{-9}$ M, at least $10^{-10}$ M, at least $10^{-11}$ M, or at least $10^{-12}$ M.

16. An isolated human monoclonal antibody according to claim 15, wherein said antibody binds purified human $\alpha_v\beta_3$ and $\alpha_v\beta_5$ integrins with an affinity of at least $10^{-9}$ M.

17. An isolated human monoclonal antibody according to claim 15, wherein said antibody binds purified human $\alpha_v\beta_3$ and $\alpha_v\beta_5$ integrins with an affinity of at least $10^{-10}$ M.

18. An isolated human monoclonal antibody according to claim 15, wherein said antibody binds purified human $\alpha_v\beta_3$ or $\alpha_v\beta_5$ integrins with an affinity of at least $10^{-11}$ M.

19. An isolated human monoclonal antibody according to claim 15, wherein said antibody binds human $\alpha_v\beta_6$ integrin in HEK-293 cells transfected with a cDNA construct to overexpress $\alpha_v\beta_6$ integrin.

20. The human monoclonal antibody of claim 1 which is an IgG1kappa antibody.

* * * * *

SEQUENCE LISTING

```
<160> NUMBER OF SEQ ID NOS: 17

<210> SEQ ID NO 1
<211> LENGTH: 5
<212> TYPE: PRT
<213> ORGANISM: Homo sapiens

<400> SEQUENCE: 1

Arg Tyr Thr Met His
1               5

<210> SEQ ID NO 2
<211> LENGTH: 17
<212> TYPE: PRT
<213> ORGANISM: Homo sapiens

<400> SEQUENCE: 2

Val Ile Ser Phe Asp Gly Ser Asn Lys Tyr Tyr Val Asp Ser Val Lys
1               5                   10                  15

Gly

<210> SEQ ID NO 3
<211> LENGTH: 10
<212> TYPE: PRT
<213> ORGANISM: Homo sapiens

<400> SEQUENCE: 3

Glu Ala Arg Gly Ser Tyr Ala Phe Asp Ile
1               5                   10

<210> SEQ ID NO 4
<211> LENGTH: 11
<212> TYPE: PRT
<213> ORGANISM: Homo sapiens

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: Homo sapiens

<400> SEQUENCE: 5

Asp Ala Ser Asn Arg Ala Thr
1               5

<210> SEQ ID NO 6
<211> LENGTH: 8
<212> TYPE: PRT
```

```
<213> ORGANISM: Homo sapiens

<400> SEQUENCE: 6

Gln Gln Arg Ser Asn Trp Pro Pro
1               5

<210> SEQ ID NO 7
<211> LENGTH: 119
<212> TYPE: PRT
<213> ORGANISM: Homo sapiens

<400> SEQUENCE: 7

Gln Val Gln Leu Val Glu Ser Gly Gly Val Val Gln Pro Gly Arg
1               5                   10                  15

Ser Arg Arg Leu Ser Cys Ala Ala Ser Gly Phe Thr Phe Ser Arg Tyr
                20                  25                  30

Thr Met His Trp Val Arg Gln Ala Pro Gly Lys Gly Leu Glu Trp Val
            35                  40                  45

Ala Val Ile Ser Phe Asp Gly Ser Asn Lys Tyr Tyr Val Asp Ser Val
        50                  55                  60

Lys Gly Arg Phe Thr Ile Ser Arg Asp Asn Ser Glu Asn Thr Leu Tyr
65                  70                  75                  80

Leu Gln Val Asn Ile Leu Arg Ala Glu Asp Thr Ala Val Tyr Tyr Cys
                85                  90                  95

Ala Arg Glu Ala Arg Gly Ser Tyr Ala Phe Asp Ile Trp Gly Gln Gly
                100                 105                 110

Thr Met Val Thr Val Ser Ser
            115

<210> SEQ ID NO 8
<211> LENGTH: 108
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
                100                 105

<210> SEQ ID NO 9
<211> LENGTH: 1048
<212> TYPE: PRT
<213> ORGANISM: Homo sapiens

<400> SEQUENCE: 9

Met Ala Phe Pro Pro Arg Arg Arg Leu Arg Leu Gly Pro Arg Gly Leu
1               5                   10                  15
```

-continued

```
Pro Leu Leu Leu Ser Gly Leu Leu Pro Leu Cys Arg Ala Phe Asn
         20                  25                  30

Leu Asp Val Asp Ser Pro Ala Glu Tyr Ser Gly Pro Glu Gly Ser Tyr
             35                  40                  45

Phe Gly Phe Ala Val Asp Phe Val Pro Ser Ala Ser Ser Arg Met
 50                  55                  60

Phe Leu Leu Val Gly Ala Pro Lys Ala Asn Thr Thr Gln Pro Gly Ile
 65                  70                  75                  80

Val Glu Gly Gly Gln Val Leu Lys Cys Asp Trp Ser Thr Arg Arg
                 85                  90                  95

Cys Gln Pro Ile Glu Phe Asp Ala Thr Gly Asn Arg Asp Tyr Ala Lys
             100                 105                 110

Asp Asp Pro Leu Glu Phe Lys Ser His Gln Trp Phe Gly Ala Ser Val
         115                 120                 125

Arg Ser Lys Gln Asp Lys Ile Leu Ala Cys Ala Pro Leu Tyr His Trp
 130                 135                 140

Arg Thr Glu Met Lys Gln Glu Arg Glu Pro Val Gly Thr Cys Phe Leu
145                 150                 155                 160

Gln Asp Gly Thr Lys Thr Val Glu Tyr Ala Pro Cys Arg Ser Gln Asp
                 165                 170                 175

Ile Asp Ala Asp Gly Gln Gly Phe Cys Gln Gly Gly Phe Ser Ile Asp
             180                 185                 190

Phe Thr Lys Ala Asp Arg Val Leu Leu Gly Gly Pro Gly Ser Phe Tyr
         195                 200                 205

Trp Gln Gly Gln Leu Ile Ser Asp Gln Val Ala Glu Ile Val Ser Lys
210                 215                 220

Tyr Asp Pro Asn Val Tyr Ser Ile Lys Tyr Asn Asn Gln Leu Ala Thr
225                 230                 235                 240

Arg Thr Ala Gln Ala Ile Phe Asp Asp Ser Tyr Leu Gly Tyr Ser Val
                 245                 250                 255

Ala Val Gly Asp Phe Asn Gly Asp Gly Ile Asp Asp Phe Val Ser Gly
             260                 265                 270

Val Pro Arg Ala Ala Arg Thr Leu Gly Met Val Tyr Ile Tyr Asp Gly
         275                 280                 285

Lys Asn Met Ser Ser Leu Tyr Asn Phe Thr Gly Glu Gln Met Ala Ala
290                 295                 300

Tyr Phe Gly Phe Ser Val Ala Ala Thr Asp Ile Asn Gly Asp Asp Tyr
305                 310                 315                 320

Ala Asp Val Phe Ile Gly Ala Pro Leu Phe Met Asp Arg Gly Ser Asp
                 325                 330                 335

Gly Lys Leu Gln Glu Val Gly Gln Val Ser Val Ser Leu Gln Arg Ala
             340                 345                 350

Ser Gly Asp Phe Gln Thr Thr Lys Leu Asn Gly Phe Glu Val Phe Ala
         355                 360                 365

Arg Phe Gly Ser Ala Ile Ala Pro Leu Gly Asp Leu Asp Gln Asp Gly
 370                 375                 380

Phe Asn Asp Ile Ala Ile Ala Ala Pro Tyr Gly Gly Glu Asp Lys Lys
385                 390                 395                 400

Gly Ile Val Tyr Ile Phe Asn Gly Arg Ser Thr Gly Leu Asn Ala Val
                 405                 410                 415

Pro Ser Gln Ile Leu Glu Gly Gln Trp Ala Ala Arg Ser Met Pro Pro
             420                 425                 430

Ser Phe Gly Tyr Ser Met Lys Gly Ala Thr Asp Ile Asp Lys Asn Gly
```

```
                 435              440              445
Tyr Pro Asp Leu Ile Val Gly Ala Phe Gly Val Asp Arg Ala Ile Leu
            450              455              460
Tyr Arg Ala Arg Pro Val Ile Thr Val Asn Ala Gly Leu Glu Val Tyr
465              470              475              480
Pro Ser Ile Leu Asn Gln Asp Asn Lys Thr Cys Ser Leu Pro Gly Thr
                 485              490              495
Ala Leu Lys Val Ser Cys Phe Asn Val Arg Phe Cys Leu Lys Ala Asp
            500              505              510
Gly Lys Gly Val Leu Pro Arg Lys Leu Asn Phe Gln Val Glu Leu Leu
            515              520              525
Leu Asp Lys Leu Lys Gln Lys Gly Ala Ile Arg Arg Ala Leu Phe Leu
530              535              540
Tyr Ser Arg Ser Pro Ser His Ser Lys Asn Met Thr Ile Ser Arg Gly
545              550              555              560
Gly Leu Met Gln Cys Glu Glu Leu Ile Ala Tyr Leu Arg Asp Glu Ser
                 565              570              575
Glu Phe Arg Asp Lys Leu Thr Pro Ile Thr Ile Phe Met Glu Tyr Arg
            580              585              590
Leu Asp Tyr Arg Thr Ala Ala Asp Thr Thr Gly Leu Gln Pro Ile Leu
            595              600              605
Asn Gln Phe Thr Pro Ala Asn Ile Ser Arg Gln Ala His Ile Leu Leu
            610              615              620
Asp Cys Gly Glu Asp Asn Val Cys Lys Pro Lys Leu Glu Val Ser Val
625              630              635              640
Asp Ser Asp Gln Lys Lys Ile Tyr Ile Gly Asp Asp Asn Pro Leu Thr
                 645              650              655
Leu Ile Val Lys Ala Gln Asn Gln Gly Glu Gly Ala Tyr Glu Ala Glu
                 660              665              670
Leu Ile Val Ser Ile Pro Leu Gln Ala Asp Phe Ile Gly Val Val Arg
            675              680              685
Asn Asn Glu Ala Leu Ala Arg Leu Ser Cys Ala Phe Lys Thr Glu Asn
690              695              700
Gln Thr Arg Gln Val Val Cys Asp Leu Gly Asn Pro Met Lys Ala Gly
705              710              715              720
Thr Gln Leu Leu Ala Gly Leu Arg Phe Ser Val His Gln Gln Ser Glu
            725              730              735
Met Asp Thr Ser Val Lys Phe Asp Leu Gln Ile Gln Ser Ser Asn Leu
            740              745              750
Phe Asp Lys Val Ser Pro Val Val Ser His Lys Val Asp Leu Ala Val
            755              760              765
Leu Ala Ala Val Glu Ile Arg Gly Val Ser Ser Pro Asp His Ile Phe
770              775              780
Leu Pro Ile Pro Asn Trp Glu His Lys Glu Asn Pro Glu Thr Glu Glu
785              790              795              800
Asp Val Gly Pro Val Val Gln His Ile Tyr Glu Leu Arg Asn Asn Gly
                 805              810              815
Pro Ser Ser Phe Ser Lys Ala Met Leu His Leu Gln Trp Pro Tyr Lys
            820              825              830
Tyr Asn Asn Asn Thr Leu Leu Tyr Ile Leu His Tyr Asp Ile Asp Gly
            835              840              845
Pro Met Asn Cys Thr Ser Asp Met Glu Ile Asn Pro Leu Arg Ile Lys
850              855              860
```

```
Ile Ser Ser Leu Gln Thr Thr Glu Lys Asn Asp Thr Val Ala Gly Gln
865                 870                 875                 880

Gly Glu Arg Asp His Leu Ile Thr Lys Arg Asp Leu Ala Leu Ser Glu
            885                 890                 895

Gly Asp Ile His Thr Leu Gly Cys Gly Val Ala Gln Cys Leu Lys Ile
            900                 905                 910

Val Cys Gln Val Gly Arg Leu Asp Arg Gly Lys Ser Ala Ile Leu Tyr
            915                 920                 925

Val Lys Ser Leu Leu Trp Thr Glu Thr Phe Met Asn Lys Glu Asn Gln
            930                 935                 940

Asn His Ser Tyr Ser Leu Lys Ser Ser Ala Ser Phe Asn Val Ile Glu
945                 950                 955                 960

Phe Pro Tyr Lys Asn Leu Pro Ile Glu Asp Ile Thr Asn Ser Thr Leu
                965                 970                 975

Val Thr Thr Asn Val Thr Trp Gly Ile Gln Pro Ala Pro Met Pro Val
            980                 985                 990

Pro Val Trp Val Ile Ile Leu Ala  Val Leu Ala Gly Leu  Leu Leu Leu
        995                 1000                1005

Ala Val  Leu Val Phe Val Met  Tyr Arg Met Gly Phe  Phe Lys Arg
    1010                1015                1020

Val Arg  Pro Pro Gln Glu Gln  Glu Arg Glu Gln  Leu Gln Pro
    1025                1030                1035

His Glu  Asn Gly Glu Gly Asn  Ser Glu Thr
    1040                1045

<210> SEQ ID NO 10
<211> LENGTH: 15
<212> TYPE: DNA
<213> ORGANISM: Homo sapiens

<400> SEQUENCE: 10
agatatacta tgcac                                                    15

<210> SEQ ID NO 11
<211> LENGTH: 51
<212> TYPE: DNA
<213> ORGANISM: Homo sapiens

<400> SEQUENCE: 11
gttatatcat tgatggaag caataaatac tacgtagact ccgtgaaggg c              51

<210> SEQ ID NO 12
<211> LENGTH: 30
<212> TYPE: DNA
<213> ORGANISM: Homo sapiens

<400> SEQUENCE: 12
gaggcccggg gatcgtatgc ttttgatatc                                    30

<210> SEQ ID NO 13
<211> LENGTH: 42
<212> TYPE: DNA
<213> ORGANISM: Homo sapiens

<400> SEQUENCE: 13
ctctcctgca gggccagtca gagtgttagc agctacttag cc                      42

<210> SEQ ID NO 14
```

```
<211> LENGTH: 18
<212> TYPE: DNA
<213> ORGANISM: Homo sapiens

<400> SEQUENCE: 14
gatgcatcca acagggcc                                                        18

<210> SEQ ID NO 15
<211> LENGTH: 21
<212> TYPE: DNA
<213> ORGANISM: Homo sapiens

<400> SEQUENCE: 15
cagcagcgta gcaactggcc t                                                    21

<210> SEQ ID NO 16
<211> LENGTH: 788
<212> TYPE: PRT
<213> ORGANISM: Homo sapiens

<400> SEQUENCE: 16
```

Met Arg Ala Arg Pro Arg Pro Arg Pro Leu Trp Ala Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
        35                  40                  45

Cys Ala Trp Cys Ser Asp Glu Ala Leu Pro Leu Gly Ser Pro Arg Cys
    50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
        195                 200                 205

Thr Cys Leu Pro Met Phe Gly Tyr Lys His Val Leu Thr Leu Thr Asp
    210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                245                 250                 255

Val Cys Asp Glu Lys Ile Gly Trp Arg Asn Asp Ala Ser His Leu Leu
            260                 265                 270

Val Phe Thr Thr Asp Ala Lys Thr His Ile Ala Leu Asp Gly Arg Leu
        275                 280                 285

-continued

```
Ala Gly Ile Val Gln Pro Asn Asp Gly Gln Cys His Val Gly Ser Asp
    290                 295                 300

Asn His Tyr Ser Ala Ser Thr Thr Met Asp Tyr Pro Ser Leu Gly Leu
305                 310                 315                 320

Met Thr Glu Lys Leu Ser Gln Lys Asn Ile Asn Leu Ile Phe Ala Val
                325                 330                 335

Thr Glu Asn Val Val Asn Leu Tyr Gln Asn Tyr Ser Glu Leu Ile Pro
            340                 345                 350

Gly Thr Thr Val Gly Val Leu Ser Met Asp Ser Ser Asn Val Leu Gln
        355                 360                 365

Leu Ile Val Asp Ala Tyr Gly Lys Ile Arg Ser Lys Val Glu Leu Glu
    370                 375                 380

Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
                405                 410                 415

Ile Gly Asp Thr Val Ser Phe Ser Ile Glu Ala Lys Val Arg Gly Cys
            420                 425                 430

Pro Gln Glu Lys Glu Lys Ser Phe Thr Ile Lys Pro Val Gly Phe Lys
        435                 440                 445

Asp Ser Leu Ile Val Gln Val Thr Phe Asp Cys Asp Cys Ala Cys Gln
    450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                485                 490                 495

Cys Glu Cys Ser Glu Glu Asp Tyr Arg Pro Ser Gln Gln Asp Glu Cys
            500                 505                 510

Ser Pro Arg Glu Gly Gln Pro Val Cys Ser Gln Arg Gly Glu Cys Leu
        515                 520                 525

Cys Gly Gln Cys Val Cys His Ser Ser Asp Phe Gly Lys Ile Thr Gly
    530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
                565                 570                 575

Ser Asp Trp Thr Gly Tyr Tyr Cys Asn Cys Thr Thr Arg Thr Asp Thr
            580                 585                 590

Cys Met Ser Ser Asn Gly Leu Leu Cys Ser Gly Arg Gly Lys Cys Glu
        595                 600                 605

Cys Gly Ser Cys Val Cys Ile Gln Pro Gly Ser Tyr Gly Asp Thr Cys
    610                 615                 620

Glu Lys Cys Pro Thr Cys Pro Asp Ala Cys Thr Phe Lys Lys Glu Cys
625                 630                 635                 640

Val Glu Cys Lys Lys Phe Asp Arg Glu Pro Tyr Met Thr Glu Asn Thr
                645                 650                 655

Cys Asn Arg Tyr Cys Arg Asp Glu Ile Glu Ser Val Lys Glu Leu Lys
            660                 665                 670

Asp Thr Gly Lys Asp Ala Val Asn Cys Thr Tyr Lys Asn Glu Asp Asp
        675                 680                 685

Cys Val Val Arg Phe Gln Tyr Tyr Glu Asp Ser Ser Gly Lys Ser Ile
    690                 695                 700
```

```
Leu Tyr Val Val Glu Glu Pro Glu Cys Pro Lys Gly Pro Asp Ile Leu
705                 710                 715                 720

Val Val Leu Leu Ser Val Met Gly Ala Ile Leu Leu Ile Gly Leu Ala
                725                 730                 735

Ala Leu Leu Ile Trp Lys Leu Leu Ile Thr Ile His Asp Arg Lys Glu
            740                 745                 750

Phe Ala Lys Phe Glu Glu Arg Ala Arg Ala Lys Trp Asp Thr Ala
        755                 760                 765

Asn Asn Pro Leu Tyr Lys Glu Ala Thr Ser Thr Phe Thr Asn Ile Thr
    770                 775                 780

Tyr Arg Gly Thr
785

<210> SEQ ID NO 17
<211> LENGTH: 799
<212> TYPE: PRT
<213> ORGANISM: Homo sapiens

<400> SEQUENCE: 17

Met Pro Arg Ala Pro Ala Pro Leu Tyr Ala Cys Leu Leu Gly Leu Cys
1               5                   10                  15

Ala Leu Leu Pro Arg Leu Ala Gly Leu Asn Ile Cys Thr Ser Gly Ser
            20                  25                  30

Ala Thr Ser Cys Glu Glu Cys Leu Leu Ile His Pro Lys Cys Ala Trp
        35                  40                  45

Cys Ser Lys Glu Asp Phe Gly Ser Pro Arg Ser Ile Thr Ser Arg Cys
    50                  55                  60

Asp Leu Arg Ala Asn Leu Val Lys Asn Gly Cys Gly Gly Glu Ile Glu
65                  70                  75                  80

Ser Pro Ala Ser Ser Phe His Val Leu Arg Ser Leu Pro Leu Ser Ser
                85                  90                  95

Lys Gly Ser Gly Ser Ala Gly Trp Asp Val Ile Gln Met Thr Pro Gln
            100                 105                 110

Glu Ile Ala Val Asn Leu Arg Pro Gly Asp Lys Thr Thr Phe Gln Leu
        115                 120                 125

Gln Val Arg Gln Val Glu Asp Tyr Pro Val Asp Leu Tyr Tyr Leu Met
    130                 135                 140

Asp Leu Ser Leu Ser Met Lys Asp Asp Leu Asp Asn Ile Arg Ser Leu
145                 150                 155                 160

Gly Thr Lys Leu Ala Glu Glu Met Arg Lys Leu Thr Ser Asn Phe Arg
                165                 170                 175

Leu Gly Phe Gly Ser Phe Val Asp Lys Asp Ile Ser Pro Phe Ser Tyr
            180                 185                 190

Thr Ala Pro Arg Tyr Gln Thr Asn Pro Cys Ile Gly Tyr Lys Leu Phe
        195                 200                 205

Pro Asn Cys Val Pro Ser Phe Gly Phe Arg His Leu Leu Pro Leu Thr
    210                 215                 220

Asp Arg Val Asp Ser Phe Asn Glu Glu Val Arg Lys Gln Arg Val Ser
225                 230                 235                 240

Arg Asn Arg Asp Ala Pro Glu Gly Gly Phe Asp Ala Val Leu Gln Ala
                245                 250                 255

Ala Val Cys Lys Glu Lys Ile Gly Trp Arg Lys Asp Ala Leu His Leu
            260                 265                 270

Leu Val Phe Thr Thr Asp Asp Val Pro His Ile Ala Leu Asp Gly Lys
        275                 280                 285
```

```
Leu Gly Gly Leu Val Gln Pro His Asp Gly Gln Cys His Leu Asn Glu
    290                 295                 300

Ala Asn Glu Tyr Thr Ala Ser Asn Gln Met Asp Tyr Pro Ser Leu Ala
305                 310                 315                 320

Leu Leu Gly Glu Lys Leu Ala Glu Asn Asn Ile Asn Leu Ile Phe Ala
                325                 330                 335

Val Thr Lys Asn His Tyr Met Leu Tyr Lys Asn Phe Thr Ala Leu Ile
            340                 345                 350

Pro Gly Thr Thr Val Glu Ile Leu Asp Gly Asp Ser Lys Asn Ile Ile
        355                 360                 365

Gln Leu Ile Ile Asn Ala Tyr Asn Ser Ile Arg Ser Lys Val Glu Leu
    370                 375                 380

Ser Val Trp Asp Gln Pro Glu Asp Leu Asn Leu Phe Phe Thr Ala Thr
385                 390                 395                 400

Cys Gln Asp Gly Val Ser Tyr Pro Gly Gln Arg Lys Cys Glu Gly Leu
                405                 410                 415

Lys Ile Gly Asp Thr Ala Ser Phe Glu Val Ser Leu Glu Ala Arg Ser
            420                 425                 430

Cys Pro Ser Arg His Thr Glu His Val Phe Ala Leu Arg Pro Val Gly
        435                 440                 445

Phe Arg Asp Ser Leu Glu Val Gly Val Thr Tyr Asn Cys Thr Cys Gly
    450                 455                 460

Cys Ser Val Gly Leu Glu Pro Asn Ser Ala Arg Cys Asn Gly Ser Gly
465                 470                 475                 480

Thr Tyr Val Cys Gly Leu Cys Glu Cys Ser Pro Gly Tyr Leu Gly Thr
                485                 490                 495

Arg Cys Glu Cys Gln Asp Gly Glu Asn Gln Ser Val Tyr Gln Asn Leu
            500                 505                 510

Cys Arg Glu Ala Glu Gly Lys Pro Leu Cys Ser Gly Arg Gly Asp Cys
        515                 520                 525

Ser Cys Asn Gln Cys Ser Cys Phe Glu Ser Glu Phe Gly Lys Ile Tyr
    530                 535                 540

Gly Pro Phe Cys Glu Cys Asp Asn Phe Ser Cys Ala Arg Asn Lys Gly
545                 550                 555                 560

Val Leu Cys Ser Gly His Gly Glu Cys His Cys Gly Glu Cys Lys Cys
                565                 570                 575

His Ala Gly Tyr Ile Gly Asp Asn Cys Asn Cys Ser Thr Asp Ile Ser
            580                 585                 590

Thr Cys Arg Gly Arg Asp Gly Gln Ile Cys Ser Glu Arg Gly His Cys
        595                 600                 605

Leu Cys Gly Gln Cys Gln Cys Thr Glu Pro Gly Ala Phe Gly Glu Met
    610                 615                 620

Cys Glu Lys Cys Pro Thr Cys Pro Asp Ala Cys Ser Thr Lys Arg Asp
625                 630                 635                 640

Cys Val Glu Cys Leu Leu Leu His Ser Gly Lys Pro Asp Asn Gln Thr
                645                 650                 655

Cys His Ser Leu Cys Arg Asp Glu Val Ile Thr Trp Val Asp Thr Ile
            660                 665                 670

Val Lys Asp Asp Gln Glu Ala Val Leu Cys Phe Tyr Lys Thr Ala Lys
        675                 680                 685

Asp Cys Val Met Met Phe Thr Tyr Val Glu Leu Pro Ser Gly Lys Ser
    690                 695                 700
```

```
Asn Leu Thr Val Leu Arg Glu Pro Glu Cys Gly Asn Thr Pro Asn Ala
705                 710                 715                 720

Met Thr Ile Leu Leu Ala Val Val Gly Ser Ile Leu Leu Val Gly Leu
            725                 730                 735

Ala Leu Leu Ala Ile Trp Lys Leu Leu Val Thr Ile His Asp Arg Arg
            740                 745                 750

Glu Phe Ala Lys Phe Gln Ser Glu Arg Ser Arg Ala Arg Tyr Glu Met
        755                 760                 765

Ala Ser Asn Pro Leu Tyr Arg Lys Pro Ile Ser Thr His Thr Val Asp
    770                 775                 780

Phe Thr Phe Asn Lys Phe Asn Lys Ser Tyr Asn Gly Thr Val Asp
785                 790                 795
```